(12) United States Patent
Tohi et al.

(10) Patent No.: US 7,393,965 B2
(45) Date of Patent: Jul. 1, 2008

(54) CROSSLINKED METALLOCENE COMPOUND FOR OLEFIN POLYMERIZATION AND METHOD OF POLYMERIZING OLEFIN WITH THE SAME

(75) Inventors: Yasushi Tohi, Sodegaura (JP); Koji Endo, Sodegaura (JP); Hiromu Kaneyoshi, Sodegaura (JP); Naomi Urakawa, Sodegaura (JP); Yuichi Yamamura, Sodegaura (JP); Koji Kawai, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 67 days.

(21) Appl. No.: 10/529,461

(22) PCT Filed: Feb. 17, 2003

(86) PCT No.: PCT/JP03/01656

§ 371 (c)(1),
(2), (4) Date: Oct. 28, 2005

(87) PCT Pub. No.: WO2004/029062

PCT Pub. Date: Apr. 8, 2004

(65) Prior Publication Data
US 2006/0161013 A1 Jul. 20, 2006

(30) Foreign Application Priority Data

Sep. 27, 2002 (JP) ............................. 2002-283291
Nov. 22, 2002 (JP) ............................. 2002-339670

(51) Int. Cl.
C07F 17/00 (2006.01)
C07F 7/00 (2006.01)
B01J 31/00 (2006.01)

(52) U.S. Cl. ........................... 556/11; 556/12; 502/103; 502/117; 526/160; 526/943

(58) Field of Classification Search .................. 556/11, 556/12; 502/103, 117; 526/160, 943
See application file for complete search history.

(56) References Cited

U.S. PATENT DOCUMENTS 5,886,202 A 3/1999 Jung 6,469,188 B1 * 10/2002 Miller et al. .................. 556/12
2002/0137959 A1 9/2002 Rix

FOREIGN PATENT DOCUMENTS

| CN | 1328580 A | 12/2001 |
|---|---|---|
| EP | 5 775 81 A2 | 1/1994 |
| EP | 6 854 95 A1 | 12/1995 |
| EP | 1 138 687 A1 | 10/2001 |
| JP | 2-41303 A | 2/1990 |
| JP | 2-78687 A | 3/1990 |
| JP | 2-167305 A | 6/1990 |
| JP | 2-274703 A | 11/1990 |
| JP | 3-103407 A | 4/1991 |
| JP | 3-193797 A | 8/1991 |
| JP | 4-69394 A | 3/1992 |
| JP | 05-059077 * | 3/1993 |
| JP | 5-125112 A | 5/1993 |
| JP | 6-172443 A | 6/1994 |
| JP | 07-157508 A | 6/1995 |
| JP | 2000-26490 A | 1/2000 |
| JP | 2000-212194 A | 8/2000 |
| WO | WO-00/24793 A1 | 5/2000 |
| WO | WO-01/27124 A1 | 4/2001 |

OTHER PUBLICATIONS

Kaminsky et al., Angew. Chem. Int. Ed. Engl., 24, 507-508 (1985).
Ewen et al., J. Amer. Chem. Soc., 110, 6255-6256 (1988).
Kaminsky et al., Makromol. Chem. 193, 1643-1651 (1992).
Chen et al., Journal of Organometallic Chemistry 497 (1995) pp. 1-9.
Patsidis et al., Journal of Organometallic Chemistry 509 (1996) pp. 63-71.

* cited by examiner

*Primary Examiner*—Porfirio Nazario Gonzale
(74) *Attorney, Agent, or Firm*—Birch, Stewart, Kolasch & Birch, LLP

(57) ABSTRACT

The bridged metallocene compound or the olefin polymerization catalyst which comprises the compound, enables high polymerization activity in polymerizing one or more monomers selected from ethylene and α-olefins. The bridged metallocene compound contains specific substituted cyclopentadienyl and fluorenyl groups which are linked via carbon or silicon atoms. In the method for the preparation of polyolefins, one or more monomers, preferably ethylene as an essential monomer, selected from ethylene and α-olefins are copolymerized in the presence of the olefin polymerization catalyst comprising the bridged metallocene compound, so that an ethylene based polymer with an ethylene content of more than 50 mol % is obtained.

16 Claims, No Drawings

CROSSLINKED METALLOCENE COMPOUND FOR OLEFIN POLYMERIZATION AND METHOD OF POLYMERIZING OLEFIN WITH THE SAME

FIELD OF THE INVENTION

The present invention relates to a bridged metallocene compound of specific structure useful as a catalyst or a catalyst component for polymerization of olefins, and to a method for polymerization of one or more monomers selected from ethylene and α-olefins in the presence of a catalyst containing the bridged metallocene compound.

BACKGROUND OF THE INVENTION

Metallocene compounds are well known as homogeneous catalysts for polymerization of olefins. Polymerization of olefins using these metallocene compounds, particularly stereoregular polymerization of α-olefins, has improved much since the report of isotactic polymerization by W. Kaminsky et al. (Angew. Chem. Int. Ed. Engl., 24, 507 (1985)), but further improvement has been required in terms of polymerization activity and stereoregularity. As part of studies for the improvement, propylene polymerization using a metallocene compound in which a cyclopentadienyl ligand and a fluorenyl ligand are bridged, has been reported by J. A. Ewen (J. Am. Chem. Soc., 110, 6255 (1988)). Further, W. Kaminsky has reported ethylene polymerization using the same catalyst (Makromol. Chem., 193, 1643 (1992)).

However, polymerization of ethylene as a major monomer has suffered insufficient polymerization activity, so that a transition metal compound capable of enhanced polymerization activity or a polymerization catalyst comprising the transition metal compound has been demanded.

DISCLOSURE OF THE INVENTION

A bridged metallocene compound (W) of the invention (sometimes referred to as a "metallocene compound" hereinafter) is represented by the formula [I]:

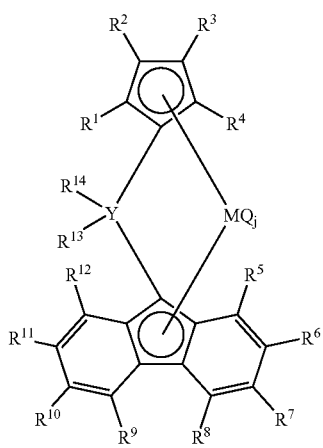

[I]

wherein Y is a carbon, silicon, germanium or tin atom; M is Ti, Zr or Hf, $R^1$ to $R^{12}$, which may be the same or different, are each hydrogen, a hydrocarbon group or a silicon-containing group; neighboring substituents of $R^5$ to $R^{12}$ may be linked with each other to form a ring; $R^{13}$ and $R^{14}$, which may be the same or different, are each a hydrocarbon group or a silicon containing group and may be linked with each other to form a ring (when $R^5$ to $R^{12}$ are all hydrogen or when $R^6$ and $R^{11}$ are both hydrocarbon groups, $R^{13}$ and $R^{14}$ are hydrocarbon groups other than phenyl, methyl and pentamethylene groups, and when $R^7$ and $R^{10}$ are both hydrocarbon groups, $R^{13}$ and $R^{14}$ are hydrocarbon groups other than phenyl and methyl groups); Q is a halogen, a hydrocarbon group, an anionic ligand or a neutral ligand capable of coordination by a lone pair of electrons, and may be the same or different when plural; and j is an integer from 1 to 4.

The metallocene compound (W) of the formula [I] can be classified into five types (W-1) to (W-5) by the chemical structure. These preferable metallocene compounds (W-1) to (W-5) are represented by the formula [I-1] to [I-5] respectively. When the metallocene compound has plural characteristic structures, it will be represented by corresponding plural formulae of [I-1] to [I-5].

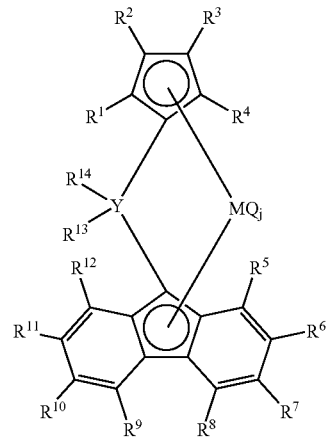

[I]

Metallocene compound (W-1)

In the formula [I-1], $R^1$ to $R^{12}$, which may be the same or different, are each hydrogen, a hydrocarbon group or a silicon-containing group; neighboring substituents of $R^1$ to $R^{12}$ may be linked with each other to form a ring; M is Ti or Zr; Y is a Group 14 atom; Q is a halogen, a hydrocarbon group, an anionic ligand or a neutral ligand capable of coordination by a lone pair of electrons, and may be the same or different when plural; j is an integer from 1 to 4; $R^{13}$ is an unsubstituted or substituted aryl group, $R^{14}$ is a substituted aryl group, and $R^{13}$ and $R^{14}$ may the same or different when $R^{13}$ is a substituted aryl group.

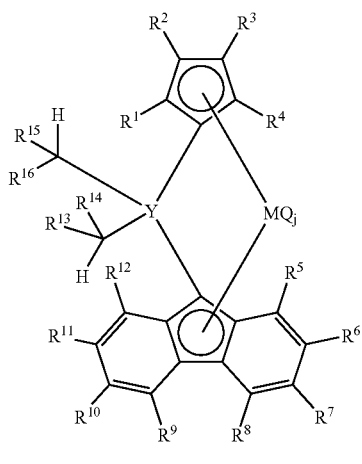

Metallocene compound (W-2)

In the formula [I-2], $R^1$ to $R^{16}$, which may be the same or different, are each hydrogen, a hydrocarbon group or a silicon-containing group; neighboring substituents of $R^1$ to $R^{12}$ may be linked with each other to form a ring; $R^{13}$ to $R^{16}$ cannot be hydrogen at the same time; $R^{13}$ and $R^{14}$ may be linked with each other to form a ring; $R^{15}$ and $R^{16}$ may be linked with each other to form a ring; M is Ti, Zr or Hf; Y is a carbon atom; Q is a halogen, a hydrocarbon group, an anionic ligand or a neutral ligand capable of coordination by a lone pair of electrons, and may be the same or different when plural; and j is an integer from 1 to 4.

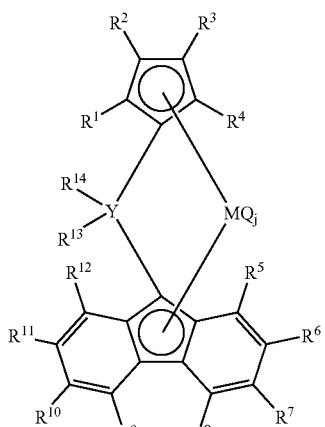

Metallocene compound (W-4)

In the formula [I-4], $R^1$ to $R^{14}$, which may be the same or different, are each hydrogen, a hydrocarbon group or a silicon-containing group; arbitrary three or more groups of $R^6$, $R^7$, $R^{10}$ and $R^{11}$ cannot be hydrogen at the same time; neighboring substituents of $R^5$ to $R^{12}$ may be linked with each other to form a ring; $R^{13}$ and $R^{14}$, which may be the same or different, are each a hydrocarbon group or a silicon-containing group and may be linked with each other to form a ring; Y is a carbon atom; M is Ti, Zr or Hf; Q is a halogen, a hydrocarbon group, an anionic ligand or a neutral ligand capable of coordination by a lone pair of electrons, and may be the same or different when plural; and j is an integer from 1 to 4.

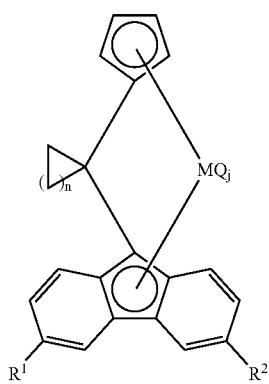

Metallocene compound (W-3)

In the formula [I-3], $R^1$ and $R^2$, which may be the same or different, are each hydrogen, a hydrocarbon group, a silicon-containing group or a halogen-containing group; M is Ti, Zr or Hf; Q is a halogen, a hydrocarbon group, an anionic ligand or a neutral ligand capable of coordination by a lone pair of electrons, and may be the same or different when plural; n is an integer from 1 to 10; and j is an integer from 1 to 4.

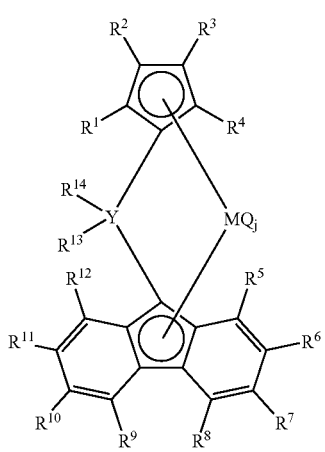

Metallocene compound (W-5)

In the formula [I-5], $R^1$ to $R^{12}$, which may be the same or different, are each hydrogen, a hydrocarbon group or a silicon-containing group but cannot be hydrogen at the same time; neighboring substituents of $R^1$ to $R^{12}$ may be linked with each other to form a ring; Y is a silicon, germanium or tin atom; $R^{13}$ and $R^{14}$, which may be the same or different, are each a hydrocarbon group or a silicon-containing group and may be linkedwitheachother to forma ring; $R^6$ and $R^{11}$ cannot be t-butyl groups when $R^{13}$ and $R^{14}$ are both methyl or phenyl groups; M is Ti, Zr or Hf; Q is a halogen, a hydrocarbon group, an anionic ligand or a neutral ligand capable of coordination by a lone pair of electrons, and may be the same or different when plural; and j is an integer from 1 to 4.

An olefin polymerization catalyst of the invention comprises the metallocene compound (W), preferably one of the metallocene compounds (W-1) to (W-5).

Specifically, the olefin polymerization catalyst comprises:
(A) the metallocene compound (W) and
(B) at least one compound selected from:
(B-1) an organometallic compound,
(B-2) an organoaluminum oxy-compound and
(B-3) a compound which reacts with the metallocene compound (A) to form an ion pair.

A method for olefin polymerization according to the invention is dedicated for polymerization of one or more monomers selected from ethylene and α-olefins, in which ethylene is an essential monomer. The polymerization is carried out in the presence of an olefin polymerization catalyst which contains the bridged metallocene compound (W) of the formula [I] so that an ethylene based polymer with an ethylene content of more than 50 mol % is obtained.

In another embodiment, the method for olefin polymerization is dedicated for polymerization of one or more monomers selected from ethylene and α-olefins, in which ethylene is an essential monomer. The polymerization is carried out in the presence of an olefin polymerization catalyst which contains the bridged metallocene compound (W') of the formula [I'] so that an ethylene based polymer with an ethylene content of more than 50 mol % is obtained.

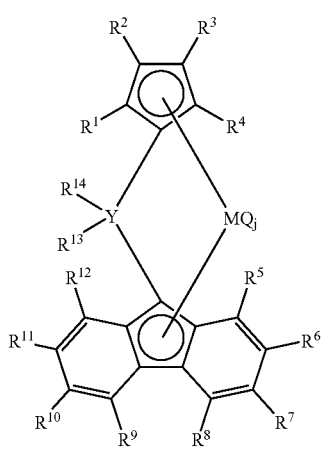

[I']

In the formula [I'], Y is a carbon, silicon, germanium or tin atom; M is Ti, Zr or Hf; $R^1$ to $R^{12}$, which may be the same or different, are each hydrogen, a hydrocarbon group or a silicon-containing group; $R^5$ to $R^{12}$ cannot be hydrogen at the same time; neighboring substituents of $R^5$ to $R^{12}$ may be linked with each other to form a ring; $R^{13}$ and $R^{14}$, which may be the same or different, are each a hydrocarbon group or a silicon-containing group and may be linked with each other to form a ring; Q is a halogen, a hydrocarbon group, an anionic ligand or a neutral ligand capable of coordination by a lone pair of electrons, and maybe the same or different when plural; and j is an integer from 1 to 4.

The bridged metallocene compounds (W') of the formula [I'] in which $R^{13}$ and $R^{14}$ are phenyl, methyl or pentamethylene groups, are defined as metallocene compounds (T), most of which are already well known.

In the method for olefin polymerization, the metallocene compound (W) or (W') of the formula [I] or [I'] may have been supported on a carrier.

BEST MODE TO CARRY OUT THE INVENTION

The metallocene compounds, production thereof, olefin polymerization catalyst containing the metallocene compound, and method for olefin polymerization using the olefin polymerization catalyst will be described hereinafter.

Metallocene Compound

The metallocene compounds can be categorized into the following two major types:

1st category: novel metallocene compounds (W) useful as a constituent of catalyst for polymerization of essential ethylene and other optional olefins 2nd category: metallocene compounds (T) useful as a constituent of catalyst for polymerization of essential ethylene and other optional olefins.

The "essential ethylene" as used herein means that ethylene is essentially used as a monomer for polymerization optionally with at least one α-olefin so that an ethylene based polymer with an ethylene content of more than 50 mol % is obtained.

The metallocene compounds (W) of 1st category are novel in the art. Therefore, the olefin polymerization catalyst containing the metallocene compound (W), and the method for polymerization of the olefins in the presence of the olefin polymerization catalyst are also novel in the art.

The metallocene compounds (T) of 2nd category are known in the art. However, there has been no technology for polymerization of the olefins in the presence of the olefin polymerization catalyst which contains the metallocene compound (T).

In the present invention, the metallocene compound as a constituent of the olefin polymerization catalyst may be the metallocene compound (W) of 1st category or the metallocene compound (T) of 2nd category.

Metallocene Compound (W)

The metallocene compound (W) is represented by the formula [I]:

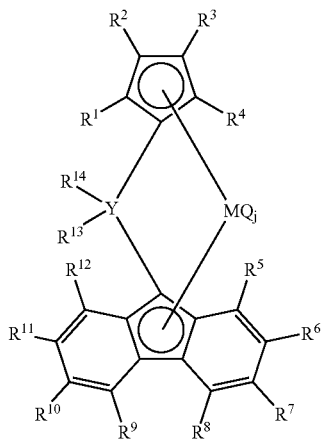

[I]

wherein Y is a carbon, silicon, germanium or tin atom; M is Ti, Zr or Hf; $R^1$ to $R^{12}$, which may be the same or different, are each hydrogen, a hydrocarbon group or a silicon-containing group; and neighboring substituents of $R^5$ to $R^{12}$ may be linked with each other to form a ring.

The hydrocarbon group is preferably of 1 to 20 carbon atoms. Examples thereof include alkyl, alkenyl, alkynyl and aryl groups which consist of carbon and hydrogen; and corresponding groups to the above groups in which part of hydrogen atoms connected with carbon is substituted with a halogen atom or an oxygen-, nitrogen- or silicon-containing group, or in which arbitrary two adjacent hydrogen atoms are both substituted to form an alicyclic or aromatic ring.

Examples of the hydrocarbon group of 1 to 20 carbon atoms include linear hydrocarbon groups, such as methyl, ethyl, n-propyl, allyl, n-butyl, n-pentyl, n-hexyl, n-heptyl, n-octyl, n-nonyl and n-decanyl groups; branched hydrocarbon groups, such as isopropyl, isobutyl, s-butyl, t-butyl, t-amyl, neopentyl, 3-methylpentyl, 1,1-diethylpropyl, 1,1-dimethylbutyl, 1-methyl-1-propylbutyl, 1,1-dipropylbutyl, 1,1-dimethyl-2-methylpropyl, 1-methyl-1-isopropyl-2-methylpropyl and cyclopropylmethyl groups; cyclic saturated hydrocarbon groups, such as cyclopropyl, cyclobutyl, cyclopentyl, cyclohexyl, cycloheptyl, cyclooctyl, norbornyl and adamantyl groups; cyclic unsaturated hydrocarbon groups, such as phenyl, naphthyl, biphenyl, phenanthryl and anthracenyl groups; saturated hydrocarbon groups which are substituted with aryl groups, such as benzyl and cumyl groups; oxygen-containing hydrocarbon groups, such as methoxy, ethoxy and phenoxy groups; nitrogen-containing hydrocarbon groups, such as N-methylamino, N,N-dimethylamino and N-phenylamino groups; and halogen-containing hydrocarbon groups, such as trifluoromethyl, tribromomethyl, pentafluoroethyl and pentafluorophenyl groups.

Examples of the silicon-containing group include cyclopentadienyl, indenyl and fluorenyl groups in which the ring carbon has a direct covalent bond with silicon. Specific examples include alkylsilyl groups, such as trimethylsilyl and triethylsilyl groups, and arylsilyl groups.

$R^{13}$ and $R^{14}$, which may be the same or different, are each a hydrocarbon group or a silicon-containing group and may be linked with each other to form a ring. Examples of the hydrocarbon group and silicon-containing group are as listed above.

For example, such metallocene compounds (W—R) can be represented by the formula [I-R]:

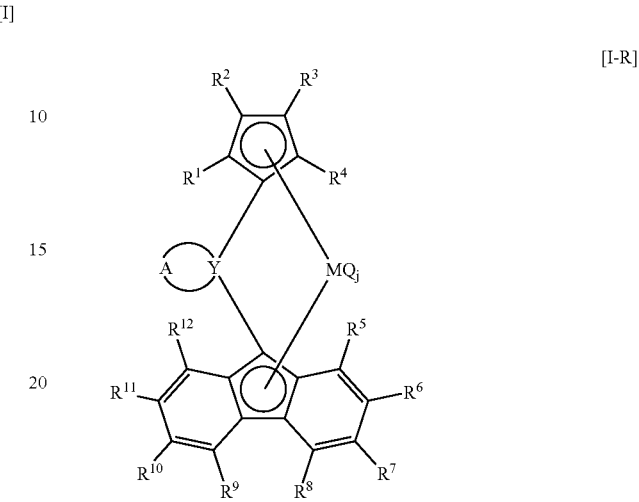

[I-R]

wherein A is a divalent hydrocarbon group of 2 to 20 carbon atoms optionally with an unsaturated bond, and may have two or more ring structures containing the A-Y ring depicted above. Examples of the ring structure include cyclopropylidene, cyclobutylidene, cyclopentylidene, cyclohexylidene, cycloheptylidene, bicyclo[3.3.1]nonylidene, norbornylidene, adamantylidene, tetrahydronaphthylidene, dihydroindanylidene, cyclodimethylenesilylene, cyclotrimethylenesilylene, cyclotetramethylenesilylene, cyclopentamethylenesilylene, cyclohexamethylenesilylene and cycloheptamethylenesilylene.

An important feature in the metallocene compound (W) of the formula [I] is that $R^{13}$ and are hydrocarbon groups other than phenyl, methyl and pentamethylene groups when (i) $R^5$ to $R^{12}$ are all hydrogen or when (ii) $R^6$ and $R^{11}$ are both hydrocarbon groups. The metallocene compound with such condition is more preferable as a constituent for the olefin polymerization catalyst.

Another important feature is that $R^{13}$ and $R^{14}$ are hydrocarbon groups other than phenyl and methyl groups when $R^7$ and $R^{10}$ are both hydrocarbon groups. The metallocene compound with such condition is more preferable as a constituent for the olefin polymerization catalyst.

Q is a halogen, a hydrocarbon group, an anionic ligand or a neutral ligand capable of coordination by a lone pair of electrons, and may be the same or different when plural. j is an integer from 1 to 4.

Examples of the halogen include fluorine, chlorine, bromine and iodine. Examples of the hydrocarbon group are as listed above.

Examples of the anionic ligand include alkoxy groups, such as methoxy, tert-butoxy and phenoxy; carboxylate groups, such as acetate and benzoate; and sulfonate groups, such as mesylate and tosylate.

Examples of the neutral ligand capable of coordination by a lone pair of electrons include organophosphorus compounds, such as trimethylphosphine, triethylphosphine, triphenylphosphine and diphenylmethylphosphine; and ethers, such as tetrahydrofuran, diethylether, dioxane and 1,2-dimethoxyethane. When Q is plural, at least one is preferably the halogen or alkyl group.

The preferable metallocene compounds (W-1) to (W-5) will be sequentially described.

Metallocene compound (W-1)

The metallocene compound (W-1) is represented by the formula [I-1]:

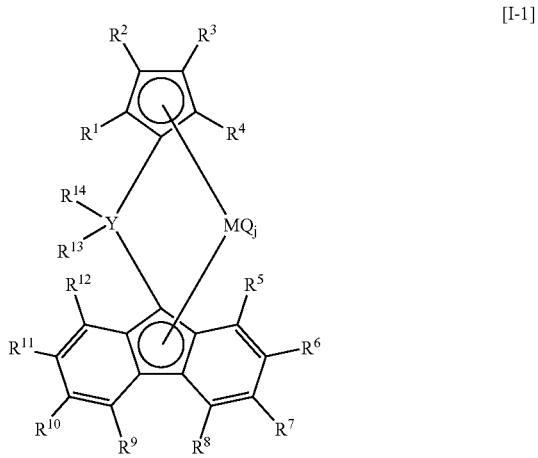

[I-1]

wherein $R^1$ to $R^{12}$ which may be the same or different, are each hydrogen, a hydrocarbon group or a silicon-containing group; and neighboring substituents of $R^1$ to $R^{12}$ may be linked with each other to form a ring. Examples of the hydrocarbon group and the silicon-containing group are as defined with respect to the metallocene compound (W). In the formula [I-1], $R^1$ to $R^4$ are preferably all hydrogen; M is Ti or Zr; Y is a Group 14 atom, preferably carbon or silicon; $R^{13}$ is an unsubstituted or substituted aryl group; and $R^{14}$ is a substituted aryl group. The "unsubstituted aryl group" as used herein can be defined as a group in which all the aromatic nucleus carbons except the one linked with Y are linked with hydrogen. The "substituted aryl group" as used herein can be defined as a group in which at least one of the aromatic nucleus carbons except the one linked with Y is linked with an atom or a group other than hydrogen. Examples of the aryl group include phenyl, naphthyl and anthracenyl groups, with a phenyl group preferable.

Examples of the substituent for the substituted aryl group include hydrocarbon groups of 1 to 20 carbon atoms, halogens and silicon-containing groups. Exemplary hydrocarbon groups of 1 to 20 carbon atoms are alkyl, alkenyl, alkynyl and aryl groups which consist of carbon and hydrogen; and corresponding groups to the above groups in which part of hydrogen atoms connected with carbon is substituted with a halogen atom or an oxygen-, nitrogen- or silicon-containing group, or in which arbitrary two adjacent hydrogen atoms are both substituted to form an alicyclic ring.

Specific examples of the hydrocarbon groups of 1 to 20 carbon atoms as substituents include linear hydrocarbon groups, such as methyl, ethyl, n-propyl, allyl, n-butyl, n-pentyl, n-hexyl, n-heptyl, n-octyl, n-nonyl and n-decanyl groups; branched hydrocarbon groups, such as isopropyl, isobutyl, s-butyl, t-butyl, t-amyl, neopentyl, 3-methylpentyl, 1,1-diethylpropyl, 1,1-dimethylbutyl, 1-methyl-1-propylbutyl, 1,1-dipropylbutyl, 1,1-dimethyl-2-methylpropyl, 1-methyl-1-isopropyl-2-methylpropyl and cyclopropylmethyl groups; cyclic saturated hydrocarbon groups, such as cyclopropyl, cyclobutyl, cyclopentyl, cyclohexyl, cycloheptyl, cyclooctyl, norbornyl and adamantyl groups; cyclic unsaturated hydrocarbon groups, such as phenyl, naphthyl, biphenyl, phenanthryl and anthracenyl groups; saturated hydrocarbon groups which are substituted with aryl groups, such as benzyl and cumyl groups; oxygen-containing hydrocarbon groups, such as methoxy, ethoxy and phenoxy groups; nitrogen-containing hydrocarbon groups, such as N-methylamino, N,N-dimethylamino and N-phenylamino groups; and halogen-containing hydrocarbon groups, such as trifluoromethyl, tribromomethyl, pentafluoroethyl and pentafluorophenyl groups.

Examples of the halogens as substituents include fluorine, chlorine, bromine and iodine. Examples of the silicon-containing groups as substituents include trimethylsilyl and triethylsilyl groups.

The aryl group with these substituents, i.e., the substituted aryl group, is preferably substituted with hydrocarbon groups of 1 to 6 carbon atoms selected from methyl, ethyl, n-propyl, isopropyl, cyclopropylmethyl, n-butyl, isobutyl, s-butyl, t-butyl, n-pentyl, t-amyl, neopentyl, n-hexyl, 3-methylpentyl, 1-methyl-1-ethylpropyl, cyclohexyl, phenyl, pentafluorophenyl and trifluoromethyl groups. Of the above substituted aryl groups, tolyl, t-butylphenyl, dimethylphenyl, (trifluoromethyl)phenyl and bis(trifluoromethyl)phenyl groups are more preferable. Particularly, the substituted phenyl group preferably has the above substituents at the meta and/or para position(s).

When $R^{13}$ is the substituted aryl group, $R^{13}$ and $R^{14}$ may be the same or different.

Q and j are as defined in the formula [I] for the metallocene compound (W).

Examples of the compounds having the above characteristics in the chemical structure include di(p-tolyl)methylene(cyclopentadienyl)(fluorenyl)zirconium dichloride, di(p-tolyl)methylene(cyclopentadienyl)(2,7-di-tert-butylfluorenyl)zirconium dichloride, di(p-tolyl)methylene(cyclopentadienyl)(2,7-dimethylfluorenyl)zirconium dichloride, di(p-tolyl)methylene(cyclopentadienyl)(3,6-di-tert-butylfluorenyl)zirconium dichloride, di(p-tert-butylphenyl)methylene(cyclopentadienyl)(fluorenyl)zirconium dichloride, di(p-tert-butylphenyl)methylene(cyclopentadienyl)(2,7-di-tert-butylfluorenyl)zirconium dichloride, di(p-tert-butylphenyl)methylene(cyclopentadienyl)(2,7-dimethylfluorenyl)zirconium dichloride, di(p-tert-butylphenyl)methylene(cyclopentadienyl)(3,6-di-tert-butylfluorenyl)zirconium dichloride, di(p-n-butylphenyl)methylene(cyclopentadienyl)(fluorenyl)zirconium dichloride, di(p-n-butylphenyl)methylene(cyclopentadienyl)(2,7-di-tert-butylfluorenyl)zirconium dichloride, di(p-n-butylphenyl)methylene(cyclopentadienyl)(2,7-dimethylfluorenyl)zirconium dichloride, di(p-n-butylphenyl)methylene(cyclopentadienyl)(3,6-di-tert-butylfluorenyl)zirconium dichloride, di(m-tolyl)methylene(cyclopentadienyl)(fluorenyl)zirconium dichloride, di(m-tolyl)methylene(cyclopentadienyl)(2,7-di-tert-butylfluorenyl)zirconium dichloride, di(m-tolyl)methylene(cyclopentadienyl)(2,7-dimethylfluorenyl)zirconium dichloride, di(m-tolyl)methylene(cyclopentadienyl)(3,6-di-tert-butylfluorenyl)zirconium dichloride, (p-tolyl)(phenyl)methylene(cyclopentadienyl)(fluorenyl)zirconium dichloride, di(p-isopropylphenyl)methylene(cyclopentadienyl)(fluorenyl)zirconium dichloride, di(p-tert-butylphenyl)methylene(cyclopentadienyl)(fluorenyl)zirconium dichloride, di(p-tolyl)methylene(cyclopentadienyl)(fluorenyl)zirconium dimethyl, di(p-tolyl)methylene(cyclopentadienyl)(octamethyloctahydrodibenzofluorenyl)zirconium dichloride, (p-tolyl)(phenyl)methylene(cyclopentadienyl)(octamethyloctahydrodibenzofluorenyl)zirconium dichloride, di(p-isopropylphenyl)methylene(cyclopentadienyl)(octamethyloctahydrodibenzofluorenyl)zirconium dichloride, di(p-tert-butylphenyl)methylene(cyclopentadienyl)(octamethyloctahydrodibenzofluorenyl)zirconium dichloride, di(p-tolyl)methylene(cyclopentadienyl)(octamethyloctahydrodibenzofluorenyl)zirconium dimethyl, (p-tolyl)(phenyl)methylene(cyclopentadienyl)(2,7-di-tert-butylfluorenyl)zirconium dichloride, di(p-isopropylphenyl)methylene(cyclopentadienyl)(2,7-di-tert-butylfluorenyl)zirconium dichloride, di(p-tert-butylphenyl)methylene(cyclopentadienyl)(2,7-di-tert-butylfluorenyl)zirconium dichloride, di(p-tolyl)methylene(cyclopentadienyl)(2,7-di-tert-butylfluorenyl)zirconium dimethyl, (p-tolyl)(phenyl)methylene(cyclopentadienyl)(3,6-di-tert-butylfluorenyl)zirconium dichloride, di(p-isopropylphenyl)methylene(cyclopentadienyl)(3,6-di-tert-butylfluorenyl)zirconium dichloride, di(p-tert-butylphenyl)methylene(cyclopentadienyl)(3,6-di-tert-butylfluorenyl)zirconium dichloride, di(p-tolyl)methylene(cyclopentadienyl)(3,6-di-tert-butylfluorenyl)zirconium dimethyl, (p-tert-butylphenyl)(phenyl)methylene(cyclopentadienyl)(fluorenyl)zirconium dichloride, (p-tert-butylphenyl)(phenyl)methylene(cyclopentadienyl)(2,7-di-tert-butylfluorenyl)zirconium dichloride, (p-tert-butylphenyl)(phenyl)methylene(cyclopentadienyl)(2,7-dimethylfluorenyl)zirconium dichloride, (p-tert-butylphenyl)(phenyl)methylene(cyclopentadienyl)(3,6-di-tert-butylfluorenyl)zirconium dichloride, (p-ethylphenyl)(phenyl)methylene(cyclopentadienyl)(fluorenyl)zirconium dichloride, (p-ethylphenyl)(phenyl)methylene(cyclopentadienyl)(2,7-di-tert-butylfluorenyl)zirconium dichloride, (p-ethylphenyl)(phenyl)methylene(cyclopentadienyl)(2,7-dimethylfluorenyl)zirconium dichloride, (p-ethylphenyl)(phenyl)methylene(cyclopentadienyl)(3,6-di-tert-butylfluorenyl)zirconium dichloride, (4-biphenyl)(phenyl)methylene(cyclopentadienyl)(fluorenyl)zirconium dichloride, (4-biphenyl)(phenyl)methylene(cyclopentadienyl)(2,7-di-tert-butylfluorenyl)zirconium dichloride, (4-biphenyl)(phenyl)methylene(cyclopentadienyl)(2,7-dimethylfluorenyl)zirconium dichloride, (4-biphenyl)(phenyl)methylene(cyclopentadienyl)(3,6-di-tert-butylfluorenyl)zirconium dichloride, di(4-biphenyl)methylene(cyclopentadienyl)(fluorenyl)zirconium dichloride, di(4-biphenyl)methylene(cyclopentadienyl)(2,7-di-tert-butylfluorenyl)zirconium dichloride, di(4-biphenyl)methylene(cyclopentadienyl)(2,7-dimethylfluorenyl)zirconium dichloride, di(4-biphenyl)methylene(cyclopentadienyl)(3,6-di-tert-butylfluorenyl)zirconium dichloride, bis(3,4-dimethylphenyl)methylene(cyclopentadienyl)(2,7-di-tert-butylfluorenyl)zirconium dichloride, bis(3,4-dimethylphenyl)methylene(cyclopentadienyl)(octamethyloctahydrodibenzofluorenyl)zirconium dichloride, bis(3,5-dimethylphenyl)methylene(cyclopentadienyl)(2,7-di-tert-butylfluorenyl)zirconium dichloride, bis(3,5-dimethylphenyl)methylene(cyclopentadienyl)(octamethyloctahydrodibenzofluorenyl)zirconium dichloride, bis(4-cyclohexylphenyl)methylene(cyclopentadienyl)(2,7-di-tert-butylfluorenyl)zirconium dichloride, bis(4-cyclohexylphenyl)methylene(cyclopentadienyl)(octamethyloctahydrodibenzofluorenyl)zirconium dichloride, bis{3-(trifluoromethyl)phenyl}methylene(cyclopentadienyl)(2,7-di-tert-butylfluorenyl)zirconium dichloride, bis{3-(trifluoromethyl)phenyl}methylene(cyclopentadienyl)(octamethyloctahydrodibenzofluorenyl)zirconium dichloride, bis{3,5-bis(trifluoromethyl)phenyl}methylene(cyclopentadienyl)(2,7-di-tert-butylfluorenyl)zirconium dichloride, and bis{3,5-bis(trifluoromethyl)phenyl}methylene(cyclopentadienyl)(octamethyloctahydrodibenzofluorenyl)zirconium dichloride.

Metallocene Compound (W-2)

The metallocene compound (W-2) is represented by the formula [I-2]:

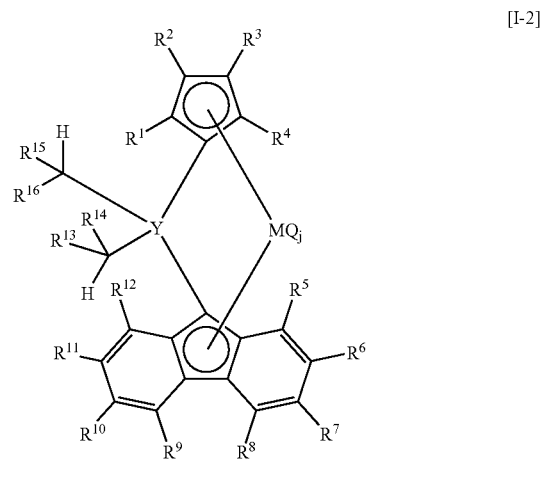

Metallocene compound (W-2)

wherein $R^1$ to $R^{12}$, which may be the same or different, are each hydrogen, a hydrocarbon group or a silicon-containing group. The hydrocarbon group and the silicon-containing group are as defined with respect to the metallocene compound (W).

Neighboring substituents of $R^1$ to $R^4$ may be linked with each other to form a ring. Examples of the substituted cyclopentadienyl group with the ring(s) include indenyl, 2-methylindenyl, tetrahydroindenyl, 2-methyltetrahydroindenyl, 2,2,4-trimethyltetrahydroindenyl, 4-phenylindenyl, 2-methyl-4-phenylindenyl and fluorenyl. In the formula [I-2], $R^1$ to $R^4$ are preferably all hydrogen.

Neighboring substituents of $R^5$ to $R^{12}$ in the fluorene ring may be linked with each other to form a ring. Examples of the substituted fluorenyl group with the ring(s) include benzofluorenyl, dibenzofluorenyl, octahydrodibenzofluorenyl, octamethyloctahydrodibenzofluorenyl and octamethyltetrahydrodicyclopentafluorenyl groups.

Of the substituents $R^5$ to $R^{12}$ in the fluorene ring, arbitrary two or more groups of $R^6$, $R^7$, $R^{10}$ and $R^{11}$ are preferably hydrocarbon groups of 1 to 20 carbon atoms, such as methyl, ethyl, n-propyl, isopropyl, allyl, n-butyl, tert-butyl, amyl and n-pentyl groups. In view of easiness in synthesis of ligands, these substituents are preferably symmetrical, i.e., $R^6$ and $R^{11}$, and $R^7$ and $R^{10}$ are the same groups. It is also preferable that $R^6$ and $R^7$, and $R^{10}$ and $R^{11}$ form the same aliphatic rings.

In the formula [I-2], Y is a carbon atom; $R^{13}$ and $R^{15}$ are each the hydrocarbon group or the silicon-containing group; $R^{14}$ and $R^{16}$ are each hydrogen, the hydrocarbon group or the silicon-containing group; $R^{13}$ and $R^{15}$, and $R^{14}$ and $R^{16}$ may be the same or different; $R^{13}$ and $R^{15}$, and $R^{14}$ and $R^{16}$ may be linked with each other to form rings; when unlinked, $R^{13}$ and $R^{15}$, and $R^{14}$ and $R^{16}$ are preferably the same groups in view of easiness in synthesis of ligands; and $R^{14}$ and $R^{16}$ are preferably hydrogen, more preferably with $R^{13}$ and $R^{15}$ being hydrocarbon groups of 3 to 20 carbon atoms. Examples of the hydrocarbon groups of 3 to 20 carbon atoms include n-propyl, isopropyl, n-butyl, isobutyl, tert-butyl, cyclopentyl, cyclohexyl, cycloheptyl, phenyl, m-tolyl, p-tolyl and benzyl groups. Particularly preferably, $R^{14}$ and $R^{16}$ are both hydrogen and $R^{13}$ and $R^{15}$ are aryl groups of 6 to 20 carbon atoms.

Exemplary aryl groups are phenyl, naphthyl, indenyl, fluorenyl and biphenyl groups, and aromatic nucleus-substituted groups thereof. Phenyl and alkyl-substituted phenyl groups are preferred.

Q and j are as defined in the formula [I] for the metallocene compound (W).

Examples of the metallocene compound (W-2) of the formula [I-2] include di-n-butylmethylene(cyclopentadienyl)(fluorenyl)zirconium dichloride, di-n-butylmethylene(cyclopentadienyl)(2,7-di-tert-butylfluorenyl)zirconium dichloride, di-n-butylmethylene(cyclopentadienyl)(3,6-di-tert-butylfluorenyl)zirconium dichloride, di-n-butylmethylene(cyclopentadienyl)(octamethyloctahydrodibenzofluorenyl)zirconium dichloride, di-n-butylmethylene(cyclopentadienyl)(benzofluorenyl)zirconium dichloride, di-n-butylmethylene(cyclopentadienyl)(dibenzofluorenyl)zirconium dichloride, di-n-butylmethylene(cyclopentadienyl)(octahydrodibenzofluorenyl)zirconium dichloride, di-n-butylmethylene(cyclopentadienyl)(octamethyltetrahydrodicyclopentafluorenyl)zirconium dichloride, diisobutylmethylene(cyclopentadienyl)(fluorenyl)zirconium dichloride, diisobutylmethylene(cyclopentadienyl)(2,7-di-tert-butylfluorenyl)zirconium dichloride, diisobutylmethylene(cyclopentadienyl)(3,6-di-tert-butylfluorenyl)zirconium dichloride, diisobutylmethylene(cyclopentadienyl)(octamethyloctahydrodibenzofluorenyl)zirconium dichloride, diisobutylmethylene(cyclopentadienyl)(benzofluorenyl)zirconium dichloride, diisobutylmethylene(cyclopentadienyl)(dibenzofluorenyl)zirconium dichloride, diisobutylmethylene(cyclopentadienyl)(octahydrodibenzofluorenyl)zirconium dichloride, diisobutylmethylene(cyclopentadienyl)(octamethyltetrahydrodicyclopentafluorenyl)zirconium dichloride, dibenzylmethylene(cyclopentadienyl)(fluorenyl)zirconium dichloride (otherwise, 1,3-diphenylisopropylidene(cyclopentadienyl)(fluorenyl)zirconium dichloride, which will be omitted hereinafter), dibenzylmethylene(cyclopentadienyl)(2,7-di-tert-butylfluorenyl)zirconium dichloride, dibenzylmethylene(cyclopentadienyl)(3,6-di-tert-butylfluorenyl)zirconium dichloride, dibenzylmethylene(cyclopentadienyl)(octamethyloctahydrodibenzofluorenyl)zirconium dichloride, dibenzylmethylene(cyclopentadienyl)(benzofluorenyl)zirconium dichloride, dibenzylmethylene(cyclopentadienyl)(dibenzofluorenyl)zirconium dichloride, dibenzylmethylene(cyclopentadienyl)(octahydrodibenzofluorenyl)zirconium dichloride, dibenzylmethylene(cyclopentadienyl)(octamethyltetrahydrodicyclopentafluorenyl)zirconium dichloride, diphenethylmethylene(cyclopentadienyl)(fluorenyl)zirconium dichloride, diphenethylmethylene(cyclopentadienyl)(2,7-di-tert-butylfluorenyl)zirconium dichloride, diphenethylmethylene(cyclopentadienyl)(3,6-di-tert-butylfluorenyl)zirconium dichloride, diphenethylmethylene(cyclopentadienyl)(octamethyloctahydrodibenzofluorenyl)zirconium dichloride, diphenethylmethylene(cyclopentadienyl)(benzofluorenyl)zirconium dichloride, diphenethylmethylene(cyclopentadienyl)(dibenzofluorenyl)zirconium dichloride, diphenethylmethylene(cyclopentadienyl)(octahydrodibenzofluorenyl)zirconium dichloride, diphenethylmethylene(cyclopentadienyl)(octamethyltetrahydrodicyclopentafluorenyl)zirconium dichloride, di(benzhydryl)methylene(cyclopentadienyl)(fluorenyl)zirconium dichloride, di(benzhydryl)methylene(cyclopentadienyl)(2,7-di-tert-butylfluorenyl)zirconium dichloride, di(benzhydryl)methylene(cyclopentadienyl)(3,6-di-tert-butylfluorenyl)zirconium dichloride, di(benzhydryl)methylene(cyclopentadienyl)(octamethyloctahydrodibenzofluorenyl)zirconium dichloride, di(benzhydryl)methylene(cyclopentadienyl)(benzofluorenyl)zirconium dichloride, di(benzhydryl)methylene(cyclopentadienyl)(dibenzofluorenyl)zirconium dichloride, di(benzhydryl)methylene(cyclopentadienyl)(octahydrodibenzofluorenyl)zirconium dichloride, di(benzhydryl)methylene(cyclopentadienyl)(octamethyltetrahydrodicyclopentafluorenyl)zirconium dichloride, di(cumyl)methylene(cyclopentadienyl)(fluorenyl)zirconium dichloride, di(cumyl)methylene(cyclopentadienyl)(2,7-di-tert-butylfluorenyl)zirconium dichloride, di(cumyl)methylene(cyclopentadienyl)(3,6-di-tert-butylfluorenyl)zirconium dichloride, di(cumyl)methylene(cyclopentadienyl)(octamethyloctahydrodibenzofluorenyl)zirconium dichloride, di(cumyl)methylene(cyclopentadienyl)(benzofluorenyl)zirconium dichloride, di(cumyl)methylene(cyclopentadienyl)(dibenzofluorenyl)zirconium dichloride, di(cumyl)methylene(cyclopentadienyl)(octahydrodibenzofluorenyl)zirconium dichloride, di(cumyl)methylene(cyclopentadienyl)(octamethyltetrahydrodicyclopentafluorenyl)zirconium dichloride, di(1-phenyl-ethyl)methylene(cyclopentadienyl)(fluorenyl)zirconium dichloride, di(1-phenyl-ethyl)methylene(cyclopentadienyl)(2,7-di-tert-butylfluorenyl)zirconium dichloride, di(1-phenyl-ethyl)methylene(cyclopentadienyl)(3,6-di-tert-butylfluorenyl)zirconium dichloride, di(1-phenyl-ethyl)methylene(cyclopentadienyl)(octamethyloctahydrodibenzofluorenyl)zirconium dichloride, di(1-phenyl-ethyl)methylene(cyclopentadienyl)(benzofluorenyl)zirconium dichloride, di(1-phenyl-ethyl)methylene(cyclopentadienyl)(dibenzofluorenyl)zirconium dichloride, di(1-phenyl-ethyl)methylene(cyclopentadienyl)(octahydrodibenzofluorenyl)zirconium dichloride, di(1-phenyl-ethyl)methylene(cyclopentadienyl)(octamethyltetrahydrodicyclopentafluorenyl)zirconium dichloride, di(cyclohexylmethyl)methylene(cyclopentadienyl)(fluorenyl)zirconium dichloride, di(cyclohexylmethyl)methylene(cyclopentadienyl)(2,7-di-tert-butylfluorenyl)zirconium dichloride, di(cyclohexylmethyl)methylene(cyclopentadienyl)(3,6-di-tert-butylfluorenyl)zirconium dichloride, di(cyclohexylmethyl)methylene(cyclopentadienyl)(octamethyloctahydrodibenzofluorenyl)zirconium dichloride, di(cyclohexylmethyl)methylene(cyclopentadienyl)(benzofluorenyl)zirconium dichloride, di(cyclohexylmethyl)methylene(cyclopentadienyl)(dibenzofluorenyl)zirconium dichloride, di(cyclohexylmethyl)methylene(cyclopentadienyl)(octahydrodibenzofluorenyl)zirconium dichloride, di(cyclohexylmethyl)methylene(cyclopentadienyl)(octamethyltetrahydrodicyclopentafluorenyl)zirconium dichloride, di(1-cyclohexyl-ethyl)methylene(cyclopentadienyl)(fluorenyl)zirconium dichloride, di(1-cyclohexyl-ethyl)methylene(cyclopentadienyl)(2,7-di-tert-butylfluorenyl)zirconium dichloride, di(1-cyclohexyl-ethyl)methylene(cyclopentadienyl)(3,6-di-tert-butylfluorenyl)zirconium dichloride, di(1-cyclohexyl-ethyl)methylene(cyclopentadienyl)(octamethyloctahydrodibenzofluorenyl)zirconium dichloride, di(1-cyclohexyl-ethyl)methylene(cyclopentadienyl)(benzofluorenyl)zirconium dichloride, di(1-cyclohexyl-ethyl)methylene(cyclopentadienyl)(dibenzofluorenyl)zirconium dichloride, di(1-cyclohexyl-ethyl)methylene(cyclopentadienyl)(octahydrodibenzofluorenyl)zirconium dichloride, di(1-cyclohexyl-ethyl)methylene(cyclopentadienyl)(octamethyltetrahydrodicyclopentafluorenyl)zirconium dichloride, di(cyclopentylmethyl)methylene(cyclopentadienyl)(fluorenyl)zirconium dichloride, di(cyclopentylmethyl)methylene(cyclopentadienyl)(2,7-di-tert-butylfluorenyl)zirconium dichloride, di(cyclopentylmethyl)methylene(cyclopentadienyl)(3,6-di-tert-butylfluorenyl)zirconium dichloride, di(cyclopentylmethyl)methylene(cyclopentadienyl)(octamethyloctahydrodibenzofluorenyl)zirconium dichloride, di(cyclopentylmethyl)methylene(cyclopentadienyl)(benzofluorenyl)zirconium dichloride, di(cyclopentylmethyl)methylene(cyclopentadienyl)(dibenzofluorenyl)zirconium dichloride, di(cyclopentylmethyl)methylene(cyclopentadienyl)(octahydrodibenzofluorenyl)zirconium dichloride, di(cyclopentylmethyl)methylene(cyclopentadienyl)(octamethyltetrahydrodicyclopentafluorenyl)zirconium dichloride, di(1-cyclopentyl-ethyl)methylene(cyclopentadienyl)(fluorenyl)zirconium dichloride, di(1-cyclopentyl-ethyl)methylene(cyclopentadienyl)(2,7-di-tert-butylfluorenyl)zirconium dichloride, di(1-cyclopentyl-ethyl)methylene(cyclopentadienyl)(3,6-di-tert-butylfluorenyl)zirconium dichloride, di(1-cyclopentyl-ethyl)methylene(cyclopentadienyl)(octamethyloctahydrodibenzofluorenyl)zirconium dichloride, di(1-cyclopentyl-ethyl)methylene(cyclopentadienyl)(benzofluorenyl)zirconium dichloride, di(1-cyclopentyl-ethyl)methylene(cyclopentadienyl)(dibenzofluorenyl)zirconium dichloride, di(1-cyclopentyl-ethyl)methylene(cyclopentadienyl)(octahydrodibenzofluorenyl)zirconium dichloride, di(1-cyclopentyl-ethyl)methylene(cyclopentadienyl)(octamethyltetrahydrodicyclopentafluorenyl)zirconium dichloride, di(naphthylmethyl)methylene(cyclopentadienyl)(fluorenyl)zirconium dichloride, di(naphthylmethyl)methylene(cyclopentadienyl)(2,7-di-tert-butylfluorenyl)zirconium dichloride, di(naphthylmethyl)methylene(cyclopentadienyl)(3,6-di-tert-butylfluorenyl)zirconium dichloride, di(naphthylmethyl)methylene(cyclopentadienyl)(octamethyloctahydrodibenzofluorenyl)zirconium dichloride, di(naphthylmethyl)methylene(cyclopentadienyl)(benzofluorenyl)zirconium dichloride, di(naphthylmethyl)methylene(cyclopentadienyl)(dibenzofluorenyl)zirconium dichloride, di(naphthylmethyl)methylene(cyclopentadienyl)(octahydrodibenzofluorenyl)zirconium dichloride, di(naphthylmethyl)methylene(cyclopentadienyl)(octamethyltetrahydrodicyclopentafluorenyl)zirconium dichloride, di(biphenylmethyl)methylene(cyclopentadienyl)(fluorenyl)zirconium dichloride, di(biphenylmethyl)methylene(cyclopentadienyl)(2,7-di-tert-butylfluorenyl)zirconium dichloride, di(biphenylmethyl)methylene(cyclopentadienyl)(3,6-di-tert-butylfluorenyl)zirconium dichloride, di(biphenylmethyl)methylene(cyclopentadienyl)(octamethyloctahydrodibenzofluorenyl)zirconium dichloride, di(biphenylmethyl)methylene(cyclopentadienyl)(benzofluorenyl)zirconium dichloride, di(biphenylmethyl)methylene(cyclopentadienyl)(dibenzofluorenyl)zirconium dichloride, di(biphenylmethyl)methylene(cyclopentadienyl)(octahydrodibenzofluorenyl)zirconium dichloride, di(biphenylmethyl)methylene(cyclopentadienyl)(octamethyltetrahydrodicyclopentafluorenyl)zirconium dichloride, (benzyl)(phenethyl)methylene(cyclopentadienyl)(fluorenyl)zirconium dichloride, (benzyl)(phenethyl)methylene(cyclopentadienyl)(2,7-di-tert-butylfluorenyl)zirconium dichloride, (benzyl)(phenethyl)methylene(cyclopentadienyl)(3,6-di-tert-butylfluorenyl)zirconium dichloride, (benzyl)(phenethyl)methylene(cyclopentadienyl)(octamethyloctahydrodibenzofluorenyl)zirconium dichloride, (benzyl)(n-butyl)methylene(cyclopentadienyl)(fluorenyl)zirconium dichloride, (benzyl)(n-butyl)methylene(cyclopentadienyl)(2,7-di-tert-butylfluorenyl)zirconium dichloride, (benzyl)(n-butyl)methylene(cyclopentadienyl)(3,6-di-tert-butylfluorenyl)zirconium dichloride, (benzyl)(n-butyl)methylene(cyclopentadienyl)(octamethyloctahydrodibenzofluorenyl)zirconium dichloride, (benzyl)(cumyl)methylene(cyclopentadienyl)(fluorenyl)zirconium dichloride, (benzyl)(cumyl)methylene(cyclopentadienyl)(2,7-di-tert-butylfluorenyl)zirconium dichloride, (benzyl)(cumyl)methylene(cyclopentadienyl)(3,6-di-tert-butylfluorenyl)zirconium dichloride, (benzyl)(cumyl)methylene(cyclopentadienyl)(octamethyloctahydrodibenzofluorenyl)zirconium dichloride, (benzyl)(cyclohexylmethyl)methylene(cyclopentadienyl)(fluorenyl)zirconium dichloride, (benzyl)(cyclohexylmethyl)methylene(cyclopentadienyl)(2,7-di-tert-butylfluorenyl)zirconium dichloride, (benzyl)(cyclohexylmethyl)methylene(cyclopentadienyl)(3,6-di-tert-butylfluorenyl)zirconium dichloride, (benzyl)(cyclohexylmethyl)methylene(cyclopentadienyl)(octamethyloctahydrodibenzofluorenyl)zirconium dichloride, dibenzylmethylene(cyclopentadienyl)(fluorenyl)titanium dichloride, dibenzylmethylene(cyclopentadienyl)(2,7-di-tert-butylfluorenyl)titanium dichloride, dibenzylmethylene(cyclopentadienyl)(3,6-di-tert-butylfluorenyl)titanium dichloride, dibenzylmethylene(cyclopentadienyl)(octamethyloctahydrodibenzofluorenyl)titanium dichloride, dibenzylmethylene(cyclopentadienyl)(fluorenyl)hafnium dichloride, dibenzylmethylene(cyclopentadienyl)(2,7-di-tert-butylfluorenyl)hafnium dichloride, dibenzylmethylene(cyclopentadienyl)(3,6-di-tert-butylfluorenyl)hafnium dichloride, dibenzylmethylene(cyclopentadienyl)(octamethyloctahydrodibenzofluorenyl)hafnium dichloride, dibenzylmethylene(cyclopentadienyl)(fluorenyl)zirconium dibromide, dibenzylmethylene(cyclopentadienyl)(2,7-di-tert-butylfluorenyl)zirconium dibromide, dibenzylmethylene(cyclopentadienyl)(3,6-di-tert-butylfluorenyl)zirconium dibromide, dibenzylmethylene(cyclopentadienyl)(octamethyloctahydrodibenzofluorenyl)zirconium dibromide, dibenzylmethylene(cyclopentadienyl)(fluorenyl)zirconium dimethyl, dibenzylmethylene(cyclopentadienyl)(2,7-di-tert-butylfluorenyl)zirconium dimethyl, dibenzylmethylene(cyclopentadienyl)(3,6-di-tert-butylfluorenyl)zirconium dimethyl, dibenzylmethylene(cyclopentadienyl)(octamethyloctahydrodibenzofluorenyl)zirconium dimethyl, dicyclohexylmethylene(cyclopentadienyl)(fluorenyl)zirconium dichloride, dicyclohexylmethylene(cyclopentadienyl)(2,7-di-tert-butylfluorenyl)zirconium dichloride, dicyclohexylmethylene(cyclopentadienyl)(3,6-di-tert-butylfluorenyl)zirconium dichloride, dicyclohexylmethylene(cyclopentadienyl)(octamethyloctahydrodibenzofluorenyl)zirconium dichloride, (cyclohexyl)(methyl)methylene(cyclopentadienyl)(fluorenyl)zirconium dichloride, (cyclohexyl)(methyl)methylene(cyclopentadienyl)(2,7-di-tert-butylfluorenyl)zirconium dichloride, (cyclohexyl)(methyl)methylene(cyclopentadienyl)(3,6-di-tert-butylfluorenyl)zirconium dichloride, (cyclohexyl)(methyl)methylene(cyclopentadienyl)(octamethyloctahydrodibenzofluorenyl)zirconium dichloride, (adamantyl)(methyl)methylene(cyclopentadienyl)(fluorenyl)zirconium dichloride, (adamantyl)(methyl)methylene(cyclopentadienyl)(2,7-di-tert-butylfluorenyl)zirconium dichloride, (adamantyl)(methyl)methylene(cyclopentadienyl)(3,6-di-tert-butylfluorenyl)zirconium dichloride, and (adamantyl)(methyl)methylene(cyclopentadienyl)(octamethyloctahydrodibenzofluorenyl)zirconium dichloride.

Metallocene compound (W-3)

The metallocene compound (W-3) is represented by the formula [I-3]:

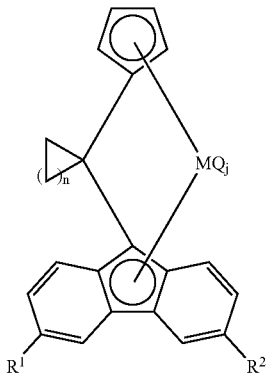

[I-3]

Metallocene compound (W-3)

wherein $R^1$ and $R^2$, which may be the same or different, are each hydrogen, a hydrocarbon group, a silicon-containing group or a halogen-containing group, preferably both hydrocarbon groups. The hydrocarbon group and the silicon-containing group are as defined with respect to the metallocene compound (W). Examples of the halogen-containing group include fluorine, chlorine, bromine and iodine atoms, and a trifluoromethyl group.

The hydrocarbon group is preferably a methyl, ethyl, n-propyl, isopropyl, n-butyl, isobutyl, tert-butyl, cyclopentyl, cyclohexyl, cycloheptyl, phenyl, m-tolyl, p-tolyl, benzyl or cumyl group, particularly a methyl, tert-butyl, phenyl or cumyl group, optimally a tert-butyl group.

n is an integer from 1 to 10, preferably 3 or 4.

Q and j are as defined in the formula [I] for the metallocene compound (W).

Examples of the metallocene compound (W-3) of the formula [I-3] include cyclopropylidene(cyclopentadienyl)(3,6-dimethyl-fluorenyl)zirconium dichloride, cyclobutylidene(cyclopentadienyl)(3,6-dimethyl-fluorenyl)zirconium dichloride, cyclopentylidene(cyclopentadienyl)(3,6-dimethyl-fluorenyl)zirconium dichloride, cyclohexylidene(cyclopentadienyl)(3,6-dimethyl-fluorenyl)zirconium dichloride, cycloheptylidene(cyclopentadienyl)(3,6-dimethyl-fluorenyl)zirconium dichloride, cyclopropylidene(cyclopentadienyl)(3,6-di-tert-butylfluorenyl)zirconium dichloride, cyclobutylidene(cyclopentadienyl)(3,6-di-tert-butylfluorenyl)zirconium dichloride, cyclopentylidene(cyclopentadienyl)(3,6-di-tert-butylfluorenyl) zirconium dichloride, cyclohexylidene(cyclopentadienyl)(3,6-di-tert-butylfluorenyl)zirconium dichloride, cycloheptylidene(cyclopentadienyl)(3,6-di-tert-butylfluorenyl)zirconium dichloride, cyclopropylidene(cyclopentadienyl)(3,6-dicumyl-fluorenyl)zirconium dichloride, cyclobutylidene(cyclopentadienyl)(3,6-dicumyl-fluorenyl)zirconium dichloride, cyclopentylidene(cyclopentadienyl)(3,6-dicumyl-fluorenyl)zirconium dichloride, cyclohexylidene(cyclopentadienyl)(3,6-dicumyl-fluorenyl)zirconium dichloride, cycloheptylidene(cyclopentadienyl)(3,6-dicumyl-fluorenyl)zirconium dichloride, cyclopropylidene(cyclopentadienyl)(3,6-di(trimethylsilyl)-fluorenyl)zirconium dichloride, cyclobutylidene(cyclopentadienyl)(3,6-di(trimethylsilyl)-fluorenyl)zirconium dichloride, cyclopentylidene(cyclopentadienyl)(3,6-di(trimethylsilyl)-fluorenyl)zirconium dichloride, cyclohexylidene(cyclopentadienyl)(3,6-di(trimethylsilyl)-fluorenyl)zirconium dichloride, cycloheptylidene(cyclopentadienyl)(3,6-di(trimethylsilyl)-fluorenyl)zirconium dichloride, cyclopropylidene(cyclopentadienyl)(3,6-diphenyl-fluorenyl)zirconium dichloride, cyclobutylidene(cyclopentadienyl)(3,6-diphenyl-fluorenyl)zirconium dichloride, cyclopentylidene(cyclopentadienyl)(3,6-diphenyl-fluorenyl) zirconium dichloride, cyclohexylidene(cyclopentadienyl)(3,6-diphenyl-fluorenyl)zirconium dichloride, cycloheptylidene(cyclopentadienyl)(3,6-diphenyl-fluorenyl) zirconium dichloride, cyclopropylidene(cyclopentadienyl)(3,6-dibenzyl-fluorenyl)zirconium dichloride, cyclobutylidene(cyclopentadienyl)(3,6-dibenzyl-fluorenyl)zirconium dichloride, cyclopentylidene(cyclopentadienyl)(3,6-dibenzyl-fluorenyl)zirconium dichloride, cyclohexylidene(cyclopentadienyl)(3,6-dibenzyl-fluorenyl)zirconium dichloride, cycloheptylidene(cyclopentadienyl)(3,6-dibenzyl-fluorenyl)zirconium dichloride, cyclopropylidene(cyclopentadienyl)(3,6-difluorofluorenyl)zirconium dichloride, cyclobutylidene(cyclopentadienyl)(3,6-difluorofluorenyl)zirconium dichloride, cyclopentylidene(cyclopentadienyl)(3,6-difluorofluorenyl)zirconium dichloride, cyclohexylidene(cyclopentadienyl)(3,6-difluorofluorenyl)zirconium dichloride, cycloheptylidene(cyclopentadienyl)(3,6-difluorofluorenyl) zirconium dichloride, cyclopropylidene(cyclopentadienyl)(3,6-dibromofluorenyl)zirconium dichloride, cyclobutylidene(cyclopentadienyl)(3,6-dibromofluorenyl)zirconium dichloride, cyclopentylidene(cyclopentadienyl)(3,6-dibromofluorenyl)zirconium dichloride, cyclohexylidene(cyclopentadienyl)(3,6-dibromofluorenyl)zirconium dichloride, cycloheptylidene(cyclopentadienyl)(3,6-dibromofluorenyl) zirconium dichloride, cyclopropylidene(cyclopentadienyl)(3,6-di-tert-butylfluorenyl)zirconium dibromide, cyclobutylidene(cyclopentadienyl)(3,6-di-tert-butylfluorenyl) zirconium dibromide, cyclopentylidene(cyclopentadienyl)(3,6-di-tert-butylfluorenyl)zirconium dibromide, cyclohexylidene(cyclopentadienyl)(3,6-di-tert-butylfluorenyl)zirconium dibromide, cycloheptylidene(cyclopentadienyl)(3,6-di-tert-butylfluorenyl)zirconium dibromide, cyclopropylidene(cyclopentadienyl)(3,6-dimethyl-fluorenyl) zirconium dimethyl, cyclobutylidene(cyclopentadienyl)(3,6-dimethyl-fluorenyl)zirconium dimethyl, cyclopentylidene(cyclopentadienyl)(3,6-dimethyl-fluorenyl)zirconium dimethyl, cyclohexylidene(cyclopentadienyl)(3,6-dimethyl-fluorenyl)zirconium dimethyl, cycloheptylidene(cyclopentadienyl)(3,6-dimethyl-fluorenyl)zirconium dimethyl, cyclopropylidene(cyclopentadienyl)(3,6-di-tert-butylfluorenyl) hafnium dichloride, cyclobutylidene(cyclopentadienyl)(3,6-di-tert-butylfluorenyl)hafnium dichloride, cyclopentylidene(cyclopentadienyl)(3,6-di-tert-butylfluorenyl)hafnium dichloride, cyclohexylidene(cyclopentadienyl)(3,6-di-tert-butylfluorenyl)hafnium dichloride, cycloheptylidene(cyclopentadienyl)(3,6-di-tert-butylfluorenyl)titanium dichloride, cyclopropylidene(cyclopentadienyl)(3,6-di-tert-butylfluorenyl)titanium dichloride, cyclobutylidene(cyclopentadienyl)(3,6-di-tert-butylfluorenyl)titanium dichloride, cyclopentylidene(cyclopentadienyl)(3,6-di-tert-butylfluorenyl)titanium dichloride, cyclohexylidene(cyclopentadienyl)(3,6-di-tert-butylfluorenyl)titanium dichloride, and cycloheptylidene(cyclopentadienyl)(3,6-di-tert-butylfluorenyl)titanium dichloride.

Metallocene Compound (W-4)

The metallocene compound (W-4) is represented by the formula [I-4]:

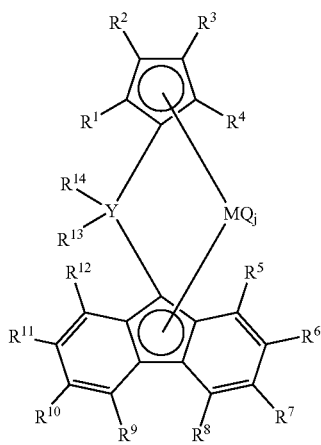
[I-4]

wherein $R^1$ to $R^{14}$, which may be the same or different, are each hydrogen, a hydrocarbon group or a silicon-containing group; and $R^{13}$ and $R^{14}$ may be linked with other to form a ring. The hydrocarbon group and the silicon-containing group are as defined with respect to the metallocene compound (W). In the formula [I-4], $R^1$ to $R^4$ are preferably all hydrogen.

In the fluorenyl ligands of the bridged metallocene compound (W-4) of the formula [I-4], arbitrary three or more substituents of $R^5$ to $R^{12}$, especially $R^6$, $R^7$, $R^{10}$ and $R^{11}$, are preferably hydrocarbon groups and/or silicon-containing groups. In particular, $R^6$ and $R^7$, and $R^{10}$ and $R^{11}$ are preferably linked with each other to form rings. The two rings may be the same or different. For example, the fluorenyl ligands are represented by the following formulae [I-4-1] and [I-4-2]:

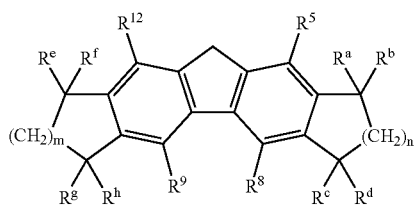
[I-4-1]

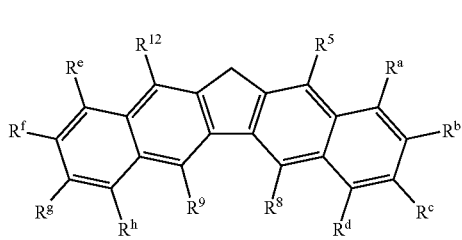
[I-4-2]

wherein $R^5$, $R^8$, $R^9$ and $R^{12}$ are as defined in the formula [I-4]; $R^a$ to $R^h$ are each hydrogen or an alkyl group of 1 to 5 carbon atoms, such as methyl, ethyl, n-propyl, isopropyl, n-butyl, t-butyl, amyl or n-pentyl group. In the formula [I-4-1], m and n are integers from 1 to 3 and may be the same or different, preferably m=n=1 or m=n=2.

The cyclopentadienyl ligands and the fluorenyl ligands are linked by a covalent bond of carbon atoms Y. Specifically, the linkage is made by saturated hydrocarbon groups of 2 to 20 carbon atoms, such as —CH$_2$—, —CH (CH$_3$)—, —C (CH$_3$)$_2$—, cyclohexylidene and cyclohexylene groups, or unsaturated hydrocarbon groups of 6 to 20 carbon atoms, such as —CH(C$_6$H$_5$)—, —C(CH$_3$) (C$_6$H$_5$)— and —C (C$_6$H$_5$)$_2$—.

Q and j are as defined in the formula [I] for the metallocene compound (W).

Preferable metallocene compounds (W-4) include octamethyloctahydrodibenzofluorene of the formula [I-4-3], octamethyltetrahydrodicyclopentafluorene of the formula [I-4-4] and dibenzofluorene of the formula [I-4-5] given below:

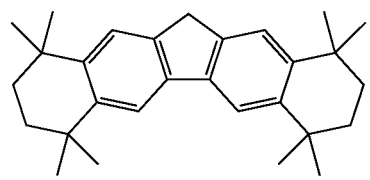
[I-4-3]

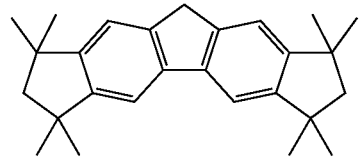
[I-4-4]

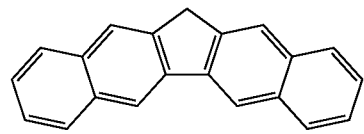
[I-4-5]

Examples of the compounds having the above characteristics in the chemical structure include cyclopentylidene(cyclopentadienyl)(octamethyloctahydrodibenzofluorenyl)zirconium dichloride, cyclohexylidene(cyclopentadienyl)(octamethyloctahydrodibenzofluorenyl)zirconium dichloride, adamantylidene(cyclopentadienyl)(octamethyloctahydrodibenzofluorenyl)zirconium dichloride, monophenylmonomethylmethylene(cyclopentadienyl)(octamethyloctahydrodibenzofluorenyl)zirconium dichloride, dimethylmethylene(cyclopentadienyl)(octamethyloctahydrodibenzofluorenyl)zirconium dichloride, diphenylmethylene(cyclopentadienyl)(octamethyloctahydrodibenzofluorenyl)zirconium dichloride, di(p-tolyl)methylene(cyclopentadienyl)(octamethyloctahydrodibenzofluorenyl)zirconium dichloride, diethylmethylene(cyclopentadienyl)(octamethyloctahydrodibenzofluorenyl)zirconium dichloride, cyclopentylidene(cyclopentadienyl)(octamethyltetrahydrodicyclopentafluorenyl)zirconium dichloride, cyclohexylidene(cyclopentadienyl)(octamethyltetrahydrodicyclopentafluorenyl)zirconium dichloride, adamantylidene(cyclopentadienyl)(octamethyltetrahydrodicyclopentafluorenyl)zirconium dichloride, monophenylmonomethylmethylene(cyclopentadienyl)(octamethyltetrahydrodicyclopentafluorenyl)zirconium dichloride, dimethylmethylene(cyclopentadienyl)(octamethyltetrahydrodicyclopentafluorenyl)zirconium dichloride, diphenylmethylene(cyclopentadienyl)(octamethyltetrahydrodicyclopentafluorenyl)zirconium dichloride, di(p-tolyl)methylene(cyclopentadienyl)(octamethyltetrahydrodicyclopentafluorenyl)zirconium dichloride, diethylmethylene(cyclopentadienyl)octamethyltetrahydrodicyclopentafluorenyl)zirconium dichloride, cyclopentylidene(cyclopentadienyl)(dibenzofluorenyl)zirconium dichloride, cyclohexylidene(cyclopentadienyl)(dibenzofluorenyl)zirconium dichloride, adamantylidene(cyclopentadienyl)(dibenzofluorenyl)zirconium dichloride, monophenylmonomethylmethylene(cyclopentadienyl)(dibenzofluorenyl)zirconium dichloride, dimethylmethylene(cyclopentadienyl)(dibenzofluorenyl)zirconium dichloride, diphenylmethylene(cyclopentadienyl)(dibenzofluorenyl)zirconium dichloride, di(p-tolyl)methylene(cyclopentadienyl)(dibenzofluorenyl)zirconium dichloride, diethylmethylene(cyclopentadienyl)(dibenzofluorenyl)zirconium dichloride, cyclopentylidene(cyclopentadienyl)(octamethyloctahydrodibenzofluorenyl)hafnium dichloride, cyclohexylidene(cyclopentadienyl)(octamethyloctahydrodibenzofluorenyl)hafnium dichloride, adamantylidene(cyclopentadienyl)(octamethyloctahydrodibenzofluorenyl)hafnium dichloride, monophenylmonomethylmethylene(cyclopentadienyl)(octamethyloctahydrodibenzofluorenyl)hafnium dichloride, dimethylmethylene(cyclopentadienyl)(octamethyloctahydrodibenzofluorenyl)hafnium dichloride, diphenylmethylene(cyclopentadienyl)(octamethyloctahydrodibenzofluorenyl)hafnium dichloride, di(p-tolyl)methylene(cyclopentadienyl)(octamethyloctahydrodibenzofluorenyl)hafnium dichloride, diethylmethylene(cyclopentadienyl)(octamethyloctahydrodibenzofluorenyl)hafnium dichloride, cyclopentylidene(cyclopentadienyl)(octamethyloctahydrodibenzofluorenyl)titanium dichloride, cyclohexylidene(cyclopentadienyl)(octamethyloctahydrodibenzofluorenyl)titanium dichloride, adamantylidene(cyclopentadienyl)(octamethyloctahydrodibenzofluorenyl)titanium dichloride, monophenylmonomethylmethylene(cyclopentadienyl)(octamethyloctahydrodibenzofluorenyl)titanium dichloride, dimethylmethylene(cyclopentadienyl)(octamethyloctahydrodibenzofluorenyl)titanium dichloride, diphenylmethylene(cyclopentadienyl)(octamethyloctahydrodibenzofluorenyl)titanium dichloride, di(p-tolyl)methylene(cyclopentadienyl)(octamethyloctahydrodibenzofluorenyl)titanium dichloride, and diethylmethylene(cyclopentadienyl)(octamethyloctahydrodibenzofluorenyl)titanium dichloride.

Metallocene Compound (W-5)

The metallocene compound (W-5) is represented by the formula [I-5]:

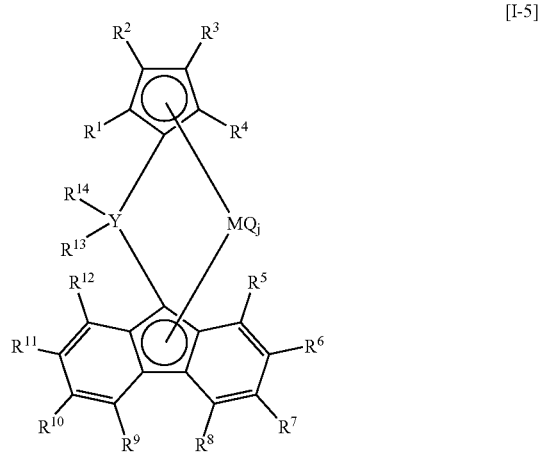

[I-5]

wherein $R^1$ to $R^{12}$, which may be the same or different, are each hydrogen, a hydrocarbon group or a silicon-containing group. The hydrocarbon group and the silicon-containing group are as defined with respect to the metallocene compound (W).

Neighboring substituents of $R^1$ to $R^4$ may be linked with each other to form a ring. Examples of the substituted cyclopentadienyl group include indenyl, 2-methylindenyl, tetrahydroindenyl, 2-methyltetrahydroindenyl, 2,2,4-trimethyltetrahydroindenyl, 4-phenylindenyl, 2-methyl-4-phenylindenyl and fluorenyl groups. Neighboring substituents of $R^5$ to $R^{12}$ in the fluorene ring may be linked with each other to form a ring. Examples of the substituted fluorenyl group include benzofluorenyl, dibenzofluorenyl, octahydrodibenzofluorenyl and octamethyloctahydrodibenzofluorenyl groups.

In view of enhancement of polymerization activity, reactivity with hydrogen as a molecular weight modifier, easy synthesis of the metallocene compound and thus reduction in production cost of the metallocene compound, $R^1$ to $R^4$ in the formula [I-5] are preferably all hydrogen.

From the viewpoints of enhancement of polymerization activity and larger molecular weights of resultant polyolefins, arbitrary two or more substituents of $R^6$, $R^7$, $R^{10}$ and $R^{11}$ in the fluorene ring in the formula [I-5] are preferably hydrocarbon groups of 1 to 10 carbon atoms, such as methyl, ethyl, n-propyl, isopropyl, allyl, n-butyl, tert-butyl, amyl and n-pentyl groups. In view of easiness in synthesis of ligands, these substituents are preferably symmetrical, i.e., $R^6$ and $R^{11}$, and $R^7$ and $R^{10}$ are the same groups. It is also preferable that $R^6$ and $R^7$, and $R^{10}$ and $R^{11}$ form the same aliphatic rings.

In the formula [I-5], Y is a silicon, germanium or tin atom; the two substituents $R^{13}$ and $R^{14}$ linked with Y are the above hydrocarbon groups and may be linked with each other to form a ring; and $R^{13}$ and $R^{14}$ may be the same or different, preferably the same in view of easiness in synthesis of ligands. Of the above hydrocarbon groups, methyl, ethyl, n-propyl, isopropyl, n-butyl, isobutyl, tert-butyl, cyclopentyl, cyclohexyl, cycloheptyl, phenyl, m-tolyl and p-tolyl groups are preferred, and particularly methyl, phenyl and cyclohexyl groups are preferred.

Q and j are as defined in the formula [I] for the metallocene compound (W).

Preferred examples of the metallocene compound (W-5) include dimethylsilylene(cyclopentadienyl)(fluorenyl)zirconium dichloride, dimethylsilylene(cyclopentadienyl)(2,7-dimethylfluorenyl)zirconium dichloride, dimethylsilylene(cyclopentadienyl)(3,6-di-tert-butylfluorenyl)zirconium dichloride, dimethylsilylene(cyclopentadienyl)(octamethyloctahydrodibenzofluorenyl)zirconium dichloride, dimethylsilylene(cyclopentadienyl)(fluorenyl)zirconium dimethyl, dimethylsilylene(cyclopentadienyl)(2,7-dimethylfluorenyl)zirconium dimethyl, dimethylsilylene(cyclopentadienyl)(3,6-di-tert-butylfluorenyl)zirconium dimethyl, dimethylsilylene(cyclopentadienyl)(octamethyloctahydrodibenzofluorenyl)zirconium dimethyl, diethylsilylene(cyclopentadienyl)(fluorenyl)zirconium dichloride, diethylsilylene(cyclopentadienyl)(2,7-di-tert-butylfluorenyl)zirconium dichloride, diethylsilylene(cyclopentadienyl)(2,7-dimethylfluorenyl)zirconium dichloride, diethylsilylene(cyclopentadienyl)(3,6-di-tert-butylfluorenyl)zirconium dichloride, diethylsilylene(cyclopentadienyl)(octamethyloctahydrodibenzofluorenyl)zirconium dichloride, diethylsilylene(cyclopentadienyl)(fluorenyl)zirconium dimethyl, diethylsilylene(cyclopentadienyl)(2,7-di-tert-butylfluorenyl)zirconium dimethyl, diethylsilylene(cyclopentadienyl)(2,7-dimethylfluorenyl)zirconium dimethyl, diethylsilylene(cyclopentadienyl)(3,6-di-tert-butylfluorenyl)zirconium dimethyl, diethylsilylene(cyclopentadienyl)(octamethyloctahydrodibenzofluorenyl)zirconium dimethyl, di-n-propylsilylene(cyclopentadienyl)(fluorenyl)zirconium dichloride, di-n-propylsilylene(cyclopentadienyl)(2,7-di-tert-butylfluorenyl)zirconium dichloride, di-n-propylsilylene(cyclopentadienyl)(2,7-dimethylfluorenyl)zirconium dichloride, di-n-propylsilylene(cyclopentadienyl)(3,6-di-tert-butylfluorenyl)zirconium dichloride, di-n-propylsilylene(cyclopentadienyl)(octamethyloctahydrodibenzofluorenyl)zirconium dichloride, di-n-propylsilylene(cyclopentadienyl)(fluorenyl)zirconium dimethyl, di-n-propylsilylene(cyclopentadienyl)(2,7-di-tert-butylfluorenyl)zirconium dimethyl, di-n-propylsilylene(cyclopentadienyl)(2,7-dimethylfluorenyl)zirconium dimethyl, di-n-propylsilylene(cyclopentadienyl)(3,6-di-tert-butylfluorenyl)zirconium dimethyl, di-n-propylsilylene(cyclopentadienyl)(octamethyloctahydrodibenzofluorenyl)zirconium dimethyl, diisopropylsilylene(cyclopentadienyl)(fluorenyl)zirconium dichloride, diisopropylsilylene(cyclopentadienyl)(2,7-di-tert-butylfluorenyl)zirconium dichloride, diisopropylsilylene(cyclopentadienyl)(2,7-dimethylfluorenyl)zirconium dichloride, diisopropylsilylene(cyclopentadienyl)(3,6-di-tert-butylfluorenyl)zirconium dichloride, diisopropylsilylene(cyclopentadienyl)(octamethyloctahydrodibenzofluorenyl)zirconium dichloride, diisopropylsilylene(cyclopentadienyl)(fluorenyl)zirconium dimethyl, diisopropylsilylene(cyclopentadienyl)(2,7-di-tert-butylfluorenyl)zirconium dimethyl, diisopropylsilylene(cyclopentadienyl)(2,7-dimethylfluorenyl)zirconium dimethyl, diisopropylsilylene(cyclopentadienyl)(3,6-di-tert-butylfluorenyl)zirconium dimethyl, diisopropylsilylene(cyclopentadienyl)(octamethyloctahydrodibenzofluorenyl)zirconium dimethyl, di-n-butylsilylene(cyclopentadienyl)(fluorenyl)zirconium dichloride, di-n-butylsilylene(cyclopentadienyl)(2,7-di-tert-butylfluorenyl)zirconium dichloride, di-n-butylsilylene(cyclopentadienyl)(2,7-dimethylfluorenyl)zirconium dichloride, di-n-butylsilylene(cyclopentadienyl)(3,6-di-tert-butylfluorenyl)zirconium dichloride, di-n-butylsilylene(cyclopentadienyl)(octamethyloctahydrodibenzofluorenyl)zirconium dichloride, di-n-butylsilylene(cyclopentadienyl)(fluorenyl)zirconium dimethyl, di-n-butylsilylene(cyclopentadienyl)(2,7-di-tert-butylfluorenyl)zirconium dimethyl, di-n-butylsilylene(cyclopentadienyl)(2,7-dimethylfluorenyl)zirconium dimethyl, di-n-butylsilylene(cyclopentadienyl)(3,6-di-tert-butylfluorenyl)zirconium dimethyl, di-n-butylsilylene(cyclopentadienyl)(octamethyloctahydrodibenzofluorenyl)zirconium dimethyl, diisobutylsilylene(cyclopentadienyl)(fluorenyl)zirconium dichloride, diisobutylsilylene(cyclopentadienyl)(2,7-di-tert-butylfluorenyl)zirconium dichloride, diisobutylsilylene(cyclopentadienyl)(2,7-dimethylfluorenyl)zirconium dichloride, diisobutylsilylene(cyclopentadienyl)(3,6-di-tert-butylfluorenyl)zirconium dichloride, diisobutylsilylene(cyclopentadienyl)(octamethyloctahydrodibenzofluorenyl)zirconium dichloride, diisobutylsilylene(cyclopentadienyl)(fluorenyl)zirconium dimethyl, diisobutylsilylene(cyclopentadienyl)(2,7-di-tert-butylfluorenyl)zirconium dimethyl, diisobutylsilylene(cyclopentadienyl)(2,7-dimethylfluorenyl)zirconium dimethyl, diisobutylsilylene(cyclopentadienyl)(3,6-di-tert-butylfluorenyl)zirconium dimethyl, diisobutylsilylene(cyclopentadienyl)(octamethyloctahydrodibenzofluorenyl)zirconium dimethyl, di-tert-butylsilylene(cyclopentadienyl)(fluorenyl)zirconium dichloride, di-tert-butylsilylene(cyclopentadienyl)(2,7-di-tert-butylfluorenyl)zirconium dichloride, di-tert-butylsilylene(cyclopentadienyl)(2,7-dimethylfluorenyl)zirconium dichloride, di-tert-butylsilylene(cyclopentadienyl)(3,6-di-tert-butylfluorenyl)zirconium dichloride, di-tert-butylsilylene(cyclopentadienyl)(octamethyloctahydrodibenzofluorenyl)zirconium dichloride, di-tert-butylsilylene(cyclopentadienyl)(fluorenyl)zirconium dimethyl, di-tert-butylsilylene(cyclopentadienyl)(2,7-di-tert-butylfluorenyl)zirconium dimethyl, di-tert-butylsilylene(cyclopentadienyl)(2,7-dimethylfluorenyl)zirconium dimethyl, di-tert-butylsilylene(cyclopentadienyl)(3,6-di-tert-butylfluorenyl)zirconium dimethyl, di-tert-butylsilylene(cyclopentadienyl)(octamethyloctahydrodibenzofluorenyl)zirconium dimethyl, dicyclopentylsilylene(cyclopentadienyl)(fluorenyl)zirconium dichloride, dicyclopentylsilylene(cyclopentadienyl)(2,7-di-tert-butylfluorenyl)zirconium dichloride, dicyclopentylsilylene(cyclopentadienyl)(2,7-dimethylfluorenyl)zirconium dichloride, dicyclopentylsilylene(cyclopentadienyl)(3,6-di-tert-butylfluorenyl)zirconium dichloride, dicyclopentylsilylene(cyclopentadienyl)(octamethyloctahydrodibenzofluorenyl)zirconium dichloride, dicyclopentylsilylene(cyclopentadienyl)(fluorenyl)zirconium dimethyl, dicyclopentylsilylene(cyclopentadienyl)(2,7-di-tert-butylfluorenyl)zirconium dimethyl, dicyclopentylsilylene(cyclopentadienyl)(2,7-dimethylfluorenyl)zirconium dimethyl, dicyclopentylsilylene(cyclopentadienyl)(3,6-di-tert-butylfluorenyl)zirconium dimethyl, dicyclopentylsilylene(cyclopentadienyl)(octamethyloctahydrodibenzofluorenyl)zirconium dimethyl, dicyclohexylsilylene(cyclopentadienyl)(fluorenyl)zirconium dichloride, dicyclohexylsilylene(cyclopentadienyl)(2,7-di-tert-butylfluorenyl)zirconium dichloride, dicyclohexylsilylene(cyclopentadienyl)(2,7-dimethylfluorenyl)zirconium dichloride, dicyclohexylsilylene(cyclopentadienyl)(3,6-di-tert-butylfluorenyl)zirconium dichloride, dicyclohexylsilylene(cyclopentadienyl)(octamethyloctahydrodibenzofluorenyl)zirconium dichloride, dicyclohexylsilylene(cyclopentadienyl)(fluorenyl)zirconium dimethyl, dicyclohexylsilylene(cyclopentadienyl)(2,7-di-tert-butylfluorenyl)zirconium dimethyl, dicyclohexylsilylene(cyclopentadienyl)(2,7-dimethylfluorenyl)zirconium dimethyl, dicyclohexylsilylene(cyclopentadienyl)(3,6-di-tert-butylfluorenyl)zirconium dimethyl, dicyclohexylsilylene(cyclopentadienyl)(octamethyloctahydrodibenzofluorenyl)zirconium dimethyl, dicycloheptylsilylene(cyclopentadienyl)(fluorenyl)zirconium dichloride, dicycloheptylsilylene(cyclopentadienyl)(2,7-di-tert-butylfluorenyl)zirconium dichloride, dicycloheptylsilylene(cyclopentadienyl)(2,7-dimethylfluorenyl)zirconium dichloride, dicycloheptylsilylene(cyclopentadienyl)(3,6-di-tert-butylfluorenyl)zirconium dichloride, dicycloheptylsilylene(cyclopentadienyl)(octamethyloctahydrodibenzofluorenyl)zirconium dichloride, dicycloheptylsilylene(cyclopentadienyl)(fluorenyl)zirconium dimethyl, dicycloheptylsilylene(cyclopentadienyl)(2,7-di-tert-butylfluorenyl)zirconium dimethyl, dicycloheptylsilylene(cyclopentadienyl)(2,7-dimethylfluorenyl)zirconium dimethyl, dicycloheptylsilylene(cyclopentadienyl)(3,6-di-tert-butylfluorenyl)zirconium dimethyl, dicycloheptylsilylene(cyclopentadienyl)(octamethyloctahydrodibenzofluorenyl)zirconium dimethyl, diphenylsilylene(cyclopentadienyl)(fluorenyl)zirconium dichloride, diphenylsilylene(cyclopentadienyl)(2,7-dimethylfluorenyl)zirconium dichloride, diphenylsilylene(cyclopentadienyl)(3,6-di-tert-butylfluorenyl)zirconium dichloride, diphenylsilylene(cyclopentadienyl)(octamethyloctahydrodibenzofluorenyl)zirconium dichloride, diphenylsilylene(cyclopentadienyl)(fluorenyl)zirconium dimethyl, diphenylsilylene(cyclopentadienyl)(2,7-di-tert-butylfluorenyl)zirconium dimethyl, diphenylsilylene(cyclopentadienyl)(2,7-dimethylfluorenyl)zirconium dimethyl, diphenylsilylene(cyclopentadienyl)(3,6-di-tert-butylfluorenyl)zirconium dimethyl, diphenylsilylene(cyclopentadienyl)(octamethyloctahydrodibenzofluorenyl)zirconium dimethyl, di(m-tolyl)silylene(cyclopentadienyl)(fluorenyl)zirconium dichloride, di(m-tolyl)silylene(cyclopentadienyl)(2,7-di-tert-butylfluorenyl)zirconium dichloride, di(m-tolyl)silylene(cyclopentadienyl)(2,7-dimethylfluorenyl)zirconium dichloride, di(m-tolyl)silylene(cyclopentadienyl)(3,6-di-tert-butylfluorenyl)zirconium dichloride, di(m-tolyl)silylene(cyclopentadienyl)(octamethyloctahydrodibenzofluorenyl)zirconium dichloride, di(m-tolyl)silylene(cyclopentadienyl)(fluorenyl)zirconium dimethyl, di(m-tolyl)silylene(cyclopentadienyl)(2,7-di-tert-butylfluorenyl)zirconium dimethyl, di(m-tolyl)silylene(cyclopentadienyl)(2,7-dimethylfluorenyl)zirconium dimethyl, di(m-tolyl)silylene(cyclopentadienyl)(3,6-di-tert-butylfluorenyl)zirconium dimethyl, di(m-tolyl)silylene(cyclopentadienyl)(octamethyloctahydrodibenzofluorenyl)zirconium dimethyl, di(p-tolyl)silylene(cyclopentadienyl)(fluorenyl)zirconium dichloride, di(p-tolyl)silylene(cyclopentadienyl)(2,7-di-tert-butylfluorenyl)zirconium dichloride, di(p-tolyl)silylene(cyclopentadienyl)(2,7-dimethylfluorenyl)zirconium dichloride, di(p-tolyl)silylene(cyclopentadienyl)(3,6-di-tert-butylfluorenyl)zirconium dichloride, di(p-tolyl)silylene(cyclopentadienyl)(octamethyloctahydrodibenzofluorenyl)zirconium dichloride, di(p-tolyl)silylene(cyclopentadienyl)(fluorenyl)zirconium dimethyl, di(p-tolyl)silylene(cyclopentadienyl)(2,7-di-tert-butylfluorenyl)zirconium dimethyl, di(p-tolyl)silylene(cyclopentadienyl)(2,7-dimethylfluorenyl)zirconium dimethyl, di(p-tolyl)silylene(cyclopentadienyl)(3,6-di-tert-butylfluorenyl)zirconium dimethyl, di(p-tolyl)silylene(cyclopentadienyl)(octamethyloctahydrodibenzofluorenyl)zirconium dimethyl, 1-silacyclopentylidene(cyclopentadienyl)(fluorenyl)zirconium dichloride, 1-silacyclopentylidene(cyclopentadienyl)(2,7-di-tert-butylfluorenyl)zirconium dichloride, 1-silacyclopentylidene(cyclopentadienyl)(2,7-dimethylfluorenyl)zirconium dichloride, 1-silacyclopentylidene(cyclopentadienyl)(3,6-di-tert-butylfluorenyl)zirconium dichloride, 1-silacyclopentylidene(cyclopentadienyl)(octamethyloctahydrodibenzofluorenyl)zirconium dichloride, 1-silacyclopentylidene(cyclopentadienyl)(fluorenyl)zirconium dimethyl, 1-silacyclopentylidene(cyclopentadienyl)(2,7-di-tert-butylfluorenyl)zirconium dimethyl, 1-silacyclopentylidene(cyclopentadienyl)(2,7-dimethylfluorenyl)zirconium dimethyl, 1-silacyclopentylidene(cyclopentadienyl)(3,6-di-tert-butylfluorenyl)zirconium dimethyl, and 1-silacyclopentylidene(cyclopentadienyl)(octamethyloctahydrodibenzofluorenyl)zirconium dimethyl.

In these preferable bridged metallocene compounds (W-1) to (W-5) mentioned above, $R^1$ to $R^4$ are preferably all hydrogen in view of polymerization activity, etc.

Method for Preparation of the Metallocene Compound

The metallocene compound (W) of the invention can be prepared by a known process without specific limitations, for example as disclosed in WO 01/27174 by the present applicant. For example, the metallocene compound (W) of the formula [I] can be prepared as described below.

A precursor [1] of the metallocene compound (W) is first prepared by the process [A] or [B]:

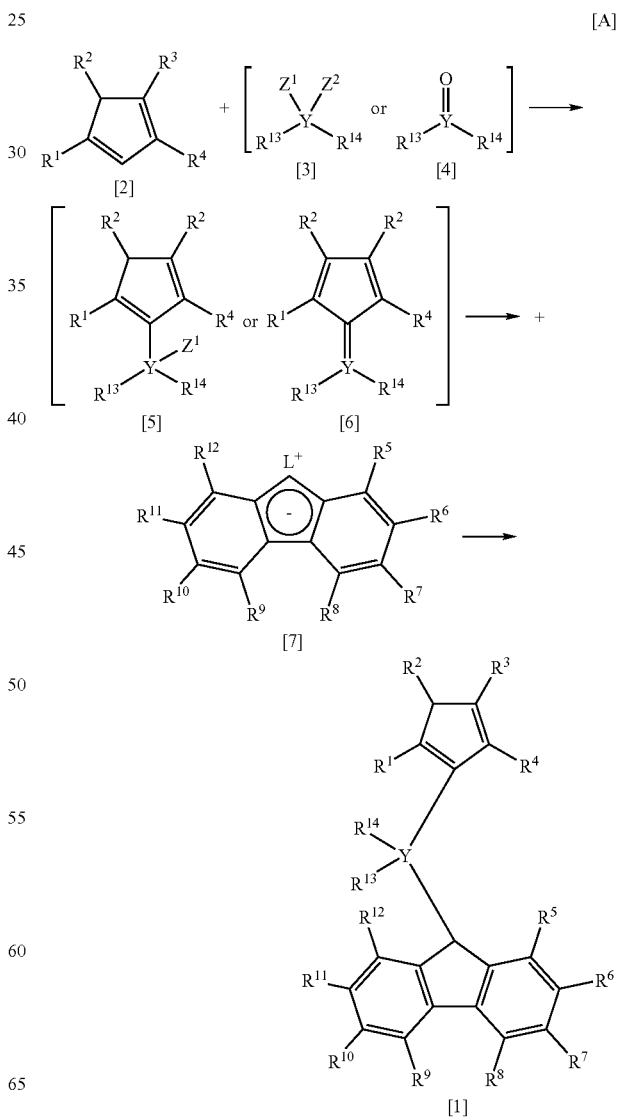

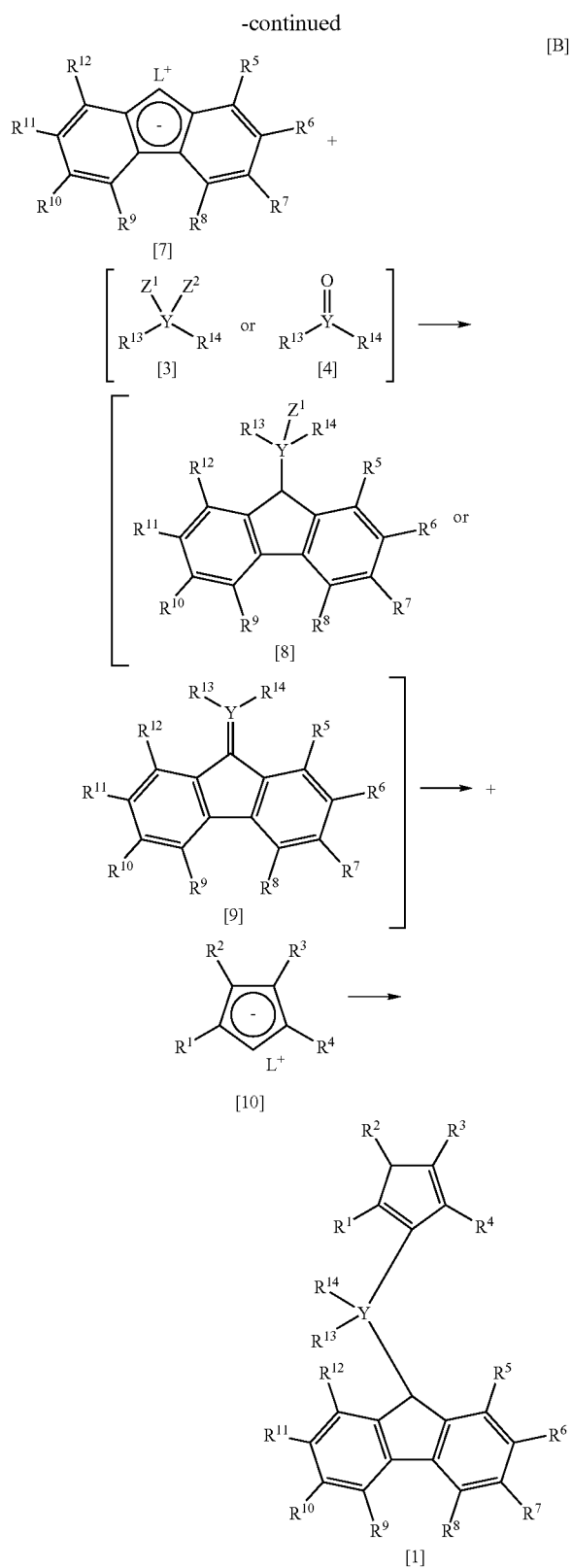

wherein R[1] to R[14] and Y are as in the formula [I]; L is an alkali metal; Z[1] and Z[2], which may be the same or different, are each a halogen or an anionic ligand; and [2] and [5], which are shown in the formulae with one exemplary form, may be each an isomer different only in the positions of double bonds in the cyclopentadienyl ring, or a mixture of such isomers.

In the reaction process [A] or [B], the alkali metal used can be lithium, sodium, potassium, etc.; the alkali earth metal used can be magnesium, calcium, etc.; the halogen can be fluorine, chlorine, bromine or iodine; and the anionic ligand can be an alkoxy group, such as methoxy, tert-butoxy or phenoxy, a carboxylate group, such as acetate or benzoate, or a sulfonate group, such as mesylate or tosylate.

An exemplary process for the preparation of the metallocene compound from the precursor [1] will be given below. However, the preparation is not limited to the following and can be made by any conventional processes.

The precursor [1] obtained by the reaction process [A] or [B] is contacted with an alkali metal, a hydrogenated alkali metal or an organoalkali metal in an organic solvent at a reaction temperature of −80 to 200° C. to form a dialkali metal salt.

Examples of the organic solvent include aliphatic hydrocarbons, such as pentane, hexane, heptane, cyclohexane and decalin; aromatic hydrocarbons, such as benzene, toluene and xylene; ethers, such as THF, di-n-butylether, dioxane and 1,2-dimethoxyethane; and halogenated hydrocarbons, such as dichloromethane and chloroform.

Examples of the alkali metal used in the reaction include lithium, sodium and potassium; those of the hydrogenated alkali metal include hydrogenated sodium and hydrogenated potassium; and those of the organoalkali metal include methyllithium, butyllithium and phenyllithium.

Then the dialkali metal salt is reacted in an organic solvent with a compound represented by the formula [11], so that the metallocene compound of the formula [I] can be synthesized:

$$MZ_k \quad [11]$$

wherein M is titanium, zirconium or hafnium; Z is a halogen, an anionic ligand or a neutral ligand capable of coordination by a lone pair of electrons, and may be the same or different when plural; and k is an integer from 3 to 6.

Examples of the preferred compounds [11] include trivalent or tetravalent titanium fluorides, chlorides, bromides and iodides; tetravalent zirconium fluorides, chlorides, bromides and iodides; tetravalent hafnium fluorides, chlorides, bromides and iodides; and complexes thereof with ethers, such as THF, di-n-butylether, dioxane and 1,2-dimethoxyethane.

The organic solvent used herein is the same as above.

The reaction between the dialkali metal salt and the compound [11] is preferably an equimolar reaction and carried out in the organic solvent at a reaction temperature of −80 to 200° C.

The resultant metallocene compound can be isolated and purified by methods, such as extraction, recrystallization and sublimation. Identification of the bridged metallocene compound obtained as above can be made by proton nuclear magnetic resonance, $^{13}C$ nuclear magnetic resonance, mass spectrometric analysis or elemental analysis.

Olefin Polymerization Catalyst

A preferable embodiment of the metallocene compound (W) as an olefin polymerization catalyst will be given below.

The olefin polymerization catalyst comprises:
(A) the metallocene compound (W) and
(B) at least one compound selected from:
(B-1) an organometallic compound,
(B-2) an organoaluminum oxy-compound and (B-3) a compound which reacts with the metallocene compound (A) to form an ion pair.

Each component will be described in detail hereinafter.

(B-1) Organometallic Compound

The organometallic compound (B-1) is of Group 1, 2, 12 or 13 metal of the periodic table, examples given below:

(B-1a) organoaluminum compounds represented by $$R^a_m Al(OR^b)_n H_p X_q$$

wherein $R^a$ and $R^b$, which may be the same or different, are hydrocarbon groups of 1 to 15, preferably 1 to 4 carbon atoms, X is a halogen atom, $0 < m \leq 3$, $0 \leq n < 3$, $0 \leq p < 3$, $0 \leq q < 3$ and $m+n+p+q=3$, such as trimethylaluminum, tri-n-butylaluminum, triisobutylaluminum and diisobutylaluminumhydride;

(B-1b) alkyl complex compounds of Group 1 metal of the periodic table and aluminum, represented by $$M^2 Al R^a_4$$

wherein $M^2$ is Li, Na or K, and $R^a$ is a hydrocarbon group of 1 to 15, preferably 1 to 4 carbon atoms, such as LiAl$(C_2H_5)_4$ and LiAl$(C_7H_{15})_4$;

(B-1c) dialkyl compounds of Group 2 or 12 metal of the periodic table, represented by $$R^a R^b M^3$$

wherein $R^a$ and $R^b$, which may be the same or different, are hydrocarbon groups of 1 to 15, preferably 1 to 4 carbon atoms, and $M^3$ is Mg, Zn or Cd.

Of the above organometallic compounds (B-1), the organoaluminum compounds are preferred. The organometallic compounds (B-1) may be used individually or in combination.

(B-2) Organoaluminum Oxy-compound

The organoaluminum oxy-compound (B-2) may be a conventional aluminoxane, and is represented by, for example, the formula(e) [12] and/or [13]:

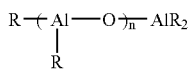  [12]

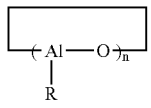  [13]

wherein R is a hydrocarbon group of 1 to 10 carbon atoms, and n is an integer of 2 or more. Particularly, aluminoxanes of the above formulae in which R is a methyl group (methylaluminoxanes) and n is 3 or more, preferably 10 or more, are suitably used. These aluminoxanes may contain slight amounts of organoaluminum compounds. Also, benzene-insoluble organoaluminum oxy-compounds as mentioned in JP-A-2 (1990)/78687 are also employable. Further, organoaluminum oxy-compounds as mentioned in JP-A-2 (1990)/167305 and aluminoxanes having at least two alkyl groups as mentioned in JP-A-2(1990)/24701 and JP-A-3 (1991)/103407 are suitably used.

For example, conventional aluminoxanes may be prepared by the following processes, and are obtained usually as a solution in hydrocarbon solvent.

(1) A process in which an organoaluminum compound, such as trialkylaluminum, is added to a hydrocarbon medium suspension of a compound containing absorbed water or a salt containing water of crystallization, such as magnesium chloride hydrate, copper sulfate hydrate, aluminum sulfate hydrate, nickel sulfate hydrate or cerous chloride hydrate, to react the organoaluminum compound with absorbed water or water of crystallization.

(2) A process in which water, ice or water vapor is allowed to act directly on an organoaluminum compound, such as trialkylaluminum, in a medium, e.g., benzene, toluene, n-butylether or tetrahydrofuran.

(3) A process in which an organoaluminum compound, such as trialkylaluminum, is reacted with an organotin oxide, such as dimethyltin oxide or dibutyltin oxide, in a medium, e.g., decane, benzene or toluene.

The aluminoxanes may contain small amounts of organometallic component. After the solvent and unreacted organoaluminum compound are distilled away from the recovered solution of aluminoxane, the remainder may be redissolved in a solvent or suspended in a poor solvent for aluminoxane.

Examples of the organoaluminum compound used in preparing the aluminoxane include the same compounds as listed as the organoaluminum compounds (B-1a).

Of those compounds, trialkylaluminum and tricycloalkyl aluminum, particularly trimethylaluminum, are preferred.

The organoaluminum compounds may be used individually or in combination.

The organoaluminum oxy-compound desirably contains Al components that will dissolve in benzene at 60° C., in terms of Al atom, at 10% or less, preferably 5% or less, particularly 2% or less. That is, the organoaluminum oxy-compound is preferably insoluble or hardly soluble in benzene. The organoaluminum oxy-compounds (B-2) can be used individually or in combination.

(B-3) Compound which Reacts with the Transition Metal Compound to Form an Ion Pair The compound (B-3) which reacts with the bridged metallocene compound (A) to form an ion pair (hereinafter the "ionizing ionic compound") can be, for example, any of the Lewis acids, ionic compounds, borane compounds and carborane compounds mentioned in JP-A-1(1989)/501950, JP-A-1(1989)/502036, JP-A-3(1991)/179005, JP-A-3 (1991)/179006, JP-A-3(1991)/207703, JP-A-3 (1991) /207704 and U.S. Pat. No. 5,321,106. Further, heteropoly compounds and isopoly compounds are also employable. These ionizing ionic compounds (B-3) may be used individually or in combination.

When the bridged metallocene compound is used in combination with the auxiliary catalyst component of organoaluminum oxy-compound (B-2), such as methylaluminoxane, the resultant olefin polymerization catalyst will exhibit high polymerization activity particularly for olefin compounds.

In addition to the transition metal compound (A) and at least one compound (B) of the organometallic compound (B-1) the organoaluminum oxy-compound (B-2) and the ionizing ionic compound (B-3), the olefin polymerization catalyst may optionally contain a carrier (C).

(C) Carrier

The carrier (C) is an inorganic or organic solid compound of granular or particle state. Of inorganic compounds, porous oxides, inorganic chlorides, clay, clay minerals and layered compounds capable of ion exchange are preferred.

Suitable porous oxides include $SiO_2$, $Al_2O_3$, MgO, ZrO, $TiO_2$, $B_2O_3$, CaO, ZnO, BaO, $ThO_2$, and composites and mixtures thereof; for example natural or synthetic zeolites, $SiO_2$—MgO, $SiO_2$—$Al_2O_3$, $SiO_2$—$TiO_2$, $SiO_2$—$V_2O_5$, $SiO_2$—$Cr_2O_3$ and $SiO_2$—$TiO_2$—MgO. Porous oxides mainly comprising $SiO_2$ and/or $Al_2O_3$ are preferable. The porous oxides have various properties according to the type and production process. The carrier used in the invention desirably ranges from 0.5 to 300 µm, preferably 1.0 to 200 µm in the particle diameter, and from 50 to 1000 m$^2$/g, preferably 100 to 700 m$^2$/g in the specific surface area, and from 0.3 to 3.0 cm$^3$/g in the pore volume. The carrier may optionally be calcined at 100 to 1000° C., preferably 150 to 700° C. prior to use.

Suitable inorganic chlorides include $MgCl_2$, $MgBr_2$, $MnCl_2$ and $MnBr_2$. The inorganic chlorides may be used directly or after ground by a boll mill or a vibrating mill. Alternatively, the inorganic chloride may be dissolved in a solvent, such as alcohol, and separated out as fine particles by means of a separating agent.

The clay for use in the invention mainly comprises a clay mineral. The layered compound capable of ion exchange has a crystal structure in which planes formed by ionic bonds pile parallel one another with weak bonding strength, and contains ions capable of ion exchange. Most clay minerals are the ion-exchangeable layered compounds. The clay, clay minerals and ion-exchangeable layered compounds may be either natural or synthetic. Examples of clay, clay minerals and ion exchangeable layered compounds include clay, clay minerals and ionic crystalline compounds having a layered crystal structure such as hexagonal closest packing type, antimony type, $CdCl_2$ type or $CdI_2$ type. Examples of the clay and clay minerals include kaolin, bentonite, kibushi clay, potter's clay, allophane, hisingerite, pyrophyllite, mica, montmorillonite, vermiculite, chlorite, palygorskite, kaolinite, nacrite, dickite and halloysite. Examples of the ion-exchangeable layered compounds include crystalline acid salts of polyvalent metals, such as α-Zr $(HAsO_4)_2 \cdot H_2O$, α-Zr $(HPO_4)_2$, α-Zr $(KPO_4)_2 \cdot 3H_2O$, α-Ti$(HPO_4)_2$, α-Ti$(HAsO_4)_2 \cdot H_2O$, α-Sn $(HPO_4)_2 \cdot H_2O$, γ-Zr$(HPO_4)_2$, γ-Ti$(HPO_4)_2$ and γ-Ti$(NH_4 PO_4)_2 \cdot H_2O$. The clay and clay minerals may preferably be subjected to a chemical treatment. The chemical treatment may be a surface treatment to remove impurities attached to the surface, a treatment affecting the crystal structure of clay, or any other treatment. Examples of such chemical treatments include acid treatment, alkali treatment, salt treatment and organic substance treatment.

The ion-exchangeable layered compound may be enlarged in interlaminar spacing by replacing the exchangeable ions between layers with larger and bulkier ions by means of its ion exchangeability. The bulky ions play a role as supporting column for the layered structure, and are generally called pillars. Introducing different substances between layers of a layered compound is called intercalation. Guest compounds for the intercalation include cationic inorganic compounds, such as $TiCl_4$ and $ZrCl_4$, metallic alkoxides, such as Ti(OR)$_4$, Zr(OR)$_4$, PO(OR)$_3$ and B(OR)$_3$ (wherein R is a hydrocarbon group, etc.), and metallic hydroxide ions, such as $[Al_{13}O_4 (OH)_{24}]^{7+}$, $[Zr_4 (OH)_{14}]^{2+}$ and $[Fe_3O(OCOCH_3)_6]^+$. These compounds may be used individually or in combination. The intercalation of these compounds may be carried out in the presence of polymers obtained by hydrolysis of metallic alkoxides, such as Si(OR)$_4$, Al(OR)$_3$ and Ge(OR)$_4$ (wherein R is a hydrocarbon group, etc.), or colloidal inorganic compounds, such as $SiO_2$. Exemplary pillars are oxides which occur as a result of dehydration by heating after the metallic hydroxide ions are intercalated between layers. Of the inorganic compounds, the clay and clay minerals, particularly montmorillonite, vermiculite, pectolite, taeniolite and synthetic mica, are preferred.

The organic compounds are granular or particulate solids ranging from 0.5 to 300 µm in particle diameter. Specific examples include (co)polymers mainly comprising an α-olefin of 2 to 14 carbon atoms, such as ethylene, propylene, 1-butene or 4-methyl-1-pentene; (co)polymers mainly comprising vinylcyclohexane or styrene; and modified products thereof.

In addition to the bridged metallocene compound (A) and at least one compound (B) of the organometallic compound (B-1) the organoaluminum oxy-compound (B-2) and the ionizing ionic compound (B-3), optionally together with the carrier (C), the olefin polymerization catalyst may optionally contain an organic compound component (D).

(D) Organic Compound Component

The organic compound component (D) is used optionally for the purpose of improving the polymerization activity and properties of resultant polymers. Examples of the organic compound, although not limited thereto, include alcohols, phenolic compounds, carboxylic acids, phosphorous compounds and sulfonates.

In carrying out polymerization, the above components may be used arbitrarily in any order of addition; some examples are given below:

(1) The component (A) alone is added into a polymerization reactor.

(2) The components (A) and (B) are added into a polymerization reactor in arbitrary order.

(3) A catalyst component wherein the component (A) is supported on the carrier (C), and the component (B) are added into a polymerization reactor in arbitrary order.

(4) A catalyst component wherein the component (B) is supported on the carrier (C), and the component (A) are added into a polymerization reactor in arbitrary order.

(5) A catalyst component wherein the components (A) and (B) are supported on the carrier (C) is added into a polymerization reactor.

In the above methods (2) to (5), the two or more catalyst components may have been in contact.

In the method (4) or (5) in which the component (B) is supported on the carrier, the unsupported component (B) may be independently added in arbitrary order according to necessity; the components (B) maybe the same or different kind.

The solid catalyst component in which the component (A) is supported on the component (C) or in which the components (A) and (B) are supported on the component (C), may be prepolymerized with an olefin. The prepolymerized solid catalyst component may further be treated with other catalyst component.

Method for Polymerization of Olefin

In the invention, the metallocene compound (W') of the formula [I'] may be used in place of the metallocene compound (W):

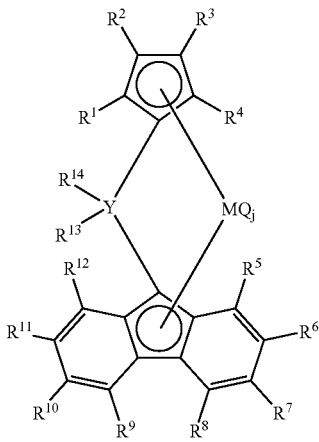

[I']

wherein $R^1$ to $R^{14}$, which may be the same or different, are each hydrogen, a hydrocarbon group or a silicon-containing group; and $R^{13}$ and $R^{14}$ may be linked with each other to form a ring. It is important in the metallocene compound (W') of the formula [I'] that the substituents $R^5$ to $R^{12}$ for the fluorenyl group are not hydrogen at the same time. High polymerization activity can be achieved when at least one hydrogen atom as the substituent for the fluorenyl group has been substituted. In a more preferred embodiment of the substituted fluorenyl group in the formula [I'], arbitrary two or more substituents of $R^6$ to $R^{11}$ are hydrocarbon groups of 1 to 20 carbon atoms or silicon-containing groups. In view of easy preparation of the metallocene compound and activity in the olefin polymerization, $R^6$ and $R^{11}$, or $R^7$ and $R^{10}$ are preferably the same groups. The hydrocarbon groups and the silicon-containing groups are as exemplified with respect to the metallocene compound (W) of the formula [I].

In the formula [I'], M is Ti, Zr or Hf, and Y is carbon, silicon, germanium or tin.

Q and j are as defined in the formula [I] for the metallocene compound (W).

The metallocene compounds (W') of the formula [I'] in which $R^{13}$ and $R^{14}$ are independently a phenyl, methyl or pentamethylene group and Y is carbon, are preferably employed.

Examples of the compounds having the above characteristics in the chemical structure include cyclohexylidene(cyclopentadienyl)(2,7-di-tert-butylfluorenyl)zirconium dichloride, dimethylmethylene(cyclopentadienyl)(2,7-di-tert-butylfluorenyl)zirconium dichloride, diphenylmethylene(cyclopentadienyl)(2,7-di-tert-butylfluorenyl)zirconium dichloride, dimethylmethylene(cyclopentadienyl)(3,6-di-tert- butylfluorenyl)zirconium dichloride, diphenylmethylene(cyclopentadienyl)(3,6-di-tert-butylfluorenyl)zirconium dichloride, cyclohexylidene(cyclopentadienyl)(2,7-di-tert-butylfluorenyl)hafnium dichloride, dimethylmethylene(cyclopentadienyl)(2,7-di-tert-butylfluorenyl)hafnium dichloride, diphenylmethylene(cyclopentadienyl)(2,7-di-tert-butylfluorenyl)hafnium dichloride, cyclohexylidene(cyclopentadienyl)(2,7-di-tert-butylfluorenyl)titanium dichloride, dimethylmethylene(cyclopentadienyl)(2,7-di-tert-butylfluorenyl)titanium dichloride, and diphenylmethylene(cyclopentadienyl)(2,7-di-tert-butylfluorenyl)titanium dichloride.

When the metallocene compound (W') is used for the olefin polymerization catalyst, the polymerization catalyst may be prepared by the same process as in the case of the metallocene compound (W).

According to the method for olefin polymerization of the invention, an olefinic polymer is obtained by polymerizing or copolymerizing an olefin in the presence of the olefin polymerization catalyst which comprises the metallocene compound (W) or (W').

The polymerization may be carried out by a liquid-phase polymerization process, such as solution polymerization or suspension polymerization, or a gas-phase polymerization process. Examples of the inert hydrocarbon solvent used in the liquid-phase polymerization include aliphatic hydrocarbons, such as propane, butane, pentane, hexane, heptane, octane, decane, dodecane and kerosine; alicyclic hydrocarbons, such as cyclopentane, cyclohexane and methylcyclopentane; aromatic hydrocarbons, such as benzene, toluene and xylene; halogenated hydrocarbons, such as ethylene chloride, chlorobenzene and dichloromethane; and mixtures thereof. The olefin itself can be also used as a solvent.

In carrying out polymerization of olefin in the presence of the olefin polymerization catalyst, the component (A) is used in an amount of $10^{-9}$ to $10^{-1}$ mol, preferably $10^{-8}$ to $10^{-2}$ mol per 1 liter of the reaction volume.

The component (B-1) is used in an amount such that the molar ratio ((B-1)/M) of the component (B-1) to the transition metal atoms (M) in the component (A) will be 0.01 to 5000, preferably 0.05 to 2000. The component (B-2) is used in an amount such that the molar ratio ((B-2)/M) of the component (B-2) in terms of aluminum atom to the transition metal atoms (M) in the component (A) will be 10 to 5000, preferably 20 to 2000. The component (B-3) is used in an amount such that the molar ratio ((B-3)/M) of the component (B-3) to the transition metal atoms (M) in the component (A) will be usually 1 to 10, preferably 1 to 5.

The component (D), in the case of the component (B-1) is used in an amount such that the molar ratio ((D)/(B-1)) will be 0.01 to 10, preferably 0.1 to 5; in the case of the component (B-2), in an amount such that the molar ratio ((D)/(B-2)) will be usually 0.001 to 2, preferably 0.005 to 1; and in the case of the component (B-3), in an amount such that the molar ratio ((D)/(B-3)) will be 0.01 to 10, preferably 0.1 to 5.

The olefin polymerization in the presence of the olefin polymerization catalyst is conducted usually at −50 to +200° C., preferably 0 to 170° C. The polymerization pressure (gauge pressure) is from atmospheric pressure to 10 MPa, preferably from atmospheric pressure to 5 MPa. The polymerization can be carried out batchwise, semi-continuously or continuously, and in two or more stages under different conditions. The molecular weight of resulting olefin polymer may be adjusted by allowing the presence of hydrogen in the polymerization system, controlling the polymerization temperature or changing the amount of the component (B). When hydrogen is added, the addition is suitably made at 0.001 to 100 NL based on 1 kg of olefin.

For the polymerization of the invention, at least one monomer is selected from ethylene and α-olefins, in which ethylene is an essential monomer. Examples of the α-olefins include linear or branched α-olefins of 3 to 20, preferably 3 to 10 carbon atoms, such as propylene, 1-butene, 2-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene and 1-eicosene. Suitable monomers for the polymerization of the invention further include cycloolefins of 3 to 30, preferably 3 to 20 carbon atoms, such as cyclopentene, cycloheptene, norbornene, 5-methyl-2-norbornene, tetracyclododecene and 2-methyl-1,4,5,8-dimethano-1,2,3,4,4a,5,8,8a-octahydronaphthalene; polar monomers, such as α,β-unsaturated carboxylic acids, e.g., acrylic acid, methacrylic acid, fumaric acid, maleic anhydride, itaconic acid, itaconic anhydride, bicyclo(2,2,1)-5-heptene-2,3-dicarboxylic anhydride, and metallic salts thereof with sodium, potassium, lithium, zinc, magnesium and calcium; α,β-unsaturated carboxylates, such as methyl acrylate, n-butyl acrylate, n-propyl acrylate, isopropyl acrylate, n-butyl acrylate, isobutyl acrylate, tert-butyl acrylate, 2-(n-butyl)hexyl acrylate, methyl methacrylate, n-butyl methacrylate, n-propyl methacrylate, isopropyl methacrylate, n-butyl methacrylate and isobutyl methacrylate; vinyl esters, such as vinyl acetate, vinyl propionate, vinyl caproate, vinyl caprate, vinyl laurate, vinyl stearate and vinyl trifluoroacetate; and unsaturated glycidyls, such as glycidyl acrylate, glycidyl methacrylate and monoglycidyl itaconate. Also, the polymerization can be carried out with at least one of the following compounds present in the reaction system: vinylcyclohexane, diene, polyene; aromatic vinyl compounds, such as styrene and mono- or poly-alkyl styrenes, e.g., o-methylstyrene, m-methylstyrene, p-methylstyrene, o,p-dimethylstyrene, o-(n-butyl)styrene, m-(n-butyl)styrene and p-(n-butyl)styrene; styrene derivatives containing a functional group, such as methoxystyrene, ethoxystyrene, vinylbenzoic acid, methyl vinylbenzoate, vinylbenzyl acetate, hydroxystyrene, o-chlorostyrene, p-chlorostyrene and divinylbenzene; 3-phenylpropylene, 4-phenylpropylene and α-methylstyrene.

In the polymerization as mentioned above, at least one monomer is ethylene. When two or more monomers are selected, the polymerization is preferably carried out so that an ethylene based polymer with an ethylene content of more than 50 mol % is obtained.

Effect of the Invention

The olefin polymerization catalyst which comprises the bridged metallocene compound enables high polymerization activity, so that olefin homopolymers or copolymers can be obtained with high polymerization activity by carrying out homo- or copolymerization of olefins in the presence of the olefin polymerization catalyst.

EXAMPLE

The present invention will be described in detail with reference to the following Examples, but it should be construed that the invention is in no way limited to those Examples.

The structures of the metallocene compounds and precursors thereof were determined by $^1$H-NMR at 270 MH$_z$ (GSH-270 available from JEOL) and FD-mass spectrometric analysis (SX-102A available form JEOL).

Olefin polymers obtained with use of the catalyst containing the transition metal compound, were measured for the following properties.

[Weight-Average Molecular Weight (Mw) and Number-average Molecular Weight (Mn)]

These properties were determined by means of GPC-150C (available from Waters Corporation) as follows. The measurement was carried out using separatory columns TSKgel GMH6-HT and TSKgel GMH6-HTL, both having an inner diameter 7.5 mm and a length 600 mm, at a column temperature of 140° C. A sample, 500 microliters, having a concentration of 0.1 wt % was moved at a rate of 1.0 ml/min using o-dichlorobenzene (Wako Pure Chemical Industries, Ltd.) as a mobile phase and 0.025 wt % of BHT (Takeda Chemical Industries, Ltd.) as an antioxidant. A differential refractometer was used as a detector. Standard polystyrenes used for the measurement had molecular weights Mw<1000 and Mw≧4×10$^6$ (available from Toso Corporation) and 1000≦Mw≦4×10$^6$ (available from Pressure Chemical Co.).

[Intrinsic Viscosity [η]]

The intrinsic viscosity was measured at 135° C. in a decalin solution. Specifically, granulated pellets about 20 mg were dissolved in decalin 15 ml, and a specific viscosity $\eta_{sp}$ was measured in an oil bath at 135° C.; after the decalin solution was diluted with decalin 5 ml, a specific viscosity $\eta_{sp}$ was likewise measured. The dilution was further repeated twice to extrapolate the concentration (C) to 0, and the value $\eta_{sp}/C$ was obtained as the intrinsic viscosity.

$$[\eta]=\lim(\eta_{sp}/C)(C \to 0)$$

[Melt Flow Rate (MFR$_{21.6}$, MFR$_{10}$, MFR$_{2.16}$)]

The melt flow rate was determined in accordance with ASTM D-1238 at 190° C. and under a load of 21.6 kg, 10 kg or 2.16 kg.

[Density]

Each olefin polymer was made into a sheet 0.5 mm thick with pressure 100 kg/cm$^2$ by a hydraulic hot press set at 190° C. (manufactured by SHINTO METAL INDUSTRIES, LTD). The spacer consisted of a plate 240×240×0.5 mm with 9 squares 45×45×0.5 mm. The sheet was then cooled as being compressed with pressure 100 kg/cm$^2$ by another hydraulic hot press set at 20° C. (manufactured by SHINTO METAL INDUSTRIES, LTD) to give a sample for measurement. The hot plate was an SUS plate 5 mm thick.

The pressed sheet was treated by heating at 120° C. for 1 hour, and gradually cooled to room temperature with linear temperature lowering. Then the density was determined by use of a density gradient tube.

[Synthesis of Known Metallocene Compounds]

The following known metallocene compounds were synthesized by the methods mentioned in corresponding literature or patent publications.

(1) dimethylmethylene($\eta^5$-cyclopentadienyl)($\eta^5$-fluorenyl)zirconium dichloride: synthesized as mentioned in JP-A-2 (1990)/41303

(2) diphenylmethylene($\eta^5$-cyclopentadienyl)($\eta^5$-fluorenyl)zirconium dichloride: synthesized as mentioned in JP-A-2 (1990)/274703

(3) cyclohexylidene($\eta^5$-cyclopentadienyl)($\eta^5$-fluorenyl)zirconium dichloride: synthesized as mentioned in JP-A-3 (1991)/193797

(4) dimethylsilylene($\eta^5$-cyclopentadienyl)($\eta^5$-fluorenyl)zirconium dichloride: synthesized as mentioned in J. Organomet. Chem., 497, 1 (1995)

(5) diphenylsilylene($\eta^5$-cyclopentadienyl)($\eta^5$-fluorenyl)zirconium dichloride: synthesized as mentioned in J. Organomet. Chem., 509, 63 (1996)

(6) diphenylsilylene(5-cyclopentadienyl){$\eta^5$(2,7-di-tert-butylfluorenyl)}zirconium dichloride: synthesized as mentioned in J. Organomet. Chem., 509, 63 (1996)

(7) dimethylmethylene($\eta^5$-cyclopentadienyl){$\eta^5$-(2,7-di-tert-butylfluorenyl)}zirconium dichloride: synthesized as mentioned in JP-A-4(1992)/69394

(8) dimethylmethylene($\eta^5$-cyclopentadienyl){$\eta^5$-(3,6-di-tert-butylfluorenyl)}zirconium dichloride: synthesized as mentioned in JP-A-2000/212194

(9) diphenylmethylene($\eta^5$-cyclopentadienyl){$\eta^5$-(2,7-di-tert-butylfluorenyl)}zirconium dichloride: synthesized as mentioned in JP-A-6(1994)/172443

(10) diphenylmethylene($\eta^5$-cyclopentadienyl){$\eta^5$-(3, 6-di-tert-butylfluorenyl)}zirconium dichloride: synthesized as mentioned in JP-A-2000/212194

(11) cyclohexylidene($\eta^5$-cyclopentadienyl){$\eta^5$-(2,7-di-tert-butylfluorenyl)}zirconium dichloride: synthesized as mentioned in JP-A-2000/26490

Example 1

Synthesis of dimethylmethylene($\eta^5$-cyclopentadienyl)($\eta^5$-octamethyloctahydrodibenzofluorenyl)zirconium dichloride (i) Synthesis of octamethyloctahydrodibenzofluorene Into a 500 ml three-necked flask thoroughly purged with nitrogen, equipped with a three-way cock, a dropping funnel and a magnetic stirrer, were introduced fluorene 9.72 g (58.6 mmol) and 2,5-dimethyl-2,5-hexanediol 19.61 g (134 mmol) at room temperature. Dehydrated dichloromethane 85 ml was further added, and the contents were stirred by the magnetic stirrer and cooled to −8° C. in an ice bath. Ground anhydrous aluminum chloride 38.9 g (292 mmol) was added to the mixture over a period of 70 minutes, and stirring was conducted for 2 hours at 0° C. and further for 19 hours at room temperature outside the ice bath. Thenthe resulting solutionwas quenched by being poured into ice water 150 ml. Soluble matters were extracted with diethyl ether 500 ml, and an organic phase was neutralized with a saturated aqueous solution of sodium hydrogencarbonate and then washed with water. The fractionated organic phase was dried over anhydrous magnesium sulfate. After the magnesium sulfate was filtered off, the solvent of the filtrate was distilled away under reduced pressure. The residue was washed six times with n-hexane 10 ml through a Kiriyama funnel and dried under reduced pressure to give white powder (12.0 g, 53% yield).

$^1$H NMR spectrum (270 MHz, CDCl$_3$): δ/ppm 1.3 (s, 12H), 1.4 (s, 12H), 1.7 (s, 8H), 3.8 (s, 2H), 7.4 (s, 2H), 7.6 (s, 2H)

FD-MS Spectrum: M/z 386 (M$^+$)

(ii) Synthesis of dimethylmethylene(cyclopentadienyl)(octamethyloctahydrodibenzofluorenyl)

Into a 200 ml three-necked flask thoroughly purged with nitrogen, equipped with a three-way cock, a dropping funnel and a magnetic stirrer, were introduced octamethyloctahydrodibenzofluorene 3.11 g (8.0 mmol) and dehydrated tetrahydrofuran 40 ml. The contents were stirred by the magnetic stirrer and cooled to 2° C. in an ice bath. 1.63 mol/L n-hexane solution of n-butyllithium, 5.2 ml (8.5 mmol), was added to the mixture over a period of 10 minutes, and stirring was conducted for 21 hours at room temperature outside the ice bath. The slurry was cooled to 0° C. in an ice bath. Then a solution of 6,6-dimethyl fulvene 1.05 ml (8.5 mmol) in 10 ml of dehydrated tetrahydrofuran was added to the slurry over a period of 15 minutes. The mixture was stirred for 23 hours at room temperature outside the ice bath. The resulting solution was quenched by being poured into diluted hydrochloric acid water 100 ml. Soluble matters were extracted with diethyl ether 50 ml, and the fractionated organic phase was washed with a saturated salt solution 100 ml and dried over anhydrous magnesium sulfate. After the magnesium sulfate was filtered off, the solvent of the filtrate was distilled away under reduced pressure. The residual golden yellow solid was purified by column chromatography, so that objective white powder was obtained (2.7 g, 68% yield).

$^1$H NMR spectrum (270 MHz, CDCl$_3$): δ/ppm 1.0 (s+s, 6H), 1.2-1.4 (m, 24H), 1.7 (s, 8H), 3.1-3.2 (s+s, 2H), 4.0 (s+s, 1H), 5.9-7.0 (m, 3H), 6.9 (s, 1H), 7.1 (s, 1H), 7.5 (s, 2H), FD-MS Spectrum: M/z 492 (M$^+$)

(iii) Synthesis of dimethylmethylene($\eta^5$-cyclopentadienyl)($\eta^5$-octamethyloctahydrodibenzofluorenyl)zirconium dichloride Into a 30 ml Schlenk flask thoroughly purged with nitrogen, equipped with a dropping funnel and a magnetic stirrer, were introduced dimethylmethylene(cyclopentadienyl)(octamethyloctahydrodibenzofluorenyl) 0.98 g (2.0 mmol) and dehydrated diethyl ether 20 ml. The contents were stirred by the magnetic stirrer and cooled to 0° C. in an ice bath. 1.63 mol/L n-hexane solution of n-butyllithium, 2.7 ml (4.4 mmol), was added to the mixture over aperiodof 3 minutes, and stirring was conducted for 25 hours at room temperature outside the ice bath. The slurry was cooled to −78° C. in a dry ice/methanol bath. Then a 1:2 complex of zirconium tetrachloride and tetrahydrofuran 0.69g (1.8 mmol) was added to the slurry. The mixture was stirred at room temperature all night (28 hours). After volatile components were distilled away from the slurry under reduced pressure, the residue was washed with dehydrated n-hexane 40 ml. The washing liquid was filtered to obtain a filter cake, from which soluble matters were extracted with dehydrated dichloromethane 10 ml. The extract was distilled under reduced pressure to remove dichloromethane, so that objective red powder was obtained (0.44 g, 37% yield).

$^1$H NMR spectrum (270 MHz, CDCl$_3$): δ/ppm 1.2 (s, 6H), 1.4 (s+s, 12H), 1.5 (s, 6H), 1.7 (s+s, 8H), 2.3 (s, 6H), 4.0 (s+s, 1H), 5.6 (dd, 2H), 6.2 (dd, 2H), 7.6 (s, 2H), 8.0 (s, 2H).

FD-MS Spectrum: M/z 652 (M$^+$)

Example 2

Synthesis of diphenylmethylene($\eta^5$-cyclopentadienyl)($\eta^5$-octamethyloctahydrodibenzofluorenyl)zirconium dichloride (i) Synthesis of diphenylmethylene(cyclopentadienyl)(octamethyloctahydrodibenzofluorenyl)

Into a 200 ml three-necked flask thoroughly purged with nitrogen, equipped with a three-way cock, a dropping funnel and a magnetic stirrer, were introduced octamethyloctahydrodibenzofluorene 2.64 g (6.8 mmol) and dehydrated tetrahydrofuran 40 ml. The contents were stirred by the magnetic stirrer and cooled to 2° C. in an ice bath. 1.63 mol/L n-hexane solution of n-butyllithium, 4.6 ml (7.5 mmol), was added to the mixture over a period of 10 minutes, and stirring was conducted for 23 hours at room temperature outside the ice bath. The slurry was cooled to 1° C. in an ice bath. Then a solution of 6,6-diphenyl fulvene 2.06 g (8.9 mmol) in 20 ml of dehydrated tetrahydrofuran was added to the slurry over a period of 20 minutes. The mixture was stirred for 65 hours at room temperature outside the ice bath. The resulting solution was quenched by being poured into diluted hydrochloric acid water 100 ml. Soluble matterswere extractedwithdiethyl ether 70 ml, and the fractionated organic phase was washed with a saturated salt solution 100 ml and dried over anhydrous magnesium sulfate. After the magnesium sulfate was filtered off, the solvent of the filtrate was distilled away under reduced pressure. The residual golden yellow amorphous was washed with methanol 100 ml and then separated by filtration, so that objective light yellow powder was obtained (3.3 g, 79% yield).

$^1$H NMR spectrum (270 MHz, CDCl$_3$): δ/ppm 0.9-1.5 (m, 24H), 1.6 (s+s, 8H), 3.0 (br, 2H), 5.4 (s+s, 1H), 6.2-6.5 (m(br), 3H), 7.0-7.4 (br+s, 14H), FD-MS Spectrum: M/z 616 (M$^+$).

(ii) Synthesis of diphenylmethylene(η$^5$-cyclopentadienyl)(η$^5$-octamethyloctahydrodibenzofluorenyl)zirconium dichloride Into a 30 ml Schlenk flask thoroughly purged with nitrogen, equipped with a dropping funnel and a magnetic stirrer, were introduced diphenylmethylene(cyclopentadienyl)(octamethyloctahydrodibenzofluorenyl) 0.94 g (1.5 mmol) and dehydrated diethyl ether 15 ml. The contents were stirred by the magnetic stirrer and cooled to 0° C. in an ice bath. 1.63 mol/L n-hexane solution of n-butyllithium, 2.1 ml (3.4 mmol), was added to the mixture, and stirring was conducted for 22 hours at room temperature outside the ice bath. The slurry was cooled to −78° C. in a dry ice/methanol bath. Then a 1:2 complex of zirconium tetrachloride and tetrahydrofuran 0.55 g (1.5 mmol) was added to the slurry. The mixture was stirred at room temperature all night (45 hours). After volatile components were distilled away from the slurry under reduced pressure, the residue was washed with dehydrated n-hexane 40 ml. Insoluble matters were filtered off, and an auburn filtrate was subjected to recrystallization to obtain objective red powder (0.4 g, 36% yield).

$^1$H NMR spectrum (270 MHz, CDCl$_3$) : δ/ppm 0.8 (s, 6H) , 0.9 (s, 6H), 1.4 (s, 6H), 1.5 (s, 6H), 1.6-1.7 (m, 8H), 5.6 (dd, 2H) , 6.2 (s, 2H) , 6.3 (dd, 2H), 7.3-7.5 (m, 6H), 7.9 (d, 2H), 8.0 (d, 2H), 8.1 (s, 2H), FD-MS Spectrum: M/z 776 (M$^+$).

Example 3

Synthesis of cyclohexylidene(η$^5$-cyclopentadienyl) (η$^5$-octamethyloctahydrodibenzofluorenyl)zirconium dichloride (i) Synthesis of cyclohexylidene(cyclopentadienyl)(octamethyloctahydrodibenzofluorenyl)

Into a 100 ml branched flask thoroughly purged with nitrogen, equipped with a dropping funnel and a magnetic stirrer, were introduced octamethyloctahydrodibenzofluorene 0.73 g (1.9 mmol) and dehydrated tetrahydrofuran 20 ml. The contents were stirred by the magnetic stirrer and cooled in an ice bath. 1.58 mol/L n-hexane solution of n-butyllithium, 1.3 ml (2.1 mmol), was dropwise added to the mixture, and stirring was conducted for 27 hours at room temperature outside the ice bath. The slurry was cooled in an ice bath. Then a solution of 6,6-cyclohexyl fulvene 0.31 g (2.1 mmol) in 10 ml of dehydrated tetrahydrofuran was dropwise added to the slurry. The mixture was stirred for 17 hours at room temperature outside the ice bath. The resulting solution was quenched by being poured into diluted hydrochloric acid solution 50 ml. Soluble matters were extracted with diethyl ether 50 ml, and the fractionated organic phase was washed with a saturated salt solution 50 ml and dried over anhydrous magnesium sulfate. After the magnesium sulfate was filtered off, the solvent of the filtrate was distilled away under reduced pressure. The residue was purified by column chromatography, so that an objective yellow solid was obtained (0.63 g, 63% yield).

$^1$H NMR spectrum (270 MHz, CDCl$_3$): δ/ppm 1.2-1.4 (m, 24H), 1.4-1.7 (m, 6H), 1.71 (s, 8H), 1.8-1.9 (m, 4H), 2.3-3.1 (s+s+s, 2H), 3.8 (s+s, 1H), 5.9-6.0 (m+m, 1H), 6.4-6.6 (m+m+m, 1H), 7.0-7.2 (m, 2H), 7.5 (s, 2H).

(ii) Synthesis of cyclohexylidene(η$^5$-cyclopentadienyl)(η$^5$-octamethyloctahydrodibenzofluorenyl)zirconium dichloride Into a 100 ml branched flask thoroughly purged with nitrogen, equipped with a dropping funnel and a magnetic stirrer, were introduced cyclohexylidene(cyclopentadienyl)(octamethyloctahydrodibenzofluorenyl) 0.50 g (0.94 mmol) and dehydrated diethyl ether 50 ml. The contents were stirred by the magnetic stirrer and cooled to 0° C. in an ice bath. 1.58 mol/L n-hexane solution of n-butyllithium, 1.2 ml (1.9 mmol), was added to the mixture, and stirring was conducted for 16 hours at room temperature outside the ice bath. The slurry was cooled to −78° C. in a dry ice/methanol bath. Then a 1:2 complex of zirconium tetrachloride and tetrahydrofuran 0.31 g (0.84 mmol) was added to the slurry. The mixture was stirred at room temperature all night. After volatile components were distilled away from the slurry under reduced pressure, the residue was washed with dehydrated n-hexane. The washing liquid was filtered to obtain a filter cake, from which soluble matters were extracted with dehydrated dichloromethane. The extract was distilled under reduced pressure to remove dichloromethane, so that objective tangerine powder was obtained (0.05 g, 9% yield).

$^1$H NMR spectrum (270 MHz, CDCl$_3$): δ/ppm 1.2-1.4 (m, 24H), 1.71 (s, 8H), 1.8-1.9 (m, 4H), 2.4-2.5 (m, 2H), 3.1-3.3 (m, 2H), 3.6-3.7 (m, 2H), 4.3 (dd, 1H), 5.0 (dd, 1H), 5.3 (dd, 1H), 6.2 (dd, 1H), 7.1 (s, 1H), 7.2 (s, 1H), 7.5 (s, 1H), 8.0 (s, 1H), FD-MS Spectrum: M/z 692 (M$^+$)

Example 4

Synthesis of dimethylsilylene(η$^5$-cyclopentadienyl) (η$^5$-octamethyloctahydrodibenzofluorenyl)zirconium dichloride (i) Synthesis of chlorodimethyl(octamethyloctahydrodibenzofluorenyl)silane A 300 ml two-necked flask equipped with a three-way cock, a dropping funnel and a magnetic stirrer, was thoroughly purged with nitrogen. Octamethyloctahydrodibenzofluorene 2.50 g (6.47 mmol) was placed in the flask and dissolved by addition of a mixed solvent consisting of dehydrated diethyl ether 30 ml and dehydrated tetrahydrofuran 150 ml. With cooling in an ice bath, 1.64 mol/L n-hexane solution of n-butyllithium, 4.06 ml (6.66 mmol) , was added to the solution, and the mixture was stirred in a nitrogen atmosphere at room temperature for 2 days. After the solvent was distilled away under reduced pressure, dehydrated diethyl ether 50 ml was added to obtain a slurry. Separately, dehydrated n-hexane 100 ml and dichlorodimethylsilane 7.8 ml (64.7 mmol) were introduced into a 300 ml four-necked flask thoroughly purged with nitrogen, which was equipped with a three-way cock, a dropping funnel and a magnetic stirrer. With the flask cooled in a dry ice/methanol bath, the slurry was dropwise added over a period of 1 hour by means of the dropping funnel. While allowing the liquid temperature to rise gradually to room temperature, the contents were stirred for 1 day in a nitrogen atmosphere. The resulting slurry was filtered to remove solids, and the solvent of the filtrate was distilled away under reduced pressure to obtain a yellow solid 3.56 g. According to the $^1$HNMR spectrum, the yellow solid was confirmed to be a mixture of chlorodimethyl(octamethyloctahydrodibenzofluorenyl)silane and octamethyloctahydrodibenzofluorene in an approximate ratio of 1:1.3. The $^1$H NMR spectrum as measured with respect to the chlorodimethyl(octamethyloctahydrodibenzofluorenyl)silane is given below:

$^1$H NMR spectrum (270 MHz, CDCl$_3$): δ/ppm 0.14 (s, Si—Me, 6H), 1.31 (s, Me(OMOHDBFlu), 6H), 1.32 (s, Me(OMOHDBFlu), 6H), 1.37 (s, Me(OMOHDBFlu), 6H), 1.38 (s, Me(OMOHDBFlu), 6H), 1.72 (s, CH$_2$(OMOHDB-Flu), 8H), 3.89 (s, 9-H(OMOHDBFlu), 1H), 7.52 (s, CH(O-MOHDBFlu), 2H), 7.69 (S, CH(OMOHDBFlu), 2H).

(ii) Synthesis of cyclopentadienyldimethyl(octamethyloctahydrodibenzofluorenyl)silane A 300 ml two-necked flask equipped with a three-way cock, a dropping funnel and a magnetic stirrer, was thoroughly purged with nitrogen. The yellow solid (the mixture of chlorodimethyl(octamethyloctahydrodibenzofluorenyl)silane and octamethyloctahydrodibenzofluorene) 3.56 g obtained in above (i) and copper thiocyanate 47 mg (0.39 mmol) were placed in the flask, and dehydrated diethyl ether 90 ml was further added. With the flask cooled in a dry ice/methanol bath, 2.0 mol/L tetrahydrofuran solution of cyclopentadienyl sodium, 1.8 ml (3.6 mmol), was added. After the liquid temperature was gradually raised to room temperature, the contents were stirred for 1 day in a nitrogen atmosphere at room temperature. Addition of a saturated aqueous solution of ammonium chloride 100 ml caused precipitation of solids, which were then removed by filtration. The water phase was removed by means of a separatory funnel. The organic phase thus obtained was washed twice with water 100 ml and twice with a saturated salt solution 100 ml, and dried over anhydrous magnesium sulfate. The solvent was distilled away to obtain a solid. As a result of separation by silica gel column chromatography, 1.39 g of octamethyloctahydrodibenzofluorene was recovered (3.60 mmol, 55.6% yield), and 0.47 g of a white solid, cyclopentadienyldimethyl(octamethyloctahydrodibenzofluorenyl)silane, was obtained (0.92 mmol, 14.2% yield (in terms of octamethyloctahydrodibenzofluorene)).

The $^1$H NMR spectrum and the FD-MS spectrum as measured with respect to the cyclopentadienyldimethyl(octamethyloctahydrodibenzofluorenyl)silane are given below:

$^1$H NMR spectrum (270 MHz, CDCl$_3$): δ/ppm −0.16 (s, Si—Me, 6H), 1.2-1.5 (m, Me(OMOHDBFlu), 24H), 1.70-1.73 (m, CH$_2$(OMOHDBFlu), 8H), 3.74-3.76 (m, 9-H (OMOHDBFlu), 1H), 5.8-6.7 (m, Cp, 4H), 7.1-7.8 (m, CH(OMOHDBFlu), 4H), FD-MS Spectrum: M/z 508 (M$^+$)

(iii) Synthesis of dimethylsilylene(5-cyclopentadienyl)(η$^5$-octamethyloctahydrodibenzofluorenyl)zirconium dichloride A 100 ml Kjeldahl flask equipped with a dropping funnel and a magnetic stirrer, was thoroughly purged with nitrogen. Cyclopentadienyldimethyl(octamethyloctahydrodibenzofluorenyl)silane 0.47 g (0.92 mmol) was placed in the flask and dissolved by addition of dehydrated diethyl ether 40 ml. With cooling in an ice bath, 1.64 mol/L n-hexane solution of n-butyllithium, 1.17 ml (1.92 mmol), was added to the solution, and the mixture was stirred in a nitrogen atmosphere at room temperature for 26 hours. Thereafter, with the flask cooled in a dry ice/methanol bath, a 1:2 complex of zirconium tetrachloride and tetrahydrofuran 0.315 g (0.835 mmol) was added. While allowing the liquid temperature to rise gradually to room temperature, the contents were stirred for 23 hours. After the solvent was distilled away, the residue was extracted with dehydrated n-hexane 10 ml and dehydrated dichloromethane 40 ml. Then the solvent was distilled away and the resulting solid was dissolved in dichloromethane. Dehydrated n-hexane was poured over the dichloromethane solution, and recrystallization was effected at about −20° C. to obtain 191 mg of dimethylsilylene(η$^5$-cyclopentadienyl) (η$^5$-octamethyloctahydrodibenzofluorenyl)zirconium dichloride as a tangerine solid (0.286 mmol, 34.2% yield). The $^1$H NMR spectrum and the FD-MS spectrum as measured with respect to the dimethylsilylene(η$^5$-cyclopentadienyl)(η$^5$-octamethyloctahydrodibenzofluorenyl)zirconium dichloride are given below:

$^1$H NMR spectrum (270 MHz, CDCl$_3$): η/ppm 1.08 (s, Si—Me, 6H), 1.21 (s, Me(OMOHDBFlu), 6H), 1.35 (s, Me(OMOHDBFlu), 6H), 1.39 (s, Me(OMOHDBFlu), 6H), 1.49 (s, Me(OMOHDBFlu), 6H), 1.72 (s, CH$_2$Me(OMOHDBFlu), 8H), 5.55 (t, J=2.3 Hz, Cp, 2H), 6.53 (t, J=2.3 Hz, Cp, 2H), 7.33 (s, CH(OMOHDBFlu), 2H), 7.98 (s, CH(OMOHDBFlu), 2H), FD-MS spectrum: M/z 668 (M$^+$)

Example 5

Synthesis of diphenylsilylene(η$^5$-cyclopentadienyl) (η$^5$-octamethyloctahydrodibenzofluorenyl)zirconium dichloride (i) Synthesis of chloro (octamethyloctahydrodibenzofluorenyl)diphenyl silane Into a 200 ml two-necked flask equipped with a three-way cock, a dropping funnel and a magnetic stirrer, was introduced octamethyloctahydrodibenzofluorene 1.01 g (2.60 mmol), and dissolved by addition of dehydrated diethyl ether 65 ml. With cooling in an ice bath, 1.61 mol/L n-hexane solution of n-butyllithium, 1.7 ml (2.74 mmol), was added to the solution, and the mixture was stirred in a nitrogen atmosphere at room temperature for 23 hours to give a slurry. Separately, dehydrated n-hexane 130 ml and dichlorodiphenylsilane 0.6 ml (2.85 mmol) were introduced into a 500 ml four-necked flask equipped with a three-way cock, a dropping funnel and amagnetic stirrer. With the flask cooled in a dry ice/methanol bath, the slurry was dropwise added over a period of 50 minutes by means of the dropping funnel. While allowing the liquid temperature to rise gradually to room temperature, the contents were stirred for 18 hours. The resulting slurry was filtered to remove solids, and the solvent of the filtrate was distilled away under reduced pressure to obtain a yellow solid 1.79 g. According to the $^1$H NMR spectrum, the yellow solid was confirmed to be a mixture mainly composed of chloro (octamethyloctahydrodibenzofluorenyl) diphenyl silane. The $^1$H NMR spectrum as measured with respect to the chloro (octamethyloctahydrodibenzofluorenyl)diphenyl silane is given below:

$^1$H NMR spectrum (270 MHz, CDCl$_3$): δ/ppm 1.03 (s, Me(OMOHDBFlu), 6H), 1.14 (s, Me(OMOHDBFlu), 6H), 1.30 (s, Me(OMOHDBFlu), 6H), 1.31 (s, Me(OMOHDBFlu), 6H), 1.65 (s, CH$_2$(OMOHDBFlu), 8H), 4.39 (s, 9-H (OMOHDBFlu), 1H), 7.1-7.8 (m, CH(Ph and OMOHDBFlu), 14H).

(ii) Synthesis of cyclopentadienyl(octamethyloctahydrodibenzofluorenyl)diphenyl silane A 300 ml two-necked flask equipped with a three-way cock, a dropping funnel and a magnetic stirrer, was thoroughly purged with nitrogen. The yellow solid 1.79 g, which contains chloro(octamethyloctahydrodibenzofluorenyl) diphenyl silane obtained in above (i), dehydrated diethyl ether 30 ml and hexamethylphosphoric triamide 3 ml were placed in the flask. With the flask cooled in an ice bath, a tetrahydrofuran solution of 2 mol/L of cyclopentadienyl sodium, 2.6 ml (5.2 mmol), was added. The contents were stirred for 21 hours in a nitrogen atmosphere at room temperature. After addition of a saturated aqueous solution of ammonium chloride 50 ml, the water phase was removed by means of a separatory funnel. The organic phase thus obtained was washed five times with water 50 ml and dried over anhydrous magnesium sulfate. The solution was filtered to remove the magnesium sulfate, and the solvent of the filtrate was distilled away to obtain a solid. The solid was dissolved in a small amount of n-hexane, and recrystallization was effected at about −15° C. to obtain 0.496 g of cyclopentadienyl(octamethyloctahydrodibenzofluorenyl)diphenyl silane as a yellowish white solid (0.783 mmol, 30.0% yield (in terms of octamethyloctahydrodibenzofluorenyl)). The $^1$H NMR spectrum and the FD-MS spectrum as measured with respect to the cyclopentadienyl(octamethyloctahydrodibenzofluorenyl)diphenyl silane are given below:

$^1$H NMR spectrum (270 MHz, CDCl$_3$): δ/ppm 0.93 (s, Me(OMOHDBFlu), 6H), 1.02 (s, Me(OMOHDBFlu), 6H), 1.33 (s, Me(OMOHDBFlu), 6H), 1.35 (s, Me(OMOHDBFlu), 6H), 1.65 (m, CH$_2$(OMOHDBFlu), 8H), 4.37 (s, 9-H (OMOHDBFlu), 1H), 6.3-6.7 (m, CH(Cp), 4H), 7.1-7.7 (m, CH(Ph and OMOHDBFlu), 14H), FD-MS Spectrum: M/z 633 (M$^+$+1)

(iii) Synthesis of diphenylsilylene(η$^5$-cyclopentadienyl)(η$^5$-octamethyloctahydrodibenzofluorenyl)zirconium dichloride A 100 ml Kjeldahl flask equipped with a dropping funnel and a magnetic stirrer, was thoroughly purged with nitrogen. Cyclopentadienyl(octamethyloctahydrodibenzofluorenyl) diphenyl silane 0.339 g (0.535 mmol) was placed in the flask and dissolved by addition of dehydrated diethyl ether 30 ml. With cooling in an ice bath, 1.61 mol/L n-hexane solution of n-butyllithium, 0.7 ml (1.13 mmol), was added to the solution, and the mixture was stirred at room temperature for 22 hours. With the flask cooled in a dry ice/methanol bath, a 1:2 complex of zirconium tetrachloride and tetrahydrofuran 0.200 g (0.529 mmol) was added. While allowing the liquid temperature to rise gradually to room temperature, the contents were stirred for 24 hours. After the solvent was distilled away, the residual solid was washed with a small amount of dehydrated n-hexane. Thereafter extraction was made with dehydrated dichloromethane, and the solvent was distilled away to obtain 273 mg of diphenylsilylene(η$^5$-cyclopentadienyl)(η$^5$-octamethyloctahydrodibenzofluorenyl)zirconium dichloride as an orange solid (0.344 mmol, 64.3% yield). The $^1$H NMR spectrum and the FD-MS spectrum as measured with respect to the diphenylsilylene(η$^5$-cyclopentadienyl) (η$^5$-octamethyloctahydrodibenzofluorenyl)zirconium dichloride are given below:

$^1$H NMR spectrum (270 MHz, CDCl$_3$): δ/ppm 0.78 (s, Me(OMOHDBFlu), 6H), 0.89 (s, Me(OMOHDBFlu), 6H), 1.37 (s, Me(OMOHDBFlu), 6H), 1.45 (s, Me(OMOHDBFlu), 6H), 1.61 (m, CH$_2$(OMOHDBFlu), 8H), 5.73 (t, J=2.3 Hz, Cp, 2H), 6.58 (s, CH(OMOHDBFlu), 2H), 6.63 (t, J=2.3 Hz, Cp, 2H), 6.3-6.7 (m, CH(Cp), 4H), 7.5-7.6 (m, CH(Ph), 6H), 7.97 (s, CH(OMOHDBFlu), 2H), 8.1-8.2 (m, CH(Ph), 4H), FD-MS Spectrum: M/z 792 (M$^+$)

Example 6

Synthesis of dicyclohexylsilylene(η$^5$-cyclopentadienyl){η$^5$-(2,7-di-tert-butylfluorenyl)}zirconium dichloride (i) Synthesis of chlorodicyclohexyl(2,7-di-tert-butylfluorenyl)silane A 300 ml two-necked flask equipped with a three-way cock, a dropping funnel and a magnetic stirrer, was thoroughly purged with nitrogen. Into the flask was introduced 2,7-di-tert-butylfluorene 3.01 g (10.81 mmol), and dissolved by addition of dehydrated diethyl ether 60 ml. With cooling in an ice bath, 1.56 mol/L n-hexane solution of n-butyllithium, 6.9 ml (11.0 mmol), was added to the solution, and the mixture was stirred in a nitrogen atmosphere at room temperature for 20 hours. Separately, a 500 ml three-necked flask equipped with a 100 ml dropping funnel, a three-way cock and a magnetic stirrer was thoroughly purged with nitrogen, and dehydrated n-hexane 120 ml and dichlorodicyclohexylsilane 2.6 ml (11.0 mmol) were introduced into the flask. With the flask cooled in a dry ice/methanol bath, the above-prepared solution was dropwise added over a period of 1 hour by means of the dropping funnel. While allowing the liquid temperature to rise gradually to room temperature, the contents were stirred for 3 days in a nitrogen atmosphere. The resulting slurry was filtered to remove solids, and the solvent of the filtrate was distilled away under reduced pressure to obtain 5.5 g of chlorodicyclohexyl(2,7-di-tert-butylfluorenyl)silane as a light yellow solid (11.0 mmol, 100% yield). The $^1$H NMR spectrum as measured with respect to the chlorodicyclohexyl(2,7-di-tert-butylfluorenyl)silane is given below:

$^1$H NMR spectrum (270 MHz, CDCl$_3$): δ/ppm 0.6-1.9 (m, cyclohexyl, 22H) , 1.36 (s, t-Bu, 18H), 4.13 (s, CH(9-Flu) , 1H), 7.3-7.4 (m, Flu, 2H), 7.6-7.8 (m, Flu, 4H).

(ii) Synthesis of dicyclohexylcyclopentadienyl(2,7-di-tert-butylfluorenyl)silane A 300 ml two-necked flask equipped with a three-way cock, a dropping funnel and a magnetic stirrer, was thoroughly purged with nitrogen. The above-obtained chlorodicyclohexyl(2,7-di-tert-butylfluorenyl)silane 5.5 g (11.0 mmol) and dehydrated diethyl ether 30 ml were placed in the flask. Hexamethylphosphoric triamide 3.0 ml was further added. With the flask cooled in an ice bath, 2.0 mol/L tetrahydrofuran solution of cyclopentadienyl sodium, 11.0 ml (22.0 mmol), was gradually added. After the liquid temperature was slowly raised to room temperature, the contents were stirred for 2 days in a nitrogen atmosphere at room temperature to give a slurry. To the slurry, 1 N hydrochloric aqueous solution acid 100 ml was added, and the water phase was removed by means of a 300 ml separatory funnel. The organic phase thus obtained was washed twice with water 100 ml and once with a saturated salt solution 100 ml, and dried over anhydrous magnesium sulfate. The solution was filtered to remove the magnesium sulfate, and the solvent of the filtrate was distilled away to obtain a solid. The solid was washed with n-hexane and then dried to give 1.514 g of dicyclohexylcyclopentadienyl(2,7-di-tert-butylfluorenyl)silane as a white solid (2.82 mmol, 26% yield). The $^1$H NMR spectrum and the FD-MS spectrum as measured with respect to the dicyclohexylcyclopentadienyl(2,7-di-tert-butylfluorenyl)silane are given below:

$^1$H NMR spectrum (270 MHz, CDCl$_3$): δ/ppm 0.5-1.8 (m, cyclohexyl, 22H), 1.26 and 1.29 and 1.35 (s, t-Bu, 18H), 2.9-3.2 (m, CH$_2$(Cp), 2H), 4.06 and 4.14 and 4.21 (s, CH(9-Flu), 1H), 6.5-6.9 (m, CH(Cp), 3H), 7.2-7.8 (m, Flu, 6H), FD-MS Spectrum: M/z 536 (M$^+$)

(iii) Synthesis of dicyclohexylsilylene(η$^5$-cyclopentadienyl) {η$^5$-(2,7-di-tert-butylfluorenyl)}zirconium dichloride A 100 ml Kjeldahl flask equipped with a dropping funnel and a magnetic stirrer, was thoroughly purged with nitrogen. Dicyclohexylcyclopentadienyl(2,7-di-tert-butylfluorenyl)silane 453 mg (0.843 mmol) was placed in the flask, and dehydrated diethyl ether 30ml was further added. With cooling in an ice bath, 1.56 mol/L n-hexane solution of n-butyllithium, 1.12 ml (1.75 mmol), was gradually added to the solution, and the mixture was stirred at room temperature in a nitrogen atmosphere for 20 hours to give a slurry. With the flask cooled in a dry ice/methanol bath, a 1:2 complex of zirconium tetrachloride and tetrahydrofuran 0.374 g (0.992 mmol) was added. The liquid temperature was slowly raised to room temperature, and the contents were stirred for 3 days in a nitrogen atmosphere at room temperature to give a slurry. After the solvent was distilled away under reduced pressure, the residual solid was extracted with dehydrated n-hexane. The n-hexane solution was subjected to recrystallization at about −20° C. to obtain 0.246 g of dicyclohexylsilylene($\eta^5$-cyclopentadienyl){$\eta^5$-(2,7-di-tert-butylfluorenyl)}zirconium dichloride as a yellow solid (0.353 mmol, 42% yield). Identification of the dicyclohexylsilylene($\eta^5$-cyclopentadienyl){$\eta^5$(2,7-di-tert-butylfluorenyl)}zirconium dichloride was made by $^1$H NMR and the FD-mass spectrometric analysis, the results being given below:

$^1$H NMR spectrum (270 MHz, CDCl$_3$): δ/ppm 1.1-2.4 (m, cyclohexyl, 22H), 1.36 (s, t-Bu, 18H), 5.64 (t, J=2.3 Hz, Cp, 2H), 6.55 (t, J=2.3 Hz, Cp, 2H), 7.46 (d, J=1.6 Hz, CH(Flu), 2H), 7.59 (dd, J=8.6 Hz, J=1.6 Hz, CH(Flu), 2H), 7.98 (d, J=8.6 Hz, CH(Flu), 2H), FD-MS Spectrum: M/z 696 (M$^+$)

Example 7

Synthesis of cyclohexylidene($\eta^5$-cyclopentadienyl){$\eta^5$-(3,6-di-tert-butylfluorenyl)}zirconium dichloride (i) Synthesis of 1-cyclopentadienyl-1'-(3,6-di-tert-butylfluorenyl)cyclohexane Into a 200 ml Kjeldahl flask thoroughly purged with nitrogen, equipped with a dropping funnel and a magnetic stirrer, was introduced 3,6-di-tert-butylfluorene 0.66 g (2.36 mmol), and dehydrated tetrahydrofuran 10 ml was further added. With cooling in an ice bath, 1.58 mol/L n-hexane solution of n-butyllithium, 1.64 ml (2.59 mmol), was dropwise added to the solution, and the mixture was stirred at room temperature for 6 hours. With the flask cooled in an ice bath, a solution of cyclohexyl fulvene 0.38 g (2.60 mmol) in 5 ml of dehydrated tetrahydrofuran, was dropwise added into the flask. After the contents were stirred for 15 hours at room temperature, 1 N hydrochloric acid aqueous solution 30 ml was gradually added, and stirring was further conducted for about 10 minutes. The reaction solution was poured into a separatory funnel, and extraction was made with ether 20 ml. The organic phase was fractionated, washed with a saturated salt solution 30ml and dried over anhydrous magnesium sulfate. The solution was filtered to remove the magnesium sulfate, and the solvent of the filtrate was distilled away to obtain a solid. The solid was washed with n-hexane and ether, and then dried to give an objective yellowish white solid (0.75 g, 72% yield). The $^1$H NMR spectrum and the FD-MS spectrum as measured with respect to the solid are given below:

$^1$H NMR spectrum (270 MHz, CDCl$_3$): δ/ppm 1.38 (s, t-Bu(Flu)), 1.4-1.7 (m, CH$_2$(C6)), 1.83 (bs, CH$_2$(C6)), 1.87 (bs, CH$_2$(C6)) , 2.81 (s, CH$_2$(Cp)) , 3.02 (s, CH$_2$(Cp)) , 3.85 (s, CH(Flu)), 5.9-6.0 (m×2, CH(Cp)), 6.3-6.6 (m×3, CH(Cp)), 7.1-7.3 (m, CH(Flu)), 7.66 (d, J=1.4 Hz, CH(Flu)), FD-MS Spectrum: M/z 424 (M$^+$).

(ii) Synthesis of cyclohexylidene($\eta^5$-cyclopentadienyl){$\eta^5$(3,6-di-tert-butylfluorenyl)}zirconium dichloride Into a 100 ml Kjeldahl flask purged thoroughly with nitrogen, equipped with a dropping funnel and a magnetic stirrer, was introduced 1-cyclopentadienyl-1'-(3,6-di-tert-butylfluorenyl)cyclohexane 0.50 g (1.18 mmol), and dehydrated ether 50 ml was further added. With cooling in ice bath, 1.58 mol/L n-hexane solution of n-butyllithium, 1.53 ml (2.42 mmol), was dropwise added to the solution, and the mixture was stirred at room temperature for 27 hours. With the flask cooled to nearly −78° C. in a dry ice/methanol bath, a 1:2 complex of zirconium tetrachloride and tetrahydrofuran 0.41 g (1.08 mmol) was added. The liquid temperature was slowly raised to room temperature overnight. The solvent was dried out, and n-hexane soluble components were removed by addition of dehydrated n-hexane. Then soluble components were extracted with dehydrated methylene chloride, and the solvent was distilled away. The residue was dried under reduced pressure to give an objective vermilion solid (0.35 g, 56% yield). The $^1$H NMR spectrum and the FD-MS spectrum as measured with respect to the solid are given below:

$^1$H NMR spectrum (270 MHz, CDCl$_3$): δ/ppm 1.44 (s, t-Bu(Flu)), 1.6-1.9 (m, CH$_2$(C6)), 2.2-2.3 (m, CH$_2$(C6)), 3.24 (bs, CH$_2$(C6)), 3.29 (bs, CH$_2$(C6)), 5.70 (t, J=2.7 Hz, CH(Cp)), 6.27 (t, J=2.7 Hz, CH(Cp)), 7.33 (d, J=2.2 Hz, CH(Flu)), 7.37 (d, J=1.6 Hz, CH(Flu)) , 7.62 (s, CH$_2$(Flu)), 7.66 (s, CH$_2$ (Flu)), 8.04 (d, J=1.6 Hz, CH(Flu)), FD-MS Spectrum: M/z 584 (M$^+$).

Example 8

Synthesis of dibenzylmethylene{$\eta^5$-(cyclopentadienyl)($\eta^5$-fluorenyl)}zirconium dichloride (otherwise, 1,3-diphenylisopropylidene($\eta^5$-cyclopentadienyl) ($\eta^5$fluorenyl)zirconium dichloride)

(i) Synthesis of 6,6-dibenzyl fulvene

Into a 100 ml Kjeldahl flask purged thoroughly with nitrogen, equipped with a dropping funnel and a magnetic stirrer, were introduced cyclopentadiene 2.40 g (36.2 mmol) which had been subjected to cracking, and dehydrated tetrahydrofuran 50 ml. With cooling in an ice bath, 1.57 mol/L n-hexane solution of n-butyllithium, 24.3 ml (38.1 mmol), was dropwise added to the solution by means of the dropping funnel. The resulting slurry was stirred all night at room temperature. With the flask cooled in an ice bath, a solution of dibenzyl ketone 9.16 g (43.6 mmol) in 20 ml of dehydrated tetrahydrofuran, was dropwise added into the flask by means of the dropping funnel. The resulting slurry was stirred all night at room temperature. After addition of a saturated aqueous solution of ammonium chloride 50 ml and ether 50 ml, the organic phase was recovered with a separatory funnel. The water phase was extracted with ether 30 ml. The organic phase was washed twice with water 50 ml and once with a saturated salt solution 50 ml, and dried over magnesium sulfate. The solution was filtered to remove the magnesium sulfate, and the solvent of the filtrate was distilled away to obtain a solid. The residue was subjected to column chromatography to obtain an objective brown oil in 1.10 g (12%) yield. The $^1$H NMR spectrum and the FD-MS spectrum as measured with respect to the brown oil are given below:

$^1$H NMR spectrum (270 MHz, CDCl$_3$): δ/ppm 3.71 (s, CH$_2$, 4H), 6.6-6.7 (m, Cp, 4H), 7.1-7.4 (m, Ph, 10H), FD-MS Spectrum: M/z 258 (M$^+$).

(ii) Synthesis of dibenzylmethylene(cyclopentadienyl)(fluorenyl)methane (otherwise, 2-cyclopentadienyl-2-{9-(fluorenyl)}-1,3-diphenyl propane)

Into a 100 ml Kjeldahl flask purged thoroughly with nitrogen, equipped with a dropping funnel and a magnetic stirrer, were introduced fluorene 0.64 g (3.85 mmol) and dehydrated tetrahydrofuran 40 ml. With cooling in an ice bath, 1.57 mol/L n-hexane solution of n-butyllithium, 2.70 ml (4.24 mmol), was dropwise added by means of the dropping funnel. The resulting slurry was stirred all night at room temperature. With the flask cooled in an ice bath, a solution of 6,6-dibenzyl fulvene 1.10 g (4.22 mmol) in 30 ml of dehydrated tetrahydrofuran, was dropwise added by means of the dropping funnel. The resulting slurry was stirred for 1 hour at room temperature. After addition of 1 N hydrochloric acid aqueous solution 50 ml and ether 50 ml, the organic phase was recovered by means of a separatory funnel. The organic phase was washed once with a saturated salt solution 50 ml and once with water 50 ml, and dried over magnesium sulfate. The solution was filtered to remove the magnesium sulfate, and the solvent of the filtrate was distilled away to obtain a solid. The solid was washed with n-hexane and methanol, and then dried to give an objective white solid (0.68 g, 42% yield). The $^1$H NMR spectrum as measured with respect to the white solid is given below:

$^1$H NMR spectrum (270 MHz, CDCl$_3$): δ/ppm 6.9-7.6 (m>17, CH(Flu, Ph)), 5.9-6.4 (m×5, CH(Cp)), 4.6 (s×2, CH(Flu)), 3.3 (s×2, CH$_2$(Et)), 2.9 (s, CH$_2$(CP)), 2.7 (s, CH$_2$ (Cp)).

(iii) Synthesis of dibenzylmethylene($\eta^5$-cyclopentadienyl)($\eta^5$-fluorenyl)zirconium dichloride (otherwise, 1,3-diphenylisopropylidene($\eta^5$-cyclopentadienyl)($\eta^5$-fluorenyl)zirconium dichloride)

Into a 100 ml Kjeldahl flask purged thoroughly with nitrogen, equipped with a dropping funnel and a magnetic stirrer, was introduced dibenzylmethylene(cyclopentadienyl)(fluorenyl)methane 0.60 g (1.41 mmol), and dehydrated ether 70 ml was further added. With cooling in an ice bath, 1.57 mol/L n-hexane solution of n-butyllithium, 1.90 ml (2.98 mmol), was dropwise added to the solution. The mixture was stirred all night at room temperature. With the flask cooled to nearly −78° C. in a dry ice/methanol bath, a 1:2 complex of zirconium tetrachloride and tetrahydrofuran 0.48 g (1.27 mmol) was added. The liquid temperature was slowly raised to room temperature overnight. After the solvent was distilled away, the residual solid was washed with dehydrated n-hexane to remove n-hexane soluble components. Then components soluble in dehydrated ether were removed, and the residue was extracted with dehydrated toluene. After the solvent was distilled away, the remainder was subjected to recrystallization with dehydrated toluene, so that an objective red solid was obtained (59 mg, 8% yield). The $^1$H NMR spectrum and the FD-MS spectrum as measured with respect to the red solid are given below:

$^1$H NMR spectrum (270 MHz, CDCl$_3$): δ/ppm 8.1 (d, 8.4 Hz, CH(Flu)), 7.8 (d, 8.9 Hz, CH(Flu)), 7.5 (t, 8.4 Hz, CH(Flu), 7.0-7.2 (m>8, CH(Ph)), 6.4 (t, 2.7 Hz, CH(Cp)), 5.9 (t, 2.7 Hz, CH(Cp)), 4.0-4.2 (s×4, CH$_2$(Et)), FD-MS Spectrum: M/z 584 (M$^+$).

Example 9

Synthesis of dibenzylmethylene($\eta^5$-cyclopentadienyl)($\eta^5$-octamethyloctahydrodibenzofluorenyl)zirconium dichloride (otherwise, 1,3-diphenylisopropylidene($\eta^5$-cyclopentadienyl)($\eta^5$-octamethyloctahydrodibenzofluorenyl)zirconium dichloride)

(i) Synthesis of dibenzylmethylene(cyclopentadienyl)(octamethyloctahydrodibenzofluorenyl)methane (otherwise, 2-cyclopentadienyl-2-(9-octamethyloctahydrodibenzofluorenyl)-1,3-diphenyl propane)

Into a 200 ml three-necked flask purged thoroughly with nitrogen, equipped with a magnetic stirrer, a three-way cock and a dropping funnel, was introduced octamethyloctahydrodibenzofluorene 1.41 g (3.65 mmol), and dissolved by addition of dehydrated tetrahydrofuran 50 ml. With cooling in an ice bath, 1.59 mol/L n-hexane solution of n-butyllithium, 2.40 ml (3.82 mmol), was added into the flask. The resulting solution was stirred for 24 hours at room temperature. With the flask cooled in a dry ice/methanol bath, a solution of 6,6-dibenzyl fulvene 1.06 g (4.10 mmol) in 20 ml of dehydrated tetrahydrofuran, was dropwise added by means of the dropping funnel. Then the liquid temperature was gradually raised to room temperature, and the contents were stirred for 3 days at the temperature. After addition of 1 N hydrochloric acid aqueous solution 50 ml, the organic phase was collected by a separatory funnel. The obtained organic phase was washed twice with water 50 ml and once with a saturated salt solution 50 ml, and dried over anhydrous magnesium sulfate. The solution was filtered to remove the magnesium sulfate, and the solvent of the filtrate was distilled away. The residue was purified with silica gel column chromatography to obtain an objective light yellow solid (0.34 g, 14% yield). The $^1$H NMR spectrum as measured with respect to the solid is given below:

$^1$H NMR spectrum (270 MHz, CDCl$_3$): δ/ppm 1.1-1.4 (m, C—Me(OMOHDBFlu)), 1.67 (s, CH$_2$(OMOHDBFlu)), 2.93 (s, CH$_2$(Cp)), 3.01 (d, J=1.3 Hz, CH$_2$ (Cp)), 3.20 (s, CH$_2$ (benzyl)), 4.38 (s, CH(OMOHDBFlu)), 4.42 (s, CH(OMOHDBFlu)), 5.9-6.6 (m×5, CH(Cp)), 6.7-7.0 (m, Ph), 7.28 (s, CH(OMOHDBFlu)), 7.31 (s, CH(OMOHDBFlu)).

(ii) Synthesis of dibenzylmethylene($\eta^5$-cyclopentadienyl)($\eta^5$-octamethyloctahydrodibenzofluorenyl)zirconium dichloride (otherwise, 1,3-diphenylisopropylidene($\eta^5$-cyclopentadienyl)($\eta^5$-octamethyloctahydrodibenzofluorenyl)zirconium dichloride)

Into a 100 ml Kjeldahl flask purged thoroughly with nitrogen, equipped with a dropping funnel and a magnetic stirrer, was introduced dibenzylmethylene(cyclopentadienyl)(octamethyloctahydrodibenzofluorenyl)methane 0.37 g (0.57 mmol), and dehydrated ether 30 ml was further added. With cooling in an ice bath, 1.58 mol/L n-hexane solution of n-butyllithium, 0.40 ml (0.63 mmol), was added to the flask. The resulting solution was stirred for 20 hours at room temperature. With the flask cooled nearly to −78° C. in a dry ice/methanol bath, a 1:2 complex of zirconium tetrachloride and tetrahydrofuran 0.22 g (0.58 mmol) was added. Then the liquid temperature was gradually raised to room temperature, and the contents were stirred for 70 hours. After the solvent was distilled away, the resulting solid was washed with dehydrated n-hexane and extracted with dehydrated dichloromethane. The solvent was then distilled away to obtain an objective red solid (0.33 g, 73% yield). The $^1$H NMR spectrum and the FD-MS spectrum as measured with respect to the red solid are given below:

$^1$H NMR spectrum (270 MHz, CDCl$_3$): δ/ppm 1.10 (s, Me, 1H), 1.18 (s, Me, 1H), 1.41 (s, Me, 1H), 1.50 (s, Me, 1H), 1.5-1.8 (m, CH$_2$(OMOHDBFlu), 8H), 3.9-4.2 (m, CH$_2$, 4H), 5.75 (dd, J=2.6 Hz, J=2.6 Hz, Cp, 2H), 6.34 (dd, J=2.6 Hz, J=2.6 Hz, Cp, 2H), 7.17 (s, Ph?, 10H), 7.61 (s, Flu, 2H), 8.04 (s, Flu, 2H), FD-MS Spectrum: M/z 804 (M$^+$).

Example 10

Synthesis of dibenzylmethylene($\eta^5$-cyclopentadienyl){$\eta^5$-(3,6-di-tert-butylfluorenyl)}zirconium dichloride (otherwise, 1,3-diphenylisopropylidene ($\eta^5$-cyclopentadienyl){$\eta^5$-(3,6-di-tert-butylfluorenyl)}zirconium dichloride)

(i) Synthesis of dibenzylmethylene(cyclopentadienyl)(3,6-di-tert-butylfluorenyl)methane (otherwise, 2-cyclopentadienyl-2-{9-(3,6-di-tert-butylfluorenyl)}-1,3-diphenyl propane)

Into a 100 ml Kjeldahl flask purged thoroughly with nitrogen, equipped with a dropping funnel and a magnetic stirrer, were introduced 3,6-di-tert-butylfluorene 1.06 g (3.81 mmol) and dehydrated tetrahydrofuran 40 ml. Then a nitrogen atmosphere was again created inside the flask. With cooling in an ice bath, 1.57 mol/L n-hexane solution of n-butyllithium, 2.69 ml (4.22 mmol), was dropwise added by means of the dropping funnel. The resulting solution was stirred all night at room temperature. With the flask cooled in an ice bath, a solution of 6,6-dibenzyl fulvene 1.09 g (4.22 mmol) in 30 ml of dehydrated tetrahydrofuran, was dropwise added to the flask by means of the dropping funnel. Then the resulting solution was stirred all night at room temperature. After addition of 1 N hydrochloric acid aqueous solution 50 ml and ether 50 ml, the organic phase was collected by a separatory funnel. The organic phase was washed once with a saturated salt solution 50 ml and once with water 50 ml, and dried over magnesium sulfate. The solution was filtered to remove the magnesium sulfate, and the solvent of the filtrate was distilled away. The residue was purified by column chromatography to obtain an objective light yellow solid (1.15 g, 56% yield). The $^1$H NMR spectrum as measured with respect to the solid is given below:

$^1$H NMR spectrum (270 MHz, CDCl$_3$): δ/ppm 6.9-7.5 (m×10, CH(Flu, Ph)), 5.9-6.8 (m×5, CH(Cp)), 4.5 (s×2, CH(Flu)), 3.2 (s×2, CH$_2$(Et)), 3.0 (s, CH$_2$(Cp)), 2.8 (s, CH$_2$(Cp)), 1.4 (s, t-Bu).

(ii) Synthesis of dibenzylmethylene($\eta^5$-cyclopentadienyl){$\eta^5$-(3,6-di-tert-butylfluorenyl)}zirconium dichloride (otherwise, 1,3-diphenylisopropylidene($\eta^5$-cyclopentadienyl){$\eta^5$-(3,6-di-tert-butylfluorenyl)}zirconium dichloride)

Into a 100 ml Kjeldahl flask purged thoroughly with nitrogen, equipped with a dropping funnel and a magnetic stirrer, was introduced dibenzylmethylene(cyclopentadienyl)(3,6-di-tert-butylfluorenyl)methane 0.60g (1.12 mmol). Then a nitrogen atmosphere was again created inside the flask. Dehydrated ether 70 ml was further added to the flask. With cooling in an ice bath, 1.57 mol/L n-hexane solution of n-butyllithium, 1.46 ml (2.29 mmol), was dropwise added to the flask by means of the dropping funnel. The resulting solution was stirred all night at room temperature. With the flask cooled nearly to −78° C. in a dry ice/methanol bath, a 1:2 complex of zirconium tetrachloride and tetrahydrofuran, 0.40 g (1.07 mmol), was added. The liquid temperature was gradually raised to room temperature overnight. The solvent was dried out, and n-hexane soluble components were removed by addition of dehydrated n-hexane. The extraction was made with dehydrated dichloromethane, and the solvent was distilled away. The remainder was washed with dehydrated ether and then with dehydrated n-hexane, and dried to give an objective red solid (0.41 g, 53% yield). The $^1$H NMR spectrum and the FD-MS spectrum as measured with respect to the solid are given below:

$^1$H NMR spectrum (270 MHz, CDCl$_3$): δ/ppm 8.1 (d, 1.6 Hz, CH(Flu)), 7.7 (s×2, CH(Flu)), 7.4 (d×2, 1.9 Hz, CH(Flu)), 7.0-7.2 (m>6, CH(Ph)), 6.4 (t, 2.7 Hz, CH(Cp)), 5.9 (t, 2.7 Hz, CH(Cp)), 4.0-4.2 (s×4, CH$_2$(Et)), 1.4 (s, t-Bu), FD-MS Spectrum: M/z 696 (M$^+$).

Example 11

Synthesis of di(p-tolyl)methylene($\eta^5$-cyclopentadienyl){$\eta^5$-(2,7-di-tert-butylfluorenyl)}zirconium dichloride (i) Synthesis of 6,6-di-p-tolyl fulvene A 200 ml two-necked flask equipped with a dropping funnel, a magnetic stirrer and a three-way cock, was purged thoroughly with nitrogen. Into the flask, 4,4'-dimethylbenzophenone 6.72 g (31.9 mmol) was introduced, and dehydrated tetrahydrofuran 30 ml was further added. With cooling in an ice bath, 2 mol/L tetrahydrofuran solution of cyclopentadienyl sodium, 19.0 ml (38.0 mmol), was dropwise added to the flask. The contents were stirred at room temperature in a nitrogen atmosphere for 6 days to obtain a solution. With the flask cooled in an ice bath, 1 N hydrochloric acid aqueous solution 100 ml and diethyl ether 100 ml were gradually added in this order. The resulting two-phase solution was poured into a 300 ml separation funnel, and the funnel was shaken several times so that the water phase was removed. The obtained organic phase was washed twice with water 100 ml and once with a saturated salt solution 100 ml, and dried over anhydrous magnesium sulfate. The solution was filtered to remove solids, and the solvent of the filtrate was distilled away to obtain a red oily matter 9.40 g. The oily matter was subjected to silica gel chromatography to obtain 6.15 g of 6,6-di-p-tolyl fulvene as a red solid (23.8 mmol, 74.5% yield). Identification of the 6,6-di-p-tolyl fulvene was made by $^1$H NMR, the results being given below:

$^1$H NMR spectrum (270 MHz, CDCl$_3$): δ/ppm 2.39 (s, Me, 6H), 6.2-6.3 (m, Cp, 2H), 6.5-6.6 (m, Cp, 2H), 7.1-7.2 (m, Ar(p-tol), 2H).

(ii) Synthesis of (2,7-di-tert-butylfluorenyl)cyclopentadienyl di-p-tolyl methane A 300 ml two-necked flask equipped with a magnetic stirrer, a three-way cock and a dropping funnel, was purged thoroughly with nitrogen. 2,7-di-tert-butylfluorene 1.58 g (5.66 mmol) was placed in the flask, and dehydrated tetrahydrofuran 40 ml was further added. With cooling in an ice bath, 1.56 mol/L n-hexane solution of n-butyllithium, 3.8 ml (5.9 mmol), was dropwise added. The contents were stirred at room temperature in a nitrogen atmosphere for 6.5 hours to obtain a solution. With the flask cooled in a dry ice/methanol bath, a solution of 6,6-di-p-tolyl fulvene 1.76 g (6.82 mmol) in 20 ml of dehydrated tetrahydrofuran, was dropwise added to the flask over a period of 20 minutes by means of the dropping funnel. The liquid temperature was gradually raised to room temperature, and the contents were stirred in a nitrogen atmosphere at the temperature for 18 hours to obtain a solution. A saturated aqueous solution of ammonium chloride 100 ml and diethyl ether 100 ml were gradually added in this order. The resulting two-phase solution was poured into a 300 ml separation funnel, and the funnel was shaken several times so that the water phase was removed. The obtained organic phase was washed three times with water 100 ml and once with a saturated salt solution 100 ml, and dried over anhydrous magnesium sulfate. The solution was filtered to remove solids, and the solvent of the filtrate was distilled away. The resultant solid was washed with n-hexane to obtain 2.05 g of (2,7-di-tert-butylfluorenyl)cyclopentadienyl di-p-tolyl methane as a white solid (3.82 mmol, 67.5% yield). Identification of the (2,7-di-tert-butylfluorenyl)cyclopentadienyl di-p-tolyl methane was made by $^1$H NMR and the FD-mass spectrometric analysis, the results being given below:

$^1$H NMR spectrum (270 MHz, CDCl$_3$): δ/ppm 1.11 (s, t-Bu, 18H), 2.23 (s, Me, 6H), 2.8-3.0 (br, CH$_2$(Cp), 1H), 5.37 (s, CH(9-Flu), 1H), 6.0-6.4 (br, Cp, 4H), 6.8-7.0 (br, Ar(Flu), and Ar(p-tol), 6H), 7.0-7.3 (br, Ar(p-tol), 4H), 7.16 (dd, J=8.1 Hz, J=1.3 Hz, Ar(Flu), 2H), 7.34 (d, J=8.1 Hz, Ar(Flu), 2H), FD-MS Spectrum: M/z 536 (M$^+$).

(iii) Synthesis of di (p-tolyl)methylene($\eta^5$-cyclopentadienyl){$\eta^5$-(2,7-di-tert-butylfluorenyl)}zirconium dichloride A 100 ml Kjeldahl flask equipped with a dropping funnel and a magnetic stirrer, was purged thoroughly with nitrogen. Into the flask, (2,7-di-tert-butylfluorenyl)cyclopentadienyl di-p-tolyl methane 1.03 g (1.92 mmol) was introduced and slurried by addition of dehydrated diethyl ether 50 ml. With cooling in an ice bath, 1.56 mol/L n-hexane solution of n-butyllithium, 2.6 ml (4.1 mmol), was dropwise added to the slurry. The contents were stirred at room temperature in a nitrogen atmosphere for 17 hours. With the flask cooled in a dry ice/methanol bath, a 1:2 complex of zirconium tetrachloride and tetrahydrofuran 0.794 g (2.10 mmol) was added. The liquid temperature was slowly raised to room temperature, and the solution was stirred in a nitrogen atmosphere at the temperature for 3 days. After the solvent of the slurry was distilled away under reduced pressure, the residual solid was washed with dehydrated n-hexane and dehydrated diethyl ether, and then extracted with dehydrated dichloromethane. The solvent of the solution was distilled away under reduced pressure to obtain 1.146 g of di(p-tolyl)methylene($\eta^5$-cyclopentadienyl) {$\eta^5$-(2,7-di-tert-butylfluorenyl)}zirconium dichloride as an orange solid (1.644 mmol, 85.6% yield). Identification of the di(p-tolyl)methylene($\eta^5$-cyclopentadienyl){$\eta^5$-(2,7-di-tert-butylfluorenyl)}zirconium dichloride was made by $^1$H NMR and the FD-mass spectrometric analysis, the results being given below:

$^1$H NMR spectrum (270 MHz, CDCl$_3$): δ/ppm 1.03 (s, t-Bu, 18H), 2.32 (s, Me, 6H), 5.64 (t, J=2.7 Hz, Cp, 2H), 6.3-6.4 (m, Cp and Ar(Flu), 4H), 7.1-7.3 (m, Ar(p-tol), 4H), 7.58 (dd, J=8.9 Hz, J=1.6 Hz, Ar (Flu), 2H), 7.7-7.9 (m, Ar(p-tol), 4H), 8.02 (d, J=8.9 Hz, Ar(Flu), 2H), FD-MS Spectrum: M/z 696 (M$^+$).

Example 12

Synthesis of bis{3-(trifluoromethyl)phenyl}methylene($\eta^5$-cyclopentadienyl){$\eta^5$-(2,7-di-tert-butylfluorenyl)}zirconium dichloride (i) Synthesis of 6,6-{3-(trifluoromethyl)phenyl}fulvene A 300 ml two-necked flask equipped with a dropping funnel, a magnetic stirrer and a three-way cock, was purged thoroughly with nitrogen. Into the flask, cyclopentadiene 2.0 ml (24.4 mmol) and dehydrated tetrahydrofuran 80 ml were introduced. With cooling in an ice bath, 1.56 mol/L n-hexane solution of n-butyllithium, 17.3 ml (27.0 mmol), was dropwise added to the solution. The contents were stirred at room temperature in a nitrogen atmosphere for 16 hours, and hexamethylphosphoric triamide 4.0 ml was added to the solution. With the flask cooled in an ice bath, a solution of 3,3'-(trifluoromethyl)benzophenone 8.80 g (27.7 mmol) in 50 ml of dehydrated tetrahydrofuran, was gradually added to the flask. The resulting solution was stirred at room temperature in a nitrogen atmosphere for 2.5 hours. With the flask cooled in an ice bath, 1 N hydrochloric acid aqueous solution 100 ml and diethyl ether 50 ml were gradually added in this order. The resulting two-phase solution was poured into a 300 ml separation funnel, and the funnel was shaken several times so that the water phase was removed. The obtained organic phase was washed three times with water 100 ml and once with a saturated salt solution 100 ml, and dried over anhydrous magnesium sulfate for 1 hour. The solution was filtered to remove solids, and the solvent of the filtrate was distilled away to obtain an oily matter 11.31 g. The oily matter was subjected to silica gel chromatography to obtain 3.13 g of 6,6-{3-(trifluoromethyl)phenyl}fulvene as an orange solid (8.55 mmol, 35.0% yield). Identification of the 6,6-{3-(trifluoromethyl)phenyl}fulvene was made by $^1$H NMR, the results being given below:

$^1$H NMR spectrum (270 MHz, CDCl$_3$): δ/ppm 6.1-6.2 (m, Cp, 2H), 6.6-6.7 (m, Cp, 2H), 7.4-7.7 (m, Ar(Ph), 8H).

(ii) Synthesis of (2,7-di-tert-butylfluorenyl)cyclopentadienyl bis{3-(trifluoromethyl)phenyl}methane A 300 ml two-necked flask equipped with a magnetic stirrer, a three-way cock and a dropping funnel, was purged thoroughly with nitrogen. 2,7-di-tert-butylfluorene 0.695 g (2.50 mmol) was placed in the flask, and dehydrated tetrahydrofuran 40 ml was further added. With cooling in an ice bath, 1.56 mol/L n-hexane solution of n-butyllithium, 1.7 ml (2.7 mmol), was dropwise added. The contents were stirred at room temperature in a nitrogen atmosphere for 7 hours. With the flask cooled in a dry ice/methanol bath, a solution of 6,6-{3-(trifluoromethyl)phenyl}fulvene 1.01 g (2.76 mmol) in 20 ml of dehydrated tetrahydrofuran, was dropwise added to the flask over a period of 30 minutes by means of the dropping funnel. The liquid temperature was gradually raised to room temperature, and the solution was stirred in a nitrogen atmosphere at the temperature for 19 hours. A saturated aqueous solution of ammonium chloride 100 ml and diethyl ether 100 ml were gradually added in this order. The resulting two-phase solution was poured into a 300 ml separation funnel, and the funnel was shaken several times so that the water phase was removed. The obtained organic phase was washed three times with water 100 ml and once with a saturated salt solution 100 ml, and dried over anhydrous magnesium sulfate. The solution was filtered to remove solids, and the solvent of the filtrate was distilled away to obtain a solid 1.89 g. The solid was subjected to silica gel column chromatography to give 0.587 g of (2,7-di-tert-butylfluorenyl)cyclopentadienyl bis{3-(trifluoromethyl)phenyl}methane as a white solid (0.910 mmol, 36.4% yield). Identification of the (2,7-di-tert-butylfluorenyl)cyclopentadienyl bis{3-(trifluoromethyl)phenyl}methane was made by $^1$H NMR and the FD-mass spectrometric analysis, the results being given below:

$^1$H NMR spectrum (270 MHz, CDCl$_3$): δ/ppm 1.13 (s, t-Bu, 18H), 3.0-3.2 (br, CH$_2$(Cp), 1H), 5.50 (s, CH(9-Flu), 1H), 6.3-6.6 (br, Cp, 4H), 6.9-7.7 (m, Ar(Flu) and Ar(Ph), 14H), FD-MS Spectrum: M/z 644 (M$^+$).

(iii) Synthesis of bis{3-(trifluoromethyl)phenyl}methylene ($\eta^5$-cyclopentadienyl){$\eta^5$-(2,7-di-tert-butylfluorenyl)}zirconium dichloride A 100 ml Kjeldahl flask equipped with a dropping funnel and a magnetic stirrer, was purged thoroughly with nitrogen. Into the flask, (2,7-di-tert-butylfluorenyl)cyclopentadienyl bis{3-(trifluoromethyl)phenyl}methane 0.587 g (0.910 mmol) was introduced, and dehydrated diethyl ether 30 ml was further added. With cooling in an ice bath, 1.56 mol/L n-hexane solution of n-butyllithium, 1.24 ml (1.93 mmol), was dropwise added to the flask. The contents were stirred at room temperature in a nitrogen atmosphere for 16 hours. With the flask cooled in a dry ice/methanol bath, a 1:2 complex of zirconium tetrachloride and tetrahydrofuran 0.419 g (1.11 mmol) was added. The liquid temperature was slowly raised to room temperature, and the solution was stirred in a nitrogen atmosphere at the temperature for 3 days. After the solvent was distilled away under reduced pressure, the residual solid was washed with dehydrated n-hexane, and extracted with dehydrated dichloromethane. Dehydrated n-hexane was poured over the dichloromethane solution, and recrystallization was effected at about −20° C. to obtain 0.209 g of bis{3-(trifluoromethyl)phenyl}methylene($\eta^5$-cyclopentadienyl){$\eta^5$-(2,7-di-tert-butylfluorenyl)}zirconium dichloride as an orange solid (0.260 mmol, 28.5% yield). Identification of the bis{3-(trifluoromethyl)phenyl}methylene($\eta^5$-cyclopentadienyl){$\eta^5$-(2,7-di-tert-butylfluorenyl)}zirconium dichloride was made by $^1$H NMR and the FD-mass spectrometric analysis, the results being given below:

$^1$H NMR spectrum (270 MHz, CDCl$_3$): δ/ppm 1.01 (S, t-Bu, 18H), 5.6-5.7 (m, Cp, 2H), 6.16 (d, J=9.6 Hz, Ar(Flu), 2H), 6.3-6.5 (m, Cp, 2H), 7.5-7.7 (m, Ar(Flu) and Ar(Ph), 6H), 8.0-8.3 (m, Ar(Flu) and Ar(Ph), 6H).

FD-MS Spectrum: M/z 804 (M$^+$)

Example 13

Synthesis of di(p-tolyl)methylene($\eta^5$-cyclopentadienyl)($\eta^5$-octamethyloctahydrodibenzofluorenyl)zirconium dichloride (i) Synthesis of cyclopentadienyl(octamethyloctahydrodibenzofluorenyl)di-p-tolyl methane A 300 ml two-necked flask equipped with a magnetic stirrer, a three-way cock and a dropping funnel, was purged thoroughly with nitrogen. Into the flask, octamethyloctahydrodibenzofluorene 2.98 g (7.71 mmol) was introduced, and dehydrated tetrahydrofuran 60 ml was further added. With cooling in an ice bath, 1.56 mol/L n-hexane solution of n-butyllithium, 5.2 ml (8.1 mmol), was dropwise added. The contents were stirred at room temperature in a nitrogen atmosphere for 7 hours. With the flask cooled in a dry ice/methanol bath, a solution of 6,6-di-p-tolyl fulvene 2.40 g (9.27 mmol) in 30 ml of dehydrated tetrahydrofuran, was dropwise added to the flask over a period of 20 minutes by means of the dropping funnel. The liquid temperature was gradually raised to room temperature, and the solution was stirred in a nitrogen atmosphere at the temperature for 21 hours. A saturated aqueous solution of ammonium chloride 100 ml and diethyl ether 100 ml were gradually added in this order. The resulting two-phase solution was poured into a 300 ml separation funnel, and the funnel was shaken several times so that the water phase was removed. The obtained organic phase was washed twice with water 100 ml and once with a saturated salt solution 100 ml, and dried over anhydrous magnesium sulfate. The solution was filtered to remove solids, and the solvent of the filtrate was distilled away. The residual solid was washed with n-hexane to give 3.55 g of cyclopentadienyl(octamethyloctahydrodibenzofluorenyl)di-p-tolyl methane as a white solid (5.50 mmol, 71.3% yield). Identification of the cyclopentadienyl(octamethyloctahydrodibenzofluorenyl)di-p-tolyl methane was made by $^1$H NMR and the FD-mass spectrometric analysis, the results being given below:

$^1$H NMR spectrum (270 MHz, CDCl$_3$): δ/ppm 0.8-1.7 (m, Me(OMOHDBFlu), 24H), 2.1-2.4(br, CH$_2$(OMOHDBFlu), 8H), 2.7-3.1 (br, CH$_2$(CP), 1H), 5.2-5.4 (m, CH(9-OMO-HDBFlu), 1H), 5.8-6.5 (br, Cp, 4H), 6.7-7.5 (br, Ar(OMO-HDBFlu) and Ar(p-tol), 10H), 7.29 (s, Ar(OMOHDBFlu), 2H), FD-MS Spectrum: M/z 644 (M$^+$).

(ii) Synthesis of di(p-tolyl)methylene($\eta^5$-cyclopentadienyl)($\eta^5$-octamethyloctahydrodibenzofluorenyl)zirconium dichloride A 100 ml Kjeldahl flask equipped with a dropping funnel and a magnetic stirrer, was purged thoroughly with nitrogen. Into the flask, cyclopentadienyl(octamethyloctahydrodibenzofluorenyl)di-p-tolyl methane 1.10 g (1.56 mmol) was introduced, and dehydrated diethyl ether 30 ml was further added. With cooling in an ice bath, 1.56 mol/L n-hexane solution of n-butyllithium, 2.1 ml (3.3 mmol), was dropwise added. The contents were stirred at room temperature in a nitrogen atmosphere for 20 hours to obtain a slurry. With the flask cooled in a dry ice/methanol bath, a 1:2 complex of zirconium tetrachloride and tetrahydrofuran 0.552 g (1.46 mmol) was added. The liquid temperature was slowly raised to room temperature, and the contents were stirred in a nitrogen atmosphere at the temperature for 24 hours. After the solvent of the slurry was distilled away under reduced pressure, the residual solid was washed with n-hexane, and extracted with dichloromethane. The solvent of the extract solution was distilled away under reduced pressure to obtain 0.825 g of di(p-tolyl)methylene($\eta^5$-cyclopentadienyl)($\eta^5$-octamethyloctahydrodibenzofluorenyl)zirconium dichloride as a dark pink solid (1.02 mmol, 70.2% yield). Identification of the di(p-tolyl)methylene($\eta^5$-cyclopentadienyl)($\eta^5$-octamethyloctahydrodibenzofluorenyl)zirconium dichloride was made by $^1$H NMR and the FD-mass spectrometric analysis, the results being given below:

$^1$H NMR spectrum (270 MHz, CDCl$_3$): δ/ppm 0.82 (s, Me(OMOHDBFlu), 6H), 0.93 (s, Me(OMOHDBFlu), 6H), 1.40 (s, Me(OMOHDBFlu), 6H), 1.46 (s, Me(OMOHDBFlu), 6H), 1.5-1.7 (m, CH$_2$(OMOHDBFlu), 8H), 2.32 (s, Me, 6H), 5.53 (t, J=2.6 Hz, Cp, 2H), 6.17 (s, Ar(OMOHDBFlu), 2H), 6.25 (t, J=2.6 Hz, Cp, 2H), 7.1-7.3 (m, Ar(p-tol), 4H), 7.6-7.8 (m, Ar(p-tol), 4H), 8.03 (s, Ar(Flu), 2H), FD-MS Spectrum: M/z 804 (M$^+$).

Example 14

Synthesis of bis(4-tert-butylphenyl)methylene($\eta^5$-cyclopentadienyl)($\eta^5$-octamethyloctahydrodibenzofluorenyl)zirconium dichloride (i) Synthesis of 4,4'-di-tert-butylbenzophenone A 500 ml three-necked flask equipped with a magnetic stirrer, a three-way cock, a thermometer and a dropping funnel, was purged thoroughly with nitrogen. Anhydrous aluminum chloride 25.7 g (0.193 mmol) and dehydrated carbon tetrachloride 60 ml were introduced into the flask. With the flask cooled in an ice bath within 5 to 17° C. inside, tert-butylbenzene 26.55 g (0.1977 mmol) was dropwise added by means of the dropping funnel over a period of 1 hour. The contents were stirred for 1 hour at about 5° C. in a nitrogen atmosphere, and further for 24 hours at room temperature in a nitrogen atmosphere. The resultant slurry was gradually poured into a 3 L beaker containing ice water 600 ml. After addition of dichloromethane 500 ml into the beaker, the contents were stirred at room temperature for 3 hours. The resulting two-phase solution was poured into a 2 L separation funnel, and the funnel was shaken several times so that the water phase was removed. The obtained organic phase was washed once with a saturated aqueous solution of sodium hydrogencarbonate 200 ml and three times with water 200 ml, and dried over anhydrous magnesium sulfate. The solution was filtered to remove solids, and the solvent of the filtrate was distilled away. The residual solid was washed with n-hexane to give 12.67 g of 4,4'-di-tert-butylbenzophenone as a white solid (0.0430 mmol, 43.5% yield). Identification of the 4,4'-di-tert-butylbenzophenone was made by $^1$H NMR and the FD-mass spectrometric analysis, the results being given below:

$^1$H NMR spectrum (270 MHz, CDCl$_3$): δ/ppm 1.35 (s, t-Bu, 18H), 7.4-7.5 (m, Ar, 4H), 7.7-7.8 (m, Ar, 4H), FD-MS Spectrum: M/z 294 (M$^+$).

(ii) Synthesis of 6,6-bis(4-tert-butylphenyl)fulvene

A 300 ml two-necked flask equipped with a dropping funnel, a magnetic stirrer and a three-way cock, was purged thoroughly with nitrogen. Into the flask, 4,4'-di-tert-butylbenzophenone 6.03 g (20.5 mmol) and dehydrated tetrahydrofuran 40 ml were introduced. Further, hexamethylphosphoric triamide 4.0 ml was added into the flask. With cooling in an ice bath, 2.0 mol/L tetrahydrofuran solution of cyclopentadienyl sodium, 15.5 ml (31.0 mmol), was dropwise added. The contents were stirred at room temperature in a nitrogen atmosphere for 5 days. With the flask cooled in an ice bath, a saturated aqueous solution of ammonium chloride 100 ml and diethyl ether 100 ml were gradually added in this order. The resulting two-phase solution was poured into a 300 ml separation funnel, and the funnel was shaken several times so that the water phase was removed. The obtained organic phase was washed five times with water 50 ml and once with a saturated salt solution 50 ml, and dried over anhydrous magnesium sulfate. The solution was filtered to remove solids, and the solvent of the filtrate was distilled away to obtain a solid 8.02 g. The solid was subjected to silica gel chromatography to give 5.36 g of 6,6-bis(4-tert-butylphenyl)fulvene as an orange solid (15.64 mmol, 76.4% yield). Identification of the 6,6-bis(4-tert-butylphenyl)fulvene was made by $^1$H NMR, the results being given below:

$^1$H NMR spectrum (270 MHz, CDCl$_3$): δ/ppm 1.34 (s, t-Bu, 18H), 6.3-6.4 (m, Cp, 2H), 6.5-6.6 (m, Cp, 2H), 7.2-7.3 (m, Ar(Ph), 4H), 7.3-7.4 (m, Ar(Ph), 4H).

(iii) Synthesis of bis(4-tert-butylphenyl)cyclopentadienyl (octamethyloctahydrodibenzofluorenyl)methane A 300 ml two-necked flask equipped with a magnetic stirrer, a three-way cock and a dropping funnel, was purged thoroughly with nitrogen. Into the flask, octamethyloctahydrodibenzofluorene 2.01 g (5.21 mmol) and dehydrated tetrahydrofuran 40 ml were introduced. With cooling in an ice bath, 1.56 mol/L n-hexane solution of n-butyllithium, 3.5 ml (5.5 mmol), was dropwise added. The contents were stirred at room temperature in a nitrogen atmosphere for 1 day. With the flask cooled in a dry ice/methanol bath, a solution of 6,6-bis(4-tert-butylphenyl)fulvene 1.78 9 (5.20 mmol) in 20 ml of tetrahydrofuran, was dropwise added to the solution by means of the dropping funnel over a period of 20 minutes. The liquid temperature was then slowly raised to room temperature, and the solution was stirred in a nitrogen atmosphere at the temperature for 3 days. Then, a saturated aqueous solution of ammonium chloride 100 ml and diethyl ether 100 ml were gradually added to the solution in this order. The resulting two-phase solution was poured into a 300 ml separation funnel, and the funnel was shaken several timessothatthewaterphasewasremoved. Theobtainedorganic phase was washed three times with water 100 ml and once with a saturated salt solution 100 ml, and dried over anhydrous magnesium sulfate. The solution was filtered to remove solids, and the solvent of the filtrate was distilled away. The residual solid was washed with n-hexane to give 2.664 g of bis(4-tert-butylphenyl)cyclopentadienyl(octamethyloctahydrodibenzofluorenyl)methane as a white solid (3.65 mmol, 70.1% yield). Identification of the bis(4-tert-butylphenyl)cyclopentadienyl (octamethyloctahydrodibenzofluorenyl)methane was made by $^1$H NMR and the FD-mass spectrometric analysis, the results being given below:

$^1$H NMR spectrum (270 MHz, CDCl$_3$): δ/ppm 1.0-1.3 (m, Me(OMOHDBFlu), 24H), 1.24 (s, t-Bu, 18H), 1.5-1.7 (br, CH$_2$(OMOHDBFlu), 8H), 2.8-2.9 (br, CH$_2$(Cp), 1H), 5.3-5.4 (m, CH(9-OMOHDBFlu), 1H), 6.0-6.5 (br, Cp, 4H), 6.6-7.8 (br, Ar(OMOHDBFlu) and Ar(Ph), 12H), FD-MS Spectrum: M/z 729 (M$^+$+1).

(iv) Synthesis of bis(4-tert-butylphenyl)methylene(η$^5$-cyclopentadienyl)(η$^5$-octamethyloctahydrodibenzofluorenyl)zirconium dichloride A 100 ml Kjeldahl flask equipped with a dropping funnel and a magnetic stirrer, was purged thoroughly with nitrogen. Into the flask, bis(4-tert-butylphenyl)cyclopentadienyl(octamethyloctahydrodibenzofluorenyl)methane 0.709 g (0.972 mmol) and dehydrated diethyl ether 30 ml were introduced. With cooling in an ice bath, 1.56 mol/L n-hexane solution of n-butyllithium, 1.30 ml (2.03 mmol), was dropwise added. The contents were stirred at room temperature in a nitrogen atmosphere for 39 hours. With the flask cooled in a dry ice/methanol bath, a 1:2 complex of zirconium tetrachloride and tetrahydrofuran 0.273 g (0.724 mmol) was added to the solution. The liquid temperature was then slowly raised to room temperature, and the solution was stirred in a nitrogen atmosphere at the temperature for 24 hours. Then the solvent was distilled away under reduced pressure. The residual solid was washed with n-hexane and extracted with dichloromethane. The solvent of the extract solution was distilled away under reduced pressure to obtain 0.200 g of bis(4-tert-butylphenyl)methylene(η$^5$-cyclopentadienyl)(η$^5$-octamethyloctahydrodibenzofluorenyl)zirconium dichloride as a dark pink solid (0.225 mmol, 31.1% yield). Identification of the bis(4-tert-butylphenyl)methylene(η$^5$-cyclopentadienyl) (η$^5$-octamethyloctahydrodibenzofluorenyl)zirconium dichloride was made by $^1$H NMR and the FD-mass spectrometric analysis, the results being given below:

$^1$H NMR spectrum (270 MHz, CDCl$_3$): δ/ppm 0.80 (s, Me(OMOHDBFlu), 6H), 0.94 (s, Me(OMOHDBFlu), 6H), 1.31 (s, t-Bu, 18H), 1.40 (s, Me(OMOHDBFlu), 6H), 1.45 (s, Me(OMOHDBFlu), 6H), 1.5-1.8 (m, CH$_2$(OMOHDBFlu), 8H), 5.54 (t, J=2.6 Hz, Cp, 2H), 6.12 (s, Ar(OMOHDBFlu), 2H), 6.24 (t, J=2.6 Hz, Cp, 2H), 7.35 (ddd, J=19.8 Hz, J=8.2 Hz, J=2.0 Hz, Ar(Ph), 4H), 8.03 (s, Ar(Flu), 2H).

Example 15

Ethylene polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 0.52 mmol and a toluene solution of dimethylmethylene(η$^5$-cyclopentadienyl){η$^5$-(2,7-di-tert-butylfluorenyl)}zirconium dichloride 0.8 μmol were sequentially added into the autoclave to initiate polymerization. While continuously supplying an ethylene gas at a rate of 100 L/h, polymerization was carried out at atmospheric pressure and 75° C. for 3 minutes and terminated by addition of methanol in small amount. The polymer solution was poured into a large excess of methanol to precipitate a polymer, which was then dried under reduced pressure at 80° C. for 12 hours. As a result, a polymer was obtained in 2.38 g yield. The polymerization activity was 59.5 kg-PE/mmol-Zr·hr. The polymer had [η] of 4.49 dl/g.

Example 16

Ethylene polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.30 mmol and a toluene solution of dimethylmethylene($\eta^5$-cyclopentadienyl){$\eta^5$-(3,6-di-tert-butylfluorenyl)}zirconium dichloride 2.0 μmol were sequentially added into the autoclave to initiate polymerization. While continuously supplying an ethylene gas at a rate of 100 L/h, polymerization was carried out at atmospheric pressure and 75° C. for 4 minutes and terminated by addition of methanol in small amount. The polymer solution was poured into a large excess of methanol to precipitate a polymer, which was then dried under reduced pressure at 80° C. for 12 hours. As a result, a polymer was obtained in 4.30 g yield. The polymerization activity was 32.3 kg-PE/mmol-Zr·hr. The polymer had [η] of 2.78 dl/g.

Example 17

Ethylene polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.30 mmol and a toluene solution of diphenylmethylene($\eta^5$-cyclopentadienyl){$\eta^5$-(2,7-di-tert-butylfluorenyl)}zirconium dichloride 2.0 μmol were sequentially added into the autoclave to initiate polymerization. While continuously supplying an ethylene gas at a rate of 100 L/h, polymerization was carried out at atmospheric pressure and 75° C. for 2 minutes and terminated by addition of methanol in small amount. The polymer solution was poured into a large excess of methanol to precipitate a polymer, which was then dried under reduced pressure at 80° C. for 12 hours. As a result, a polymer was obtained in 2.46 g yield. The polymerization activity was 36.9 kg-PE/mmol-Zr·hr. The polymer had [η] of 8.30 dl/g.

Example 18

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.30 mmol and a toluene solution of diphenylmethylene($\eta^5$-cyclopentadienyl){$\eta^5$-(3,6-di-tert-butylfluorenyl)}zirconium dichloride 2.0 μmol were sequentially added into the autoclave to initiate polymerization. While continuously supplying an ethylene gas at a rate of 100 L/h, polymerization was carried out at atmospheric pressure and 75° C. for 4 minutes and terminated by addition of methanol in small amount. The polymer solution was poured into a large excess of methanol to precipitate a polymer, which was then dried under reduced pressure at 80° C. for 12 hours. As a result, a polymer was obtained in 7.10 g yield. The polymerization activity was 53.3 kg-PE/mmol-Zr·hr. The polymer had [η] of 5.60 dl/g.

Example 19

Ethylene polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.25 mmol and a toluene solution of cyclohexylidene($\eta^5$-cyclopentadienyl){$^5$-(2,7-di-tert-butylfluorenyl)}zirconium dichloride 1.25 μmol were sequentially added into the autoclave to initiate polymerization. While continuously supplying an ethylene gas at a rate of 100 L/h, polymerization was carried out at atmospheric pressure and 75° C. for 5 minutes and terminated by addition of methanol in small amount. The polymer solution was poured into a large excess of methanol to precipitate a polymer, which was then dried under reduced pressure at 80° C. for 12 hours. As a result, a polymer was obtained in 3.54 g yield. The polymerization activity was 34.0 kg-PE/mmol-Zr·hr. The polymer had [η] of 4.37 dl/g.

Example 20

Ethylene polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 0.52 mmol and a toluene solution of cyclohexylidene($\eta^5$-cyclopentadienyl){$\eta^5$-(3,6-di-tert-butylfluorenyl)}zirconium dichloride 0.8 μmol were sequentially added into the autoclave to initiate polymerization. While continuously supplying an ethylene gas at a rate of 100 L/h, polymerization was carried out at atmospheric pressure and 75° C. for 3 minutes and terminated by addition of methanol in small amount. The polymer solution was poured into a large excess of methanol to precipitate a polymer, which was then dried under reduced pressure at 80° C. for 12 hours. As a result, a polymer was obtained in 1.91 g yield. The polymerization activity was 47.8 kg-PE/mmol-Zr·hr. The polymer had [η] of 2.88 dl/g.

Example 21

Ethylene polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.3 mmol and a toluene solution of dimethylmethylene($\eta^5$-cyclopentadienyl)($\eta^5$-octamethyloctahydrodibenzofluorenyl)zirconium dichloride 2.0 μmol were sequentially added into the autoclave to initiate polymerization. While continuously supplying an ethylene gas at a rate of 100 L/h, polymerization was carried out at atmospheric pressure and 75° C. for 3.5 minutes and terminated by addition of isobutyl alcohol in small amount. The polymer solution was poured into a large excess of methanol to precipitate a polymer, which was then dried under reduced pressure at 80° C. for 12 hours. As a result, a polymer was obtained in 4.95 g yield. The polymerization activity was 42.4 kg-PE/mmol-Zr·hr. The polymer had [η] of 3.92 dl/g.

Example 22

Ethylene polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.3 mmol and a toluene solution of diphenylmethylene($\eta^5$-cyclopentadienyl)($\eta^5$-octamethyloctahydrodibenzofluorenyl)zirconium dichloride 2.0 μmol were sequentially added into the autoclave to initiate polymerization. While continuously supplying an ethylene gas at a rate of 100 L/h, polymerization was carried out at atmospheric pressure and 75° C. for 3 minutes and terminated by addition of isobutyl alcohol in small amount. The polymer solution was poured into a large excess of methanol to precipitate a polymer, which was then dried under reduced pressure at 80° C. for 12 hours. As a result, a polymer was obtained in 4.15 g yield. The polymerization activity was 41.5 kg-PE/mmol-Zr·hr. The polymer had [η] of 10.5 dl/g.

Example 23

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.3 mmol and a toluene solution of cyclohexylidene($\eta^5$-cyclopentadienyl)($\eta^5$-octamethyloctahydrodibenzofluorenyl)zirconium dichloride 2.0 μmol were sequentially added into the autoclave to initiate polymerization. While continuously supplying an ethylene gas at a rate of 100 L/h, polymerization was carried out at atmospheric pressure and 75° C. for 2 minutes and terminated by addition of isobutyl alcohol in small amount. The polymer solution was poured into a large excess of methanol to precipitate a polymer, which was then dried under reduced pressure at 80° C. for 12 hours. As a result, a polymer was obtained in 2.00 g yield. The polymerization activity was 30.0 kg-PE/mmol-Zr·hr. The polymer had [η] of 2.23 dl/g.

Example 24

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.3 mmol and a toluene solution of dimethylsilylene($\eta^5$-cyclopentadienyl)($\eta^5$-octamethyloctahydrodibenzofluorenyl)zirconium dichloride 2.0 μmol were sequentially added into the autoclave to initiate polymerization. While continuously supplying an ethylene gas at a rate of 100 L/h, polymerization was carried out at atmospheric pressure and 75° C. for 2 minutes and terminated by addition of methanol in small amount. The polymer solution was poured into a large excess of methanol to precipitate a polymer, which was then dried under reduced pressure at 80° C. for 12 hours. As a result, a polymer was obtained in 2.38 g yield. The polymerization activity was 35.7 kg-PE/mmol-Zr·hr. The polymer had [η] of 8.33 dl/g.

Example 25

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.3 mmol and a toluene solution of diphenylsilylene($\eta^5$-cyclopentadienyl)($\eta^5$-octamethyloctahydrodibenzofluorenyl)zirconium dichloride 2.0 μmol were sequentially added into the autoclave to initiate polymerization. While continuously supplying an ethylene gas at a rate of 100 L/h, polymerization was carried out at atmospheric pressure and 75° C. for 2.5 minutes and terminated by addition of methanol in small amount. The polymer solution was poured into a large excess of methanol to precipitate a polymer, which was then dried under reduced pressure at 80° C. for 12 hours. As a result, a polymer was obtained in 3.78 g yield. The polymerization activity was 45.4 kg-PE/mmol-Zr·hr. The polymer had [η] of 6.25 dl/g.

Example 26

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 0.52 mmol and a toluene solution of dicyclohexylsilylene($\eta^5$-cyclopentadienyl){$\eta^5$-(2,7-di-tert-butylfluorenyl)}zirconium dichloride 0.8 μmol were sequentially added into the autoclave to initiate polymerization. While continuously supplying an ethylene gas at a rate of 100 L/h, polymerization was carriedout at atmospheric pressure and 75° C. for 2.5 minutes and terminated by addition of methanol in small amount. The polymer solution was poured into a large excess of methanol to precipitate a polymer, which was then dried under reduced pressure at 80° C. for 12 hours. As a result, a polymer was obtained in 3.64 g yield. The polymerization activity was 109.2 kg-PE/mmol-Zr·hr. The polymer had [η] of 7.70 dl/g.

Example 27

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.3 mmol and a toluene solution of dibenzylmethylene($\eta^5$-cyclopentadienyl)($\eta^5$-octamethyloctahydrodibenzofluorenyl)zirconium dichloride 2.0 μmol were sequentially added into the autoclave to initiate polymerization. While continuously supplying an ethylene gas at a rate of 100 L/h, polymerization was carried out at atmospheric pressure and 75° C. for 2.5 minutes and terminated by addition of methanol in small amount. The polymer solution was poured into a large excess of methanol to precipitate a polymer, which was then dried under reduced pressure at 80° C. for 12 hours. As a result, a polymer was obtained in 1.76 g yield. The polymerization activity was 21.1 kg-PE/mmol-Zr·hr. The polymer had [η] of 2.62 dl/g.

Example 28

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.3 mmol and a toluene solution of dibenzylmethylene($\eta^5$-cyclopentadienyl)({$\eta^5$-(3,6-di-tert-butylfluorenyl)}zirconium dichloride 2.0 µmol were sequentially added into the autoclave to initiate polymerization. While continuously supplying an ethylene gas at a rate of 100 L/h, polymerization was carried out at atmospheric pressure and 75° C. for 5 minutes and terminated by addition of methanol in small amount. The polymer solution was poured into a large excess of methanol to precipitate a polymer, which was then dried under reduced pressure at 80° C. for 12 hours. As a result, a polymer was obtained in 3.57 g yield. The polymerization activity was 21.4 kg-PE/mmol-Zr·hr. The polymer had [$\eta$] of 2.46 dl/g.

Example 29

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 0.52 mmol and a toluene solution of di(p-tolyl)methylene($\eta^5$-cyclopentadienyl){$\eta^5$-(2,7-di-tert-butylfluorenyl)}zirconium dichloride 0.8 µmol were sequentially added into the autoclave to initiate polymerization. While continuously supplying an ethylene gas at a rate of 100 L/h, polymerization was carried out at atmospheric pressure and 75° C. for 3 minutes and terminated by addition of methanol in small amount. The polymer solution was poured into a large excess of methanol to precipitate a polymer, which was then dried under reduced pressure at 80° C. for 12 hours. As a result, a polymer was obtained in 2.00 g yield. The polymerization activity was 50.0 kg-PE/mmol-Zr·hr. The polymer had [$\eta$] of 10.5 dl/g.

Example 30

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.36 mol/L) 0.52 mmol and a toluene solution of bis{3-(trifluoromethyl)phenyl}methylene($\eta^5$-cyclopentadienyl){$\eta^5$-(2,7-di-tert-butylfluorenyl)}zirconium dichloride 0.8 µmol were sequentially added into the autoclave to initiate polymerization. While continuously supplying an ethylene gas at a rate of 100 L/h, polymerization was carried out at atmospheric pressure and 75° C. for 3 minutes and terminated by addition of methanol in small amount. The polymer solution was poured into a large excess of methanol to precipitate a polymer, which was then dried under reduced pressure at 80° C. for 12 hours. As a result, a polymer was obtained in 2.20 g yield. The polymerization activity was 55.0 kg-PE/mmol-Zr·hr. The polymer had [$\eta$] of 10.0 dl/g.

Example 31

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 0.52 mmol and a toluene solution of di(p-tolyl)methylene($\eta^5$-cyclopentadienyl)($\eta^5$-octamethyloctahydrodibenzofluorenyl)zirconium dichloride 0.8 µmol were sequentially added into the autoclave to initiate polymerization. While continuously supplying an ethylene gas at a rate of 100 L/h, polymerization was carried out at atmospheric pressure and 75° C. for 2 minutes and terminated by addition of methanol in small amount. The polymer solution was poured into a large excess of methanol to precipitate a polymer, which was then dried under reduced pressure at 80° C. for 12 hours. As a result, a polymer was obtained in 2.32 g yield. The polymerization activity was 87.0 kg-PE/mmol-Zr·hr. The polymer had [$\eta$] of 11.5 dl/g.

Example 32

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.36 mol/L) 0.52 mmol and a toluene solution of bis(4-tert-butylphenyl)methylene($\eta^5$-cyclopentadienyl)($\eta^5$-octamethyloctahydrodibenzofluorenyl)zirconium dichloride 0.8 µmol were sequentially added into the autoclave to initiate polymerization. While continuously supplying an ethylene gas at a rate of 100 L/h, polymerization was carried out at atmospheric pressure and 75° C. for 2 minutes and terminated by addition of methanol in small amount. The polymer solution was poured into a large excess of methanol to precipitate a polymer, which was then dried under reduced pressure at 80° C. for 12 hours. As a result, a polymer was obtained in 2.57 g yield. The polymerization activity was 96.4 kg-PE/mmol-Zr·hr. The polymer had [$\eta$] of 13.6 dl/g.

Comparative Example 1

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 0.52 mmol and a toluene solution of dimethylmethylene($\eta^5$-cyclopentadienyl)($\eta^5$-fluorenyl)zirconium dichloride 0.8 µmol were sequentially added into the autoclave to initiate polymerization. While continuously supplying an ethylene gas at a rate of 100 L/h, polymerization was carried out at atmospheric pressure and 75° C. for 6 minutes and terminated by addition of methanol in small amount. The polymer solution was poured into a large excess of methanol to precipitate a polymer, which was then dried under reduced pressure at 80° C. for 12 hours. As a result, a polymer was obtained in 1.64 g yield. The polymerization activity was 20.5 kg-PE/mmol-Zr·hr. The polymer had [$\eta$] of 3.08 dl/g.

Comparative Example 2

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 0.52 mmol and a toluene solution of diphenylmethylene($\eta^5$-cyclopentadienyl)($\eta^5$-fluorenyl)zirconium dichloride 0.8 µmol were sequentially added into the autoclave to initiate polymerization. While continuously supplying an ethylene gas at a rate of 100 L/h, polymerization was carried out at atmospheric pressure and 75° C. for 3 minutes and terminated by addition of methanol in small amount. The polymer solution was poured into a large excess of methanol to precipitate a polymer, which was then dried under reduced pressure at 80° C. for 12 hours. As a result, a polymer was obtained in 1.17 g yield. The polymerization activity was 29.3 kg-PE/mmol-Zr·hr. The polymer had [$\eta$] of 5.96 dl/g.

Comparative Example 3

Ethylene Polymerization

Toluene 400 ml was placed into a 500 ml glass autoclave which had been purged thoroughly with nitrogen, and ethylene was passed through toluene at a rate of 100 L/h for 10 minutes at 75° C. A toluene solution of methylaluminoxane (Al=1.21 mol/L) 1.30 mmol and a toluene solution of cyclohexylidene($\eta^5$-cyclopentadienyl)($\eta^5$-fluorenyl)zirconium dichloride 2.0 µmol were sequentially added into the autoclave to initiate polymerization. While continuously supplying an ethylene gas at a rate of 100 L/h, polymerization was carried out at atmospheric pressure and 75° C. for 5 minutes and terminated by addition of methanol in small amount. The polymer solution was poured into a large excess of methanol to precipitate a polymer, which was then dried under reduced pressure at 80° C. for 12 hours. As a result, a polymer was obtained in 0.80 g yield. The polymerization activity was 4.8 kg-PE/mmol-Zr·hr. The polymer had [$\eta$] of 3.82 dl/g.

Example 33

Ethylene/hexene copolymerization

[Preparation of Solid Catalyst Component]

Silica 8.5 kg dried at 200° C. for 3 hours was suspended in toluene 33 L, and a methylaluminoxane solution (Al=1.42 mol/L) 82.7 L was dropwise added to the suspension over a period of 30 minutes. The solution was heated to 115° C. in 1.5 hours, and the reaction was carried out at the temperature for 4 hours. Then the solution was cooled to 60° C., and the supernatant liquid was removed by decantation. The resultant solid catalyst component was washed three times with toluene and resuspended in toluene, so that a solid catalyst component (a) was obtained (total volume: 150 L).

[Preparation of Supported Catalyst]

The solid catalyst component (a) 237.4 µmol in terms of aluminum was suspended in toluene 5 ml, and the suspension was placed in a 100 ml two-necked flask which had been purged thoroughly with nitrogen. With the suspension being stirred, a toluene solution of dimethylmethylene($\eta^5$-cyclopentadienyl){$\eta^5$-(2,7-di-tert-butylfluorenyl)}zirconium dichloride 0.90 µmol was added at room temperature (23° C.). The solution was stirred at room temperature for 60 minutes, and the supernatant liquid was removed by decantation. The remainder was washed four times with n-heptane 10 ml, so that a solid catalyst component (b) was obtained.

[Ethylene/hexene Copolymerization]

n-Heptane 500 ml was placed into a 1000 ml autoclave purged thoroughly with nitrogen, and further 1 mol/L triisobutylaluminum 0.25 ml (0.25 mmol), 1-hexene 3.0 ml and the solid catalyst component (b) were introduced into the autoclave. The autoclave was pressurized to 8.0 kg/cm$^2$G with an ethylene gas, and polymerization was initiated at 80° C. The polymerization was carried out for 60 minutes while maintaining the pressure at 8.0 kg/cm$^2$G with an ethylene gas. Then the autoclave was depressurized, and the catalyst was deactivated with methanol. The polymer was filtered off, washed and dried in vacuo at 80° C. for 12 hours. The polymer weighed 40.5 g. The polymerization activity was 45.0 kg-Polymer/mmol-Zr·hr. According to the measurements, the polymer had MFR$_{2.16}$ of not more than 0.01 g/10 min, the density of 0.921 g/cm$^3$, Mw of 208,909 and Mw/Mn of 2.13.

Example 34

Ethylene/hexene Copolymerization

[Preparation of Supported Catalyst]

A solid catalyst component (c) was obtained in the same manner as in Example 33, except that the transition metal complex, dimethylmethylene($\eta^5$-cyclopentadienyl){$\eta^5$-(2,7-di-tert-butylfluorenyl)}zirconium dichloride, was changed to dimethylmethylene($\eta^5$-cyclopentadienyl){$\eta^5$-(3,6-di-tert-butylfluorenyl)}zirconium dichloride.

[Ethylene/hexene copolymerization]

A polymer was obtained in 26.2 g yield in the same manner as in Example 33, except that the solid catalyst component (c) 0.460 µmol in terms of Zr atom was used in place of the solid catalyst component (b). The polymerization activity was 57.0 kg-Polymer/mmol-Zr·hr. According to the measurements, the polymer had MFR$_{2.16}$ of not more than 0.01 g/10 min, the density of 0.924 g/cm$^3$, Mw of 166,186 and Mw/Mn of 2.33.

Example 35

Ethylene/hexene Copolymerization

[Preparation of Supported Catalyst]

A solid catalyst component (d) was obtained in the same manner as in Example 33, except that the transition metal complex, dimethylmethylene($\eta^5$-cyclopentadienyl){$\eta^5$-(2,7-di-tert-butylfluorenyl)}zirconium dichloride, was changed to diphenylmethylene($\eta^5$-cyclopentadienyl){$\eta^5$-(2,7-di-tert-butylfluorenyl)}zirconium dichloride.

[Ethylene/hexene Copolymerization]

A polymer was obtained in 28.6 g yield in the same manner as in Example 33, except that the solid catalyst component (d) 0.406 µmol in terms of Zr atom was used in place of the solid catalyst component (b). The polymerization activity was 70.4 kg-Polymer/mmol-Zr·hr. According to the measurements, the polymer had MFR$_{21.6}$ of not more than 0.01 g/10 min, the density of 0.917 g/cm$^3$, Mw of 557,800 and Mw/Mn of 2.28.

Example 36

Ethylene/hexene Copolymerization

[Preparation of Supported Catalyst]

A solid catalyst component (e) was obtained in the same manner as in Example 33, except that the transition metal complex, dimethylmethylene($\eta^5$-cyclopentadienyl){$^5$-(2,7-di-tert-butylfluorenyl)}zirconium dichloride, was changed to diphenylmethylene($\eta^5$-cyclopentadienyl){$^5$-(3,6-di-tert-butylfluorenyl)}zirconium dichloride.

[Ethylene/hexene Copolymerization]

A polymer was obtained in 50.6 g yield in the same manner as in Example 33, except that the solid catalyst component (e) 0.224 μmol in terms of Zr atom was used in place of the solid catalyst component (b) and that the polymerization was carried out for 70 minutes. The polymerization activity was 193.6 kg-Polymer/mmol-Zr·hr. According to the measurements, the polymer had $MFR_{21.6}$ of not more than 0.01 g/10 min, the density of 0.923 g/cm$^3$, Mw of 401,031 and Mw/Mn of 2.39.

Example 37

Ethylene/hexene Copolymerization

[Preparation of Supported Catalyst]

A solid catalyst component (f) was obtained in the same manner as in Example 33, except that the transition metal complex, dimethylmethylene($\eta^5$-cyclopentadienyl){$\eta^5$-(2,7-di-tert-butylfluorenyl)}zirconium dichloride, was changed to cyclohexylidene($\eta^5$-cyclopentadienyl){$\eta^5$-(2,7-di-tert-butylfluorenyl)}zirconium dichloride.

[Ethylene/hexene Copolymerization]

A polymer was obtained in 34.8 g yield in the same manner as in Example 33, except that the solid catalyst component (f) 0.684 μmol in terms of Zr atom was used in place of the solid catalyst component (b). The polymerization activity was 50.9 kg-Polymer/mmol-Zr·hr. According to the measurements, the polymer had $MFR_{2.16}$ of not more than 0.01 g/10 min, the density of 0.921 g/cm$^3$, Mw of 159,424 and Mw/Mn of 1.81.

Example 38

Ethylene/hexene Copolymerization

[Preparation of Supported Catalyst]

The solid catalyst component (a) 14.36 mmol in terms of aluminum was suspended in toluene, and the suspension was placed in a 300 ml four-necked flask equipped with a stirrer that had been purged thoroughly with nitrogen. With stirring, 2 mmol/L toluene solution of diphenylmethylene($\eta^5$-cyclopentadienyl)($\eta^5$-octamethyloctahydrodibenzofluorenyl)zirconium dichloride, 29.0 ml (0.0580 mmol), was added at room temperature. The solution was stirred for 60 minutes, and the supernatant liquid was removed by decantation. The remainder was washed four times with n-heptane 50 ml, and the resulting supported catalyst was slurried in about 100 ml of n-heptane, so that a solid catalyst component (g) was obtained as a catalyst suspension.

[Ethylene/hexene Copolymerization]

n-Heptane 500 ml was placed into a 1000 ml autoclave purged thoroughly with nitrogen, and further 1 mol/L tri-isobutylaluminum 0.25 ml (0.25 mmol), 1-hexene 3.0 ml and the solid catalyst component (g) 1.97 ml (1.082 μmol) were introduced into the autoclave. The autoclave was pressurized to 8.0 kg/cm$^2$G with an ethylene gas, and polymerization was initiated at 80° C. The polymerization was carried out for 30 minutes while maintaining the pressure at 8.0 kg/cm$^2$G with an ethylene gas. Then the autoclave was depressurized, and the catalyst was deactivated with methanol. The polymer was filtered off, washed and dried in vacuo at 80° C. for 12 hours. The polymer weighed 104.9 g. The polymerization activity was 193.9 kg-Polymer/mmol-Zr·hr. According to the measurements, the polymer had $MFR_{21.6}$ of not more than 0.01 g/10 min, the density of 0.918 g/cm$^3$, Mw of 668,700 and Mw/Mn of 2.45.

Example 39

Ethylene/hexene Copolymerization

[Preparation of Supported Catalyst]

A solid catalyst component (h) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to dimethylmethylene($\eta^5$-cyclopentadienyl)($\eta^5$-octamethyloctahydrodibenzofluorenyl)zirconium dichloride.

[Ethylene/hexene Copolymerization]

A polymer was obtained in 96.7 g yield in the same manner as in Example 38, except that the solid catalyst component (h) 0.460 μmol in terms of Zr atom was used in place of the solid catalyst component (g) and that the polymerization was carried out for 60 minutes. The polymerization activity was 210.2 kg-Polymer/mmol-Zr·hr. According to the measurements, the polymer had $MFR_{2.16}$ of not more than 0.01 g/10 min, the density of 0.920 g/cm$^3$, Mw of 201,500 and Mw/Mn of 1.86.

Example 40

Ethylene/hexene Copolymerization

[Preparation of Supported Catalyst]

A solid catalyst component (i) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to dimethylsilylene($\eta^5$-cyclopentadienyl)($\eta^5$-octamethyloctahydrodibenzofluorenyl)zirconium dichloride.

[Ethylene/hexene Copolymerization]

A polymer was obtained in 50.4 g yield in the same manner as in Example 38, except that the solid catalyst component (i) 0.224 μmol in terms of Zr atom was used in place of the solid catalyst component (g) and that the polymerization was carried out for 60 minutes. The polymerization activity was 224.8 kg-Polymer/mmol-Zr·hr. According to the measurements, the polymer had $MFR_{10}$ of not more than 0.01 g/10 min, the density of 0.924 g/cm$^3$, Mw of 362,800 and Mw/Mn of 2.42.

Example 41

Ethylene/hexene Copolymerization

[Preparation of Supported Catalyst]

A solid catalyst component (j) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to diphenylsilylene($\eta^5$-cyclopentadienyl)($\eta^5$-octamethyloctahydrodibenzofluorenyl)zirconium dichloride.

[Ethylene/hexene Copolymerization]

A polymer was obtained in 54.6 g yield in the same manner as in Example 38, except that the solid catalyst component (j) 0.304 μmol in terms of Zr atom was used in place of the solid catalyst component (g) and that the polymerization was carried out for 60 minutes. The polymerization activity was 179.2 kg-Polymer/mmol-Zr·hr. According to the measurements, the polymer had $MFR_{10}$ of not more than 0.01 g/10 min, the density of 0.927 g/cm$^3$, Mw of 477,638 and Mw/Mn of 2.07.

Example 42

Ethylene/hexene Copolymerization

[Preparation of Supported Catalyst]

A solid catalyst component (k) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to dicyclohexylsilylene($\eta^5$-cyclopentadienyl){$\eta^5$-(2,7-di-tert-butylfluorenyl)}zirconium dichloride.

[Ethylene/hexene Copolymerization]

A polymer was obtained in 49.9 g yield in the same manner as in Example 38, except that the solid catalyst component (k) 0.296 μmol in terms of Zr atom was used in place of the solid catalyst component (g) and that the polymerization was carried out for 60 minutes. The polymerization activity was 168.6 kg-Polymer/mmol-Zr·hr. According to the measurements, the polymer had $MFR_{2.16}$ of not more than 0.01 g/10 min, the density of 0.933 g/cm$^3$, Mw of 283,381 and Mw/Mn of 2.41.

Example 43

Ethylene/hexene Copolymerization

[Preparation of Supported Catalyst]

A solid catalyst component (l) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to di(p-tolyl)methylene($\eta^5$-cyclopentadienyl)({$\eta^5$-(2,7-di-tert-butylfluorenyl)}zirconium dichloride.

[Ethylene/hexene Copolymerization]

A polymer was obtained in 38.1 g yield in the same manner as in Example 38, except that the solid catalyst component (l) 0.423 μmol in terms of Zr atom was used in place of the solid catalyst component (g) and that the polymerization was carried out for 60 minutes. The polymerization activity was 90.1 kg-Polymer/mmol-Zr·hr. According to the measurements, the polymer had $MFR_{21.6}$ of not more than 0.01 g/10 min, the density of 0.918 g/cm$^3$, Mw of 643,870 and Mw/Mn of 2.36.

Example 44

Ethylene/hexene Copolymerization

[Preparation of Supported Catalyst]

A solid catalyst component (m) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to bis{3-(trifluoromethyl)phenyl}methylene ($\eta^5$-cyclopentadienyl){$\eta^5$-(2,7-di-tert-butylfluorenyl)}zirconium dichloride.

[Ethylene/hexene Copolymerization]

A polymer was obtained in 53.6 g yield in the same manner as in Example 38, except that the solid catalyst component (m) 0.401 μmol in terms of Zr atom was used in place of the solid catalyst component (g) and that the polymerization was carried out for 60 minutes. The polymerization activity was 133.7 kg-Polymer/mmol-Zr·hr. According to the measurements, the polymer had $MFR_{21.6}$ of not more than 0.01 g/10 min, the density of 0.928 g/cm$^3$, Mw of 677,910 and Mw/Mn of 2.68.

Example 45

Ethylene/hexene Copolymerization

[Preparation of Supported Catalyst]

A solid catalyst component (n) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to di(p-tolyl)methylene($\eta^5$-cyclopentadienyl) ($\eta^5$-octamethyloctahydrodibenzofluorenyl)zirconium dichloride.

[Ethylene/hexene Copolymerization]

A polymer was obtained in 48.2 g yield in the same manner as in Example 38, except that the solid catalyst component (n) 0.186 μmol in terms of Zr atom was used in place of the solid catalyst component (g) and that the polymerization was carried out for 60 minutes. The polymerization activity was 259.1 kg-Polymer/mmol-Zr·hr. According to the measurements, the polymer had $MFR_{21.6}$ of not more than 0.01 g/10 min, the density of 0.919 g/cm$^3$, Mw of 965,614 and Mw/Mn of 2.97.

Example 46

Ethylene/hexene Copolymerization

[Preparation of Supported Catalyst]

A solid catalyst component (o) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to bis(4-tert-butylphenyl)methylene($\eta^5$-cyclopentadienyl)($\eta^5$-octamethyloctahydrodibenzofluorenyl)zirconium dichloride.

[Ethylene/hexene Copolymerization]

A polymer was obtained in 39.99 g yield in the same manner as in Example 38, except that the solid catalyst component (o) 0.140 µmol in terms of Zr atom was used in place of the solid catalyst component (g) and that the polymerization was carried out for 60 minutes. The polymerization activity was 285.6 kg-Polymer/mmol-Zr·hr. According to the measurements, the polymer had $MFR_{21.6}$ of not more than 0.01 g/10 min, the density of 0.918 g/cm$^3$, Mw of 848,700 and Mw/Mn of 2.32.

Comparative Example 4

Ethylene/hexene Copolymerization

[Preparation of Supported Catalyst]

A solid catalyst component (p) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to dimethylmethylene($\eta^5$-cyclopentadienyl)($\eta^5$-fluorenyl)zirconium dichloride.

[Ethylene/hexene Copolymerization]

A polymer was obtained in 25.4 g yield in the same manner as in Example 38, except that the solid catalyst component (p) 1.052 µmol in terms of Zr atom was used in place of the solid catalyst component (g) and that the polymerization was carried out for 60 minutes. The polymerization activity was 24.1 kg-Polymer/mmol-Zr·hr. According to the measurements, the polymer had $MFR_{2.16}$ of not more than 0.01 g/10 min, the density of 0.925 g/cm$^3$, Mw of 166,538 and Mw/Mn of 2.24.

Comparative Example 5

Ethylene/hexene Copolymerization

[Preparation of Supported Catalyst]

A solid catalyst component (q) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to dimethylsilylene($\eta^5$-cyclopentadienyl)($\eta^5$-fluorenyl)zirconium dichloride.

[Ethylene/hexene Copolymerization]

A polymer was obtained in 30.3 g yield in the same manner as in Example 38, except that the solid catalyst component (q) 1.000 µmol in terms of Zr atom was used in place of the solid catalyst component (g) and that the polymerization was carried out for 60 minutes. The polymerization activity was 30.2 kg-Polymer/mmol-Zr·hr. According to the measurements, the polymer had $MFR_{2.16}$ of not more than 0.01 g/10 min, the density of 0.924 g/cm$^3$, Mw of 250,363 and Mw/Mn of 2.07.

Comparative Example 6

Ethylene/hexene Copolymerization

[Preparation of Supported Catalyst]

A solid catalyst component (r) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to diphenylmethylene($\eta^5$-cyclopentadienyl)($\eta^5$-fluorenyl)zirconium dichloride.

[Ethylene/hexene Copolymerization]

A polymer was obtained in 39.2 g yield in the same manner as in Example 38, except that the solid catalyst component (r) 1.020 µmol in terms of Zr atom was used in place of the solid catalyst component (g) and that the polymerization was carried out for 60 minutes. The polymerization activity was 38.4 kg-Polymer/mmol-Zr·hr. According to the measurements, the polymer had $MFR_{21.6}$ of 0.01 g/10 min, the density of 0.922 g/cm$^3$, Mw of 387,200 and Mw/Mn of 1.97.

Comparative Example 7

Ethylene/hexene Copolymerization

[Preparation of Supported Catalyst]

A solid catalyst component (s) was obtained in the same manner as in Example 38, except that the transition metal complex, diphenylmethylene($\eta^5$-cyclopentadienyl)($\eta^5$-octamethyloctahydrodibenzofluorenyl)zirconium dichloride, was changed to diphenylsilylene($\eta^5$-cyclopentadienyl)($\eta^5$-fluorenyl)zirconium dichloride.

[Ethylene/hexene Copolymerization]

A polymer was obtained in 27.5 g yield in the same manner as in Example 38, except that the solid catalyst component (s) 0.870 µmol in terms of Zr atom was used in place of the solid catalyst component (g) and that the polymerization was carried out for 60 minutes. The polymerization activity was 31.5 kg-Polymer/mmol-Zr·hr. According to the measurements, the polymer had $MFR_{2.16}$ of not more than 0.01 g/10 min, the density of 0.924 g/cm$^3$, Mw of 275,063 and Mw/Mn of 1.94.

The invention claimed is:

1. A bridged metallocene compound represented by the formula [I]:

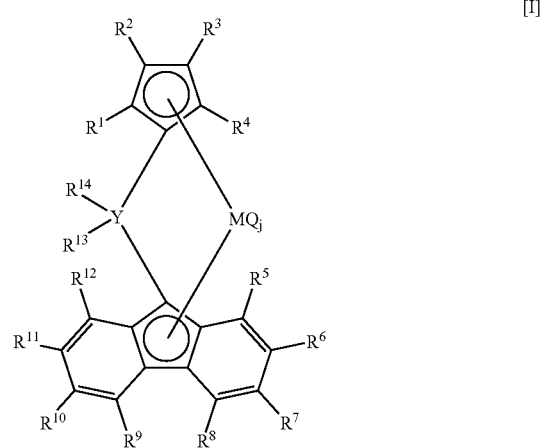

wherein Y is a carbon, silicon, germanium or tin atom; M is Ti or Zr; $R^1$ to $R^{12}$, which may be the same or different, are each hydrogen, a hydrocarbon group or a silicon-containing group; neighboring substituents of $R^5$ to $R^{12}$ may be linked with each other to form a ring; $R^{13}$ and $R^{14}$ are unsubstituted or substituted aryl groups, at least one of which is a substituted aryl group; Q is a halogen, a hydrocarbon group, an anionic ligand or a neutral ligand capable of coordination by a lone pair of electrons, and may be the same or different when plural; and j is an integer from 1 to 4.

2. The bridged metallocene compound of the formula [I] as claimed in claim 1, wherein $R^{13}$ or $R^{14}$ is a substituted aryl group which has one or more substituents of the same or different kind selected from hydrocarbon groups of 1 to 20 carbon atoms, halogen-containing hydrocarbon groups, halogen atoms, oxygen-containing groups and nitrogen-containing groups.

3. A bridged metallocene compound represented by the formula [I]:

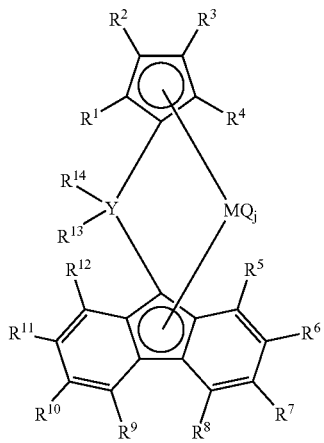

[I]

wherein Y is a carbon, silicon, germanium or tin atom; M is Ti, Zr or Hf; $R^1$ to $R^{12}$, which may be the same or different, are each hydrogen, a hydrocarbon group or a silicon-containing group; neighboring substituents of $R^5$ to $R^{12}$ may be linked with each other to form a ring; either or both of $R^{13}$ and $R^{14}$ is represented by $R^{15}R^{16}CH-$, in which $R^{15}$ and $R^{16}$ are each hydrogen, a hydrocarbon group or a silicon-containing group; and when one of $R^{13}$ and $R^{14}$ is not as defined above, then $R^{13}$ or $R^{14}$ is a hydrocarbon group or a silicon-containing group and may be linked with each other to form a ring (when $R^5$ to $R^{12}$ are all hydrogen or when $R^6$ and $R^{11}$ are both hydrocarbon groups, $R^{13}$ and $R^{14}$ are hydrocarbon groups other than phenyl, methyl and polymethylene groups, and when $R^7$ and $R^{10}$ are both hydrocarbon groups, $R^{13}$ and $R^{14}$ are hydrocarbon groups other than phenyl and methyl groups); Q is a halogen, a hydrocarbon group, an anionic ligand or a neutral ligand capable of coordination by a lone pair of electrons, and may be the same or different when plural; and j is an integer from 1 to 4.

4. The bridged metallocene compound of the formula [I] as claimed in claim 3, wherein either or both of $R^{13}$ and $R^{14}$ is represented by $R^{15}R^{16}CH-$, in which $R^{15}$ and $R^{16}$ are linked with each other to form a ring.

5. A bridged metallocene compound represented by the formula [I]:

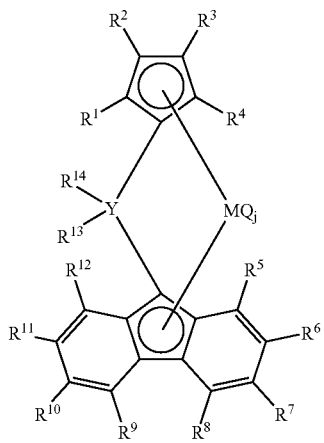

[I]

wherein Y is a carbon atom; M is Ti, Zr or Hf; $R^1$ to $R^{12}$, which may be the same or different, are each hydrogen, a hydrocarbon group or a silicon-containing group; neighboring substituents of $R^5$ to $R^{12}$ may be linked with each other to form a ring; $R^{13}$ and $R^{14}$ are linked with each other to form a polymethylene group represented by $-CH_2(CH_2)_n-$, in which n is an integer from 1 to 10; and $R^7$ and $R^{10}$ are hydrocarbon groups of 1 to 20 carbon atoms; Q is a halogen, a hydrocarbon group, an anionic ligand or a neutral ligand capable of coordination by a lone pair of electrons, and may be the same or different when plural; and j is an integer from 1 to 4.

6. A bridged metallocene compound represented by the formula [I]:

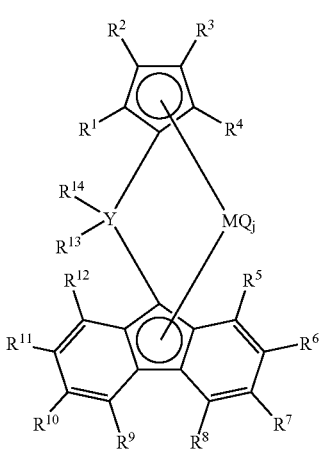

[I]

wherein Y is a carbon, silicon, germanium or tin atom; M is Ti, Zr or Hf; $R^1$ to $R^{12}$, which may be the same or different, are each hydrogen, a hydrocarbon group or a silicon-containing group, wherein arbitrary three or more substituents of $R^5$ to $R^{12}$ are hydrocarbon groups of 1 to 20 carbon atoms or silicon-containing groups; $R^{13}$ and $R^{14}$, which may be the same or different, are each a hydrocarbon group or a silicon-containing group and may be linked with each other to form a ring (when $R^6$ and $R^{11}$ are both hydrocarbon groups, $R^{13}$ and $R^{14}$ are hydrocarbon groups other than phenyl, methyl and polymethylene groups and when $R^7$ and $R^{10}$ are both hydrocarbon groups, $R^{13}$ and $R^{14}$ are hydrocarbon groups other than phenyl and methyl groups); Q is a halogen, a hydrocarbon group, an anionic ligand or a neutral ligand capable of coordination by a lone pair of electrons, and may be the same or different when plural; and j is an integer from 1 to 4.

7. The bridged metallocene compound of the formula [I] as claimed in claim 6, wherein $R^6$, $R^7$, $R^{10}$ and $R^{11}$ are hydrocarbon groups of 1 to 20 carbon atoms or silicon-containing groups.

8. The bridged metallocene compound of the formula [I] as claimed in claim 6, wherein $R^6$ and $R^7$, and $R^{10}$ and $R^{11}$ are linked with each other to form rings.

9. A bridged metallocene compound represented by the formula [I]:

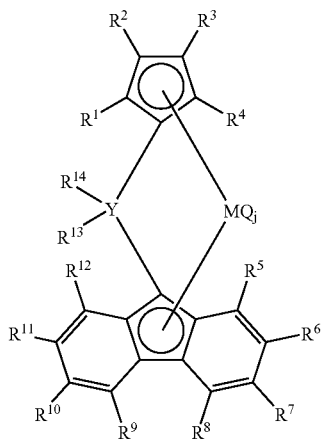

wherein Y is a silicon, germanium or tin atom; M is Ti, Zr or Hf; $R^1$ to $R^{12}$, which may be the same or different, are each hydrogen, a hydrocarbon group or a silicon-containing group, wherein $R^5$ to $R^{12}$ are not hydrogen at the same time; neighboring substituents of $R^5$ to $R^{12}$ may be linked with each other to form a ring; $R^{13}$ and $R^{14}$, which may be the same or different, are each a hydrocarbon group or a silicon-containing group and may be linked with each other to form a ring (when $R^6$ and $R^{11}$ are both hydrocarbon groups, $R^{13}$ and $R^{14}$ are hydrocarbon groups other than phenyl, methyl and polymethylene groups; when $R^7$ and $R^{10}$ are both hydrocarbon groups, $R^{13}$ and $R^{14}$ are hydrocarbon groups other than phenyl and methyl groups; and where $R^6$ and $R^{11}$ are not t-butyl groups when $R^{13}$ and $R^{14}$ are methyl or phenyl groups); Q is a halogen, a hydrocarbon group, an anionic ligand or a neutral ligand capable of coordination by a lone pair of electrons, and may be the same or different when plural; and j is an integer from 1 to 4.

10. The bridged metallocene compound of the formula [I] as claimed in claim 9, wherein Y is a silicon or germanium atom.

11. The bridged metallocene compound of the formula [I] as claimed in claim 1, wherein $R^1$ to $R^4$ are all hydrogen.

12. An olefin polymerization catalyst comprising the bridged metallocene compound of claim 1.

13. An olefin polymerization catalyst comprising:
(A) the bridged metallocene compound of claim 1 and
(B) at least one compound selected from:
(B-1) an organometallic compound,
(B-2) an organoaluminum oxy-compound and
(B-3) a compound which reacts with the metallocene compound (A) to form an ion pair.

14. A method for olefin polymerization, in which one or more monomers, essentially ethylene, selected from ethylene and α-olefins are polymerized in the presence of the olefin polymerization catalyst of claim 13 that an ethylene based polymer with an ethylene content of more than 50 mol % is obtained.

15. A method for olefin polymerization, in which one or more monomers, essentially ethylene, selected from ethylene and α-olefins are polymerized in the presence of an olefin polymerization catalyst which comprises a bridged metallocene compound of the formula [I'] so that an ethylene based polymer with an ethylene content of more than 50 mol % is obtained:

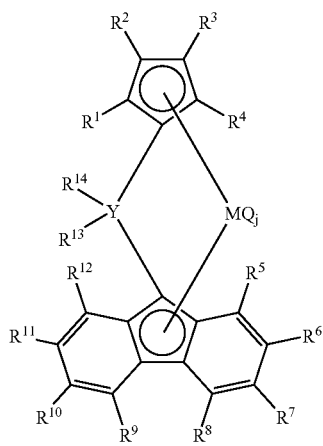

wherein Y is a carbon, silicon, germanium or tin atom; M is Ti, Zr or Hf; $R^1$ to $R^{12}$, which may be the same or different, are each hydrogen, a hydrocarbon group or a silicon-containing group; $R^5$ to $R^{12}$ are not hydrogen at the same time; neighboring substituents of $R^5$ $R^{12}$ may be linked with each other to form a ring; $R^{13}$ and $R^{14}$, which may be the same or different, are each a hydrocarbon group or a silicon-containing group and may be linked with each other to form a ring; Q is a halogen, a hydrocarbon group, an anionic ligand or a neutral ligand capable of coordination by a lone pair of electrons, and may be the same or different when plural; and j is an integer from 1 to 4.

16. The method for olefin polymerization as claimed in claim 14, wherein the metallocene compound of the formula [I] or [I'] has been supported on a carrier.

* * * * *